United States Patent
Li et al.

(10) Patent No.: US 9,434,760 B2
(45) Date of Patent: Sep. 6, 2016

(54) PROLINAMIDE DERIVATIVES AS THROMBIN INHIBITORS, PREPARATION METHOD AND APPLICATION THEREOF

(75) Inventors: Min Li, Ringoes, NJ (US); Hanbin Shan, Shanghai (CN); Yu Huang, Shanghai (CN); Zhedong Yuan, Shanghai (CN); Xiong Yu, Shanghai (CN)

(73) Assignee: SHANGHAI INSTITUTE OF PHARMACEUTICAL INDUSTRY, Shanghai (CN)

( * ) Notice: Subject to any disclaimer, the term of this patent is extended or adjusted under 35 U.S.C. 154(b) by 0 days.

(21) Appl. No.: 13/884,196

(22) PCT Filed: Nov. 4, 2011

(86) PCT No.: PCT/CN2011/081811
§ 371 (c)(1),
(2), (4) Date: Jul. 26, 2013

(87) PCT Pub. No.: WO2012/062187
PCT Pub. Date: May 18, 2012

(65) Prior Publication Data
US 2013/0296245 A1    Nov. 7, 2013

(30) Foreign Application Priority Data
Nov. 8, 2010 (CN) .......................... 2010 1 0535094

(51) Int. Cl.
| | |
|---|---|
| *A61K 38/06* | (2006.01) |
| *C07K 5/02* | (2006.01) |
| *C07D 207/16* | (2006.01) |
| *C07D 205/04* | (2006.01) |
| *C07D 211/60* | (2006.01) |
| *A61K 47/12* | (2006.01) |
| *A61K 47/38* | (2006.01) |
| *A61K 9/20* | (2006.01) |
| *A61K 9/48* | (2006.01) |

(52) U.S. Cl.
CPC ........... *C07K 5/0215* (2013.01); *A61K 9/2054* (2013.01); *A61K 9/2059* (2013.01); *A61K 9/4858* (2013.01); *A61K 9/4866* (2013.01); *A61K 38/06* (2013.01); *A61K 47/12* (2013.01); *A61K 47/38* (2013.01); *C07D 205/04* (2013.01); *C07D 207/16* (2013.01); *C07D 211/60* (2013.01)

(58) Field of Classification Search
None
See application file for complete search history.

(56) References Cited

U.S. PATENT DOCUMENTS 5,744,487 A * 4/1998 Ohshima et al. ............. 514/326
6,683,055 B1 * 1/2004 Hillen et al. ................. 514/20.1

FOREIGN PATENT DOCUMENTS

CN     1121068 A     4/1996
CN     1127509 C     11/2003

OTHER PUBLICATIONS

Muley, Laveena et al; "Enhancement of hydrophobic interactions and hydrogen bond strength by cooperativity: Synthesis, modeling, and moelcular dynamics simulations of a congeneric series of thrombin inhibitors." J. Med. Chem. (2010) 53 p. 2126-2135.*
The SigmaAldrich catalog entry for pipecolic acid, downloaded May 9, 2014.*
The ChemSpider entry for pyrrolidinylacetic acid, www.chemspider.com/Chemical-Structure.2042269.html, downloaded May 9, 2014.*
Hanessian, Stephan et al, "Structure-based organic synthesis of unnatural aeruginosin hybrids as potent inhibitors of thrombin." Bioorg. Med. Chem. Lett. (2007) 17(12) p. 3480-3485.*
Wang, Guijun et al, "Preparation of I-proline based aeruginosin 298-a analogs: optimization of the p1 moiety." Bioorg. Med. Chem. Lett. (2009) 19(14) p. 3798-3803.*
Sielaff, Frank et al, "Development of substrate analogue inhibitors for the human airway trypsin like protease hat." Bioorg. Med. Chem. Lett. (2011) 21(16) p. 4860-4864.*
Sisay, Mihiret Tekeste et al, "Identification of the first low-molecular-weight inhibitors of matriptase-2." J. Med. Chem. (2010) 53(15) p. 5523-5535.*
Oost, Thorsten K. et al, "Discovery of potent antagonists of the antiapoptotic protein xiap for the treatment of cancer." J. Med. Chem. (2004) 47 p. 4417-4426.*
Oost, Thorsten K. et al, "Discovery of potent antagonists of the antiapoptotic protein xiap for the treatment of cancer." J. Med. Chem. (2004) 47 p. 4417-4426, supporting information.*
Sielaff, F. et al. Development of substrate analogue inhibitors for the human airway trypsin-like protease HAT. Bioorg. Med. Chem. Lett. 2011, vol. 21, pp. 4860-4864.
Muley, L., et al. Enhancement of hydrophobic interactions and hydrogen bond strength by cooperativity: synthesis, modeling, and molecular dynamics simulations of a congeneric series of thrombin inhibitors. J. Med. Chem. 2010, vol. 53, pp. 2126-2135.
Hanessian, S. et al. Structure-based organic synthesis of unnatural aeruginosin hybrids as potent inhibitors of thrombin. Bioorg. Med. Chem. Lett. 2007, vol. 17, pp. 3480-3485.
Feng, D.M., et al. Discovery of a novel, selective, and orally bioavailable class of thrombin inhibitors incorporating aminopyridyl moieties at the P1 position. J. Med. Chem. 1997, vol. 40, pp. 3726-3733.
International Search Report for Application No. PCT/CN2011/081811 dated Feb. 16, 2012, 14 pages.

* cited by examiner

*Primary Examiner* — Maury Audet
*Assistant Examiner* — Fred Reynolds
(74) *Attorney, Agent, or Firm* — Brian C. Trinque; Lathrop & Gage LLP

(57) ABSTRACT

Provided are a compound of formula (I), pharmaceutically acceptable salts thereof, preparation methods and applications thereof for inhibiting thrombin, and applications in the treatment and prevention of thrombin-mediated and thrombin-related diseases.

2 Claims, No Drawings

PROLINAMIDE DERIVATIVES AS THROMBIN INHIBITORS, PREPARATION METHOD AND APPLICATION THEREOF

RELATED APPLICATIONS

The present application claims the benefit of priority of International Application No. PCT/CN2011/081811 filed Nov. 4, 2011, which claims priority to Chinese Patent Application No. 201010535094.4, filed Nov. 8, 2010. The entire contents of each of the above documents are incorporated herein by reference.

TECHNICAL FIELD

The present invention relates to a novel pharmaceutical compound, specifically to a method for preparation of the compound, its use as a medicament and a pharmaceutical composition containing the same. The novel pharmaceutical compound of the present invention can be used as competitive inhibitors of trypsin-like serine proteases, in particular thrombin.

BACKGROUND ART

The mortality of cardiovascular and cerebrovascular diseases has been the second in the world, wherein thromboembolism is the main reason for the high ratio of morbidity and mortality of cardiovascular and cerebrovascular diseases. Especially with the changes in the way people live and the increasing degree of aging of population, the morbidity of such diseases exhibits a continually increasing tendency. It makes the exploration and research of a medicament for effectively preventing and treating such diseases especially urgent, which is of great significance whether on clinical application or fundamental research.

The clinically used traditional anticoagulant drugs such as heparin, warfarin and hirudin have serious defects in terms of curative effect and safety, which greatly restrains their applications. For example, the heparin must be administered by injection, it fails to act on thrombin in blood clot, and may induce the symptom of thrombocytopenia. Warfarin serves as the sole oral drug, but since there is no definite drug target, the individual responses of anticoagulant differ greatly. There are a lot of influencing factors, and the coagulation function should be monitored. Consequently, it is particularly important to research and develop a novel anticoagulant drug with oral administration activity which is artificially synthesized.

Blood coagulation is the result of complicated action of series of enzymes, wherein a key step is to activate prothrombin to generate thrombin. As a trypsin-like serine protease, the main function of the thrombin is to hydrolyze fibrinogen to generate an insoluble stringy coagulation. Thrombin plays a vital role in cascade reaction of blood coagulation. Thus, the inhibition of the activity of thrombin can blocks the formation of the thrombus. Since its target is definite and different from the target of the traditional anticoagulant drugs, direct thrombin inhibitor (DTI) has a prospect to overcome the limitations in application of the traditional anticoagulant drugs. Obviously, the thrombin inhibitor which makes the treatment of thrombosis convenient, controlled and effectively selective and has oral administration bioactivity represents an attractive object.

Over the past thirty years, tremendous progress has been achieved in the research on the activity of artificially synthesized thrombin inhibitor as anticoagulant, and a large amount of small molecular thrombin inhibitors with high activity and high selectivity have been reported. For example, D-Phe-Pro-Arg-H and Me-D-Phe-Pro-Arg-H of tripeptide aldehyde thrombin inhibitors were reported in U.S. Pat. No. 4,346,078. Recently, D-Phe-Pro-agmatine and its derivatives were described as thrombin inhibitors in U.S. Pat. No. 4,346,078 and WO9311152. Afterwards, a tripeptide inhibitor in which 4-amidinobenzylamine is incorporated to replace agmatine and the like at P1 position was reported in WO9429336 and WO9523609.

In U.S. Pat. No. 4,101,653, Okamoto et al. disclose that series of arginine derivatives are designed and synthesized using N-p-tosyl-arginine methyl ester (TAMA) as a thrombin substrate, and find that argatroban has good inhibitory activity against thrombin. Argatroban is a reversible competitive thrombin inhibitor, which bonds the active position of thrombin to function and has high selectivity for thrombin, and has been approved as an injection on sale in 2001 after the pharmacological clinical research. It is clinically used to treat peripheral thrombosis diseases and acute stroke, and also can be used to treat thrombocytopenia and thrombosis syndrome induced by heparin.

Likewise, Stürzebecher et al. design and synthesize series of benzamidine compounds according to the structure of TAMA, and further modify the structure, finding that the inhibitory activity against thrombin of NAPAP is twice as strong as argatroban (J med chem., 1994, 37, 3889). Series of compounds obtained by changing benzamidine of NAPAP to piperidine-carboxamidine also have higher inhibitory activity against thrombin, wherein napsagatran synthesized by Hoffmann-La Roche Corp. has the strongest activity, and also has an effect on fibrinogen, and on which phase clinical research has been carried out, but its half life is short and the oral bioavailability is poor.

In WO9429336, Astra Corp. discloses a kind of benzamidine analogues, wherein melagatran has powerful effect inhibitory activity against thrombin, and can be safely used for deep venous thrombosis (DVT) if there are no obvious bleeding problems. However its oral bioavailability is low. Ximelagatran as its bipartite prodrug was further synthesized and came into the market in 2004. It is the first oral anticoagulant drug during over 60 years after warfarin. However serious liver damage was clinically found after it came into the market, and its use was terminated in February, 2006.

Moreover, a kind of thrombin inhibitors carrying particular D-diphenylglycine at P3 position is reported in WO9311152, WO9715190, U.S. Pat. No. 5,510,369. It is reported that such compounds have higher antithrombin activity (J Med Chem, 1997, 40, 830), some of which have higher oral bioavailability (J Med Chem, 1997, 40, 3687; J Med Chem, 1997, 40, 3726), compared to D-phenylglycine analogues.

Among the compounds reported, only a few have suitable properties of in vivo pharmacokinetics and pharmacodynamics. So far, the research of thrombin inhibitor is still one of hot research subjects in the field of pharmaceutical chemistry at present.

SUMMARY OF THE INVENTION

The first objective of the present invention is to provide a novel compound represented by formula (I), pharmaceutically acceptable salt and pharmaceutically acceptable prodrug thereof:

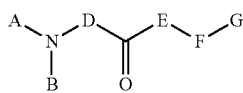

wherein:
A represents $C_{1-6}$ alkyl, cycloalkyl, heterocycloalkyl, aryl, —$SO_2R^1$, —$SO_3R^1$, —$COR^1$, —$CO_2R^1$, —$PO(OR^1)_2$, —$R^2$-cycloalkyl, —$R^2$-heterocycloalkyl, —$R^2$-aryl, —$R^2SO_2R^1$, —$R^2SO_3R^1$, —$R^2COR^1$, —$R^2CO_2R^1$, or —$R^2PO(OR^1)_2$;
wherein:
$R^1$ represents H, $C_{1-6}$ alkyl, cycloalkyl, heterocycloalkyl, aryl, —$R^3$-cycloalkyl, —$R^3$-heterocycloalkyl, —$R^3$-aryl, alkenyl or —$NR^4R^5$;
$R^2$ and $R^3$ represent $C_{1-6}$ alkyl;
wherein:
$R^4$ and $R^5$ represent independently H, $C_{1-6}$ alkyl, cycloalkyl or heterocycloalkyl;
B represents H:
D represents

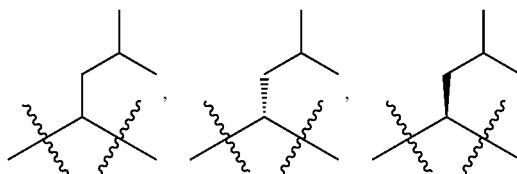

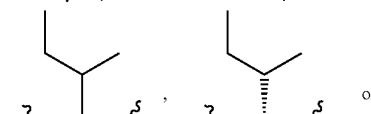

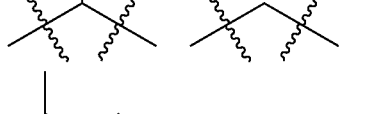

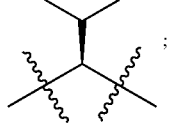

E represents

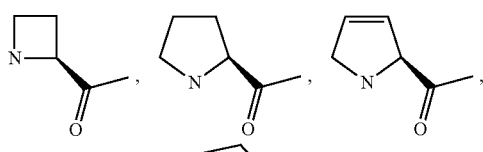

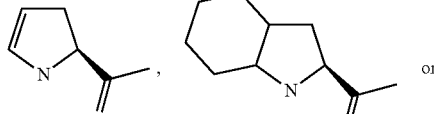

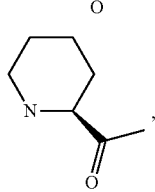

which are substituted or unsubstituted on the ring;
wherein the substituents on the ring can be carboxyl, halogen, alkyl, alkoxy, acyl, sulfonyl, sulfhydryl, alkylthio, cycloalkyl, heterocycloalkyl, amino, alkylamino, dialkylamino, cyano, ester group, trifluoromethyl or $C_{1-4}$ alkyl carrying the above groups.

F represents —NH—$(CH_2)_m$—$R^6$;
wherein:
m represents 0-3;
$R^6$ represents unsubstituted

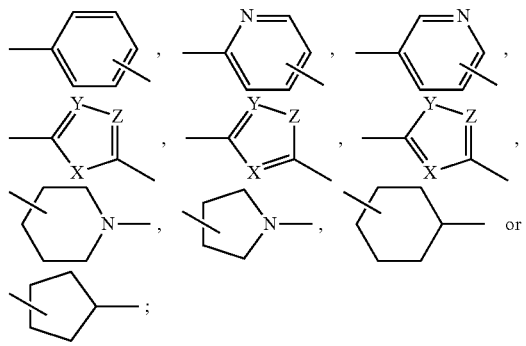

wherein:
X, Y and Z represent independently S, O or N;
G represents

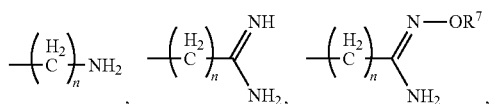

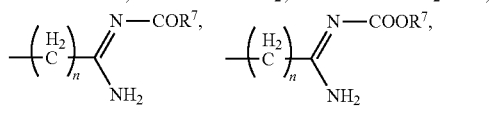

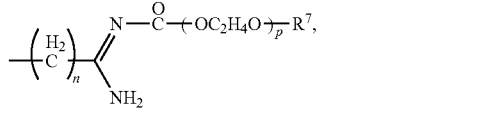

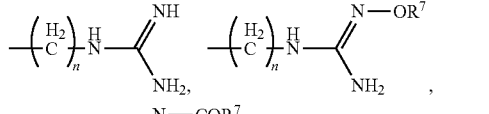

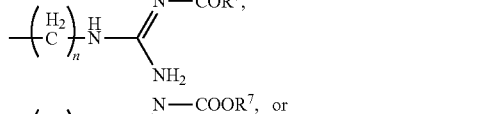

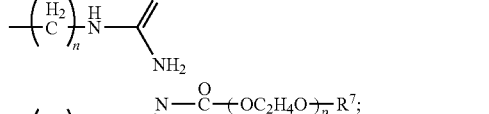

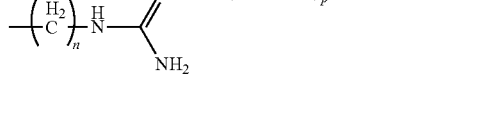

wherein:
n represents 0-3;
p represents 1-8;
$R^7$ represents H or $C_{1-6}$ alkyl.

In a preferable aspect according to the present invention, in the compound of formula (I), A represents —$SO_2R^1$, —$SO_3R^1$, —$COR^1$, —$CO_2R^1$, —$PO(OR^1)_2$, —$R^2$-cycloalkyl, —$R^2$-heterocycloalkyl, —$R^2$-aryl, —$R^2SO_2R^1$, —$R^2SO_3R^1$, —$R^2COR^1$, —$R^2CO_2R^1$ or —$R^2PO(OR^1)_2$;

wherein:

R¹ represents H, $C_{1-6}$ alkyl, cycloalkyl, heterocycloalkyl, aryl, —R³-cycloalkyl, —R³-heterocycloalkyl, —R³-aryl, alkenyl or —NR⁴R⁵;

R² and R³ represent $C_{1-6}$ alkyl;

wherein:

R⁴ and R⁵ represent independently H, $C_{1-6}$ alkyl, cycloalkyl or heterocycloalkyl;

D represents

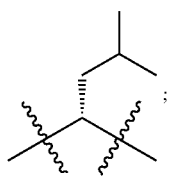

E represents

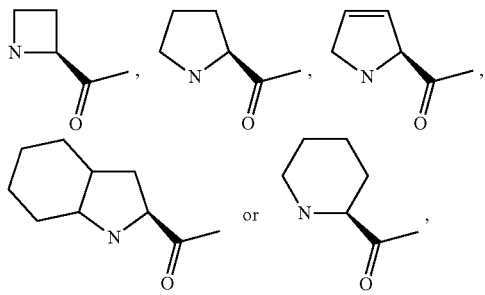

which are substituted or unsubstituted on the ring;

wherein the substituents on the ring can be carboxyl, halogen, alkyl, alkoxy, acyl, sulfonyl, sulfhydryl, alkylthio, cycloalkyl, heterocycloalkyl, amino, alkylamino, dialkylamino, cyano, ester group, trifluoromethyl or $C_{1-4}$ alkyl carrying the above groups.

F represents —NH—$(CH_2)_m$—R⁶;

wherein:

m represents 0-3;

R⁶ represents unsubstituted

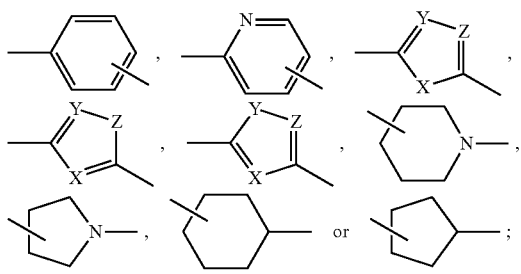

wherein: X, Y and Z represent independently S, O or N;

G represents

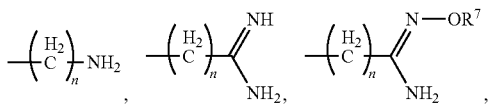

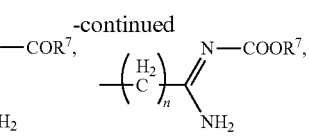

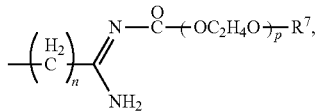

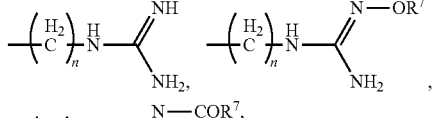

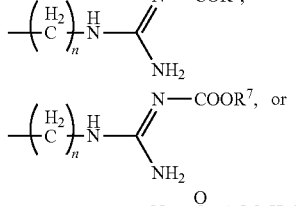

wherein:

n represents 0-3;

p represents 1-6;

R⁷ represents H or $C_{1-6}$ alkyl.

Among these compounds, the particularly preferable compounds are the compounds in which A represents —$SO_2R^1$, —$COR^1$, —$CO_2R^1$, —R²-cycloalkyl, —R²-heterocycloalkyl, —R²-aryl, —$R^2SO_2R^1$, —$R^2COR^1$ or —$R^2CO_2R^1$;

wherein:

R¹ represents H, $C_{1-6}$ alkyl, cycloalkyl, heterocycloalkyl, aryl, —R³-cycloalkyl, —R³-heterocycloalkyl, —R³-aryl, alkenyl or —NR⁴R⁵;

R² and R³ represent $C_{1-6}$ alkyl;

wherein:

R⁴ and R⁵ represent independently H, $C_{1-6}$ alkyl, cycloalkyl or heterocycloalkyl;

E is

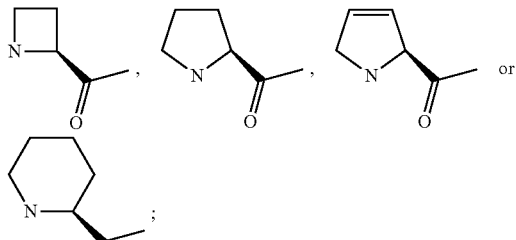

F is —NH—$(CH_2)_m$—R⁶;

wherein:

m is 1;

R⁶ represents unsubstituted

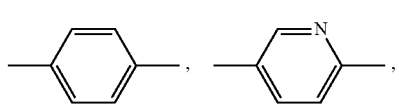

-continued

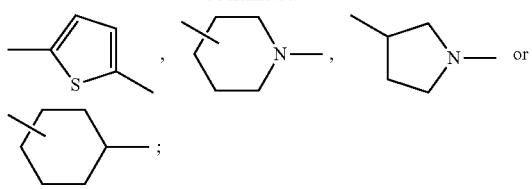

G represents

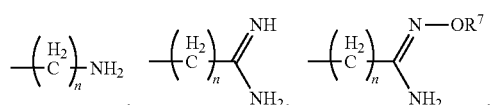

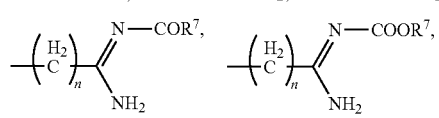

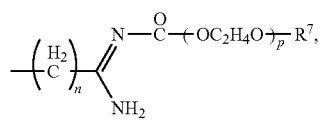

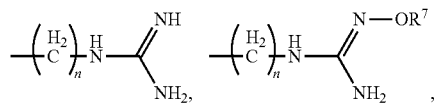

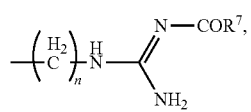

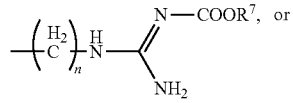

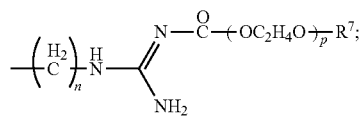

wherein:

n represents 0-3;

p represents 1-6;

$R^7$ represents H or $C_{1-6}$ alkyl.

Among the compounds of formula (I), the more preferable compound group are the compounds in which A represents $-SO_2R^1$, $-SO_3R^1$, $-CO_2R^1$, $-PO(OR^1)_2$, $-R^2$-cycloalkyl, $-R^2$-heterocycloalkyl, $-R^2$-aryl, $-R^2SO_2R^1$, $-R^2SO_3R^1$, $-R^2COR^1$, $-R^2CO_2R^1$ or $-R^2PO(OR^1)_2$;

wherein:

$R^1$ represents H, $C_{1-6}$ alkyl, cycloalkyl, heterocycloalkyl, aryl, $-R^3$-cycloalkyl, $-R^3$-heterocycloalkyl, $-R^3$-aryl, alkenyl or $-NR^4R^5$;

$R^2$ and $R^3$ represent $C_{1-6}$ alkyl;

wherein:

$R^4$ and $R^5$ represent independently H, $C_{1-6}$ alkyl, cycloalkyl or heterocycloalkyl;

D represents

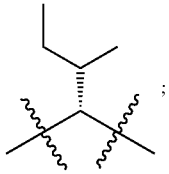

E represents

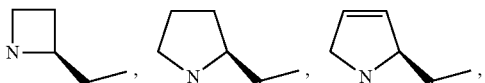

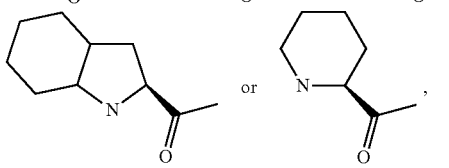

which are substituted or unsubstituted on the ring;

wherein the substituents on the ring can be carboxyl, halogen, alkyl, alkoxy, acyl, sulfonyl, sulfhydryl, alkylthio, cycloalkyl, heterocycloalkyl, amino, alkylamino, dialkylamino, cyano, ester group, trifluoromethyl or $C_{1-4}$ alkyl carrying the above groups.

F represents $-NH-(CH_2)_m-R^6$; F wherein:

m represents 0-3;

$R^6$ represents unsubstituted

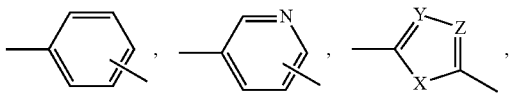

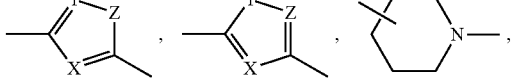

wherein:

X, Y and Z represent independently S, O or N;

G represents

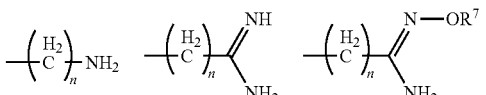

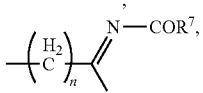

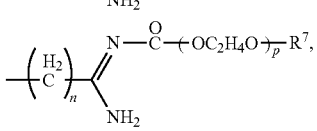

-continued

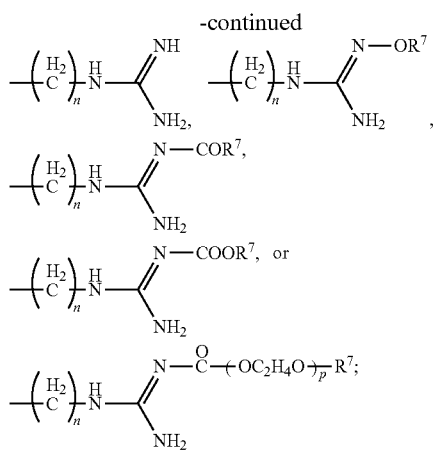

wherein:
n represents 0-3;
p represents 1-6;
$R^7$ represents H or $C_{1-6}$ alkyl.

More preferably, among these compounds, wherein A represents —$SO_2R^1$, —$CO_2R^1$, —$R^2$-cycloalkyl, —$R^2$-heterocycloalkyl, —$R^2$-aryl, —$R^2SO_2R^1$, —$R^2COR^1$ or —$R^2CO_2R^1$;
wherein:
$R^1$ represents H, $C_{1-6}$ alkyl, cycloalkyl, heterocycloalkyl, aryl, —$R^3$-cycloalkyl, —$R^3$-heterocycloalkyl, —$R^3$-aryl, alkenyl or —$NR^4R^5$;
$R^2$ and $R^3$ represent $C_{1-6}$ alkyl;
wherein:
$R^4$ and $R^5$ represent independently H, $C_{1-6}$ alkyl, cycloalkyl or heterocycloalkyl;

E is

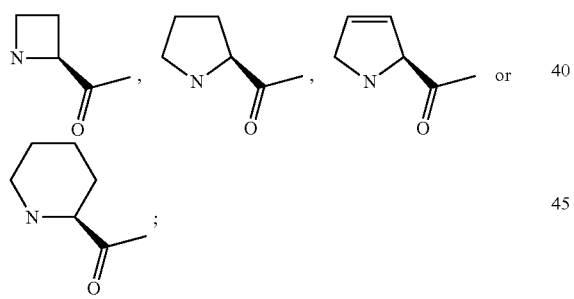

F is —NH—$(CH_2)_m$—$R^6$;
wherein:
m is 1;
$R^6$ represents unsubstituted

G represents wherein:
n represents 0-3;
p represents 1-6;
$R^7$ represents H or $C_{1-6}$ alkyl.

DETAILED DESCRIPTION OF THE INVENTION

In the present invention, the following definitions are used.

In accordance with the convention in the art, ⤴ is used in the structural formula herein to depict the bond that is the point of attachment of the moiety or substituent to the core or the backbone structure.

"$C_{1-6}$ alkyl" means straight or branched chain monovalent residues consisting of 1-6 saturated and/or unsaturated carbon atoms and hydrogen atoms, such as methyl (Me), ethyl (Et), propyl, isopropyl, butyl (Bu), isobutyl, t-butyl (t-Bu), vinyl, pentenyl, propenyl, butenyl, ethynyl, propynyl, butynyl, pentynyl, hexynyl, and the like, which may be unsubstituted or substituted by one or more suitable substituents as defined below.

"Cycloalkyl" means non-aromatic monovalent monocyclic, bicyclic or tricyclic residues containing 3, 4, 5, 6, 7, 8, 9, 10, 11, 12, 13 or 14 carbon atoms, each of which may be saturated or unsaturated, and may be unsubstituted or substituted by one or more suitable substituents as defined below, and may be condensed with one or more heterocycloalkyls or aryls, which themselves may be unsubstituted or substituted by one or more suitable substituents as defined below.

"Heterocycloalkyl" means non-aromatic monovalent monocyclic, bicyclic or tricyclic residues having 3, 4, 5, 6, 7, 8, 9, 10, 11, 12, 13 or 14 carbon atoms, which include 1, 2, 3, 4, 5 or 6 heteroatoms including nitrogen, oxygen and sulfur, and may be condensed with one or more heterocycloalkyls or aryls, which themselves may be unsubstituted or substituted by one or more suitable substituents as defined below.

"Aryl" means phenyl, naphthyl, 5- or 6-membered aromatic heterocycle, said heterocycle has one or two same or different heteroatoms selected from nitrogen, oxygen and sulfur, which may be unsubstituted or substituted by one or more suitable substituents as defined below, and may be condensed with one or more cycloalkyl, heterocycloalkyl or 5- or 6-membered aromatic heterocycle, which themselves may be unsubstituted or substituted by one or more suitable substituents as defined below.

"Substituent" is hydroxyl, carboxyl, halogen, alkyl, alkoxy, acyl, sulfonyl, sulfhydryl, alkylthio, cycloalkyl, heterocycloalkyl, amino, alkylamino, dialkylamino, cyano, ester group, trifluoromethyl or $C_{1-4}$ alkyl carrying the above groups.

The 5- or 6-membered aromatic heterocycle is substituted or unsubstituted structural unit represented by formula (II):

wherein the substituent is hydroxyl, carboxyl, halogen, alkyl, alkoxy, acyl, sulfonyl, sulfhydryl, alkylthio, cycloalkyl, heterocycloalkyl, amino, alkylamino, dialkylamino, cyano, ester group, trifluoromethyl or $C_{1-4}$ alkyl carrying the above groups.

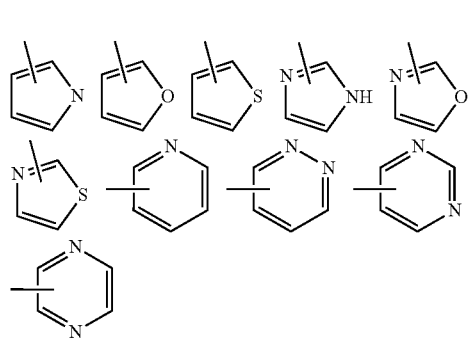

(II)

The benzo-saturated or unsaturated heterocycle is substituted or unsubstituted structural unit represented by formula (III):

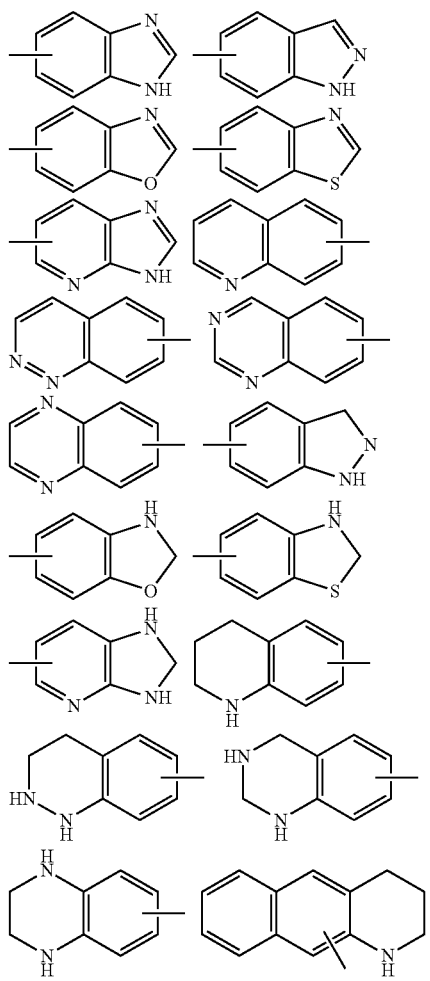

(III)

wherein the substituent is hydroxyl, carboxyl, halogen, alkyl, alkoxy, acyl, sulfonyl, sulfhydryl, alkylthio, cycloalkyl, heterocycloalkyl, amino, alkylamino, dialkylamino, cyano, ester group, trifluoromethyl or $C_{1-4}$ alkyl carrying the abovegroups.

The preferable specific compounds of the present invention include, but not limited to:

| A | D | E | F-G |
|---|---|---|---|
| benzenesulfonyl | D,L-leucyl | L-prolyl | -NH-C6H4-C(=NH)NH2 |
| benzenesulfonyl | D,L-leucyl | L-prolyl | -NH-C6H4-C(=N-OH)NH2 |
| benzylsulfonyl | D,L-leucyl | L-prolyl | -NH-C6H4-C(=NH)NH2 |

-continued

| A | D | E | F-G |
|---|---|---|---|
| benzylsulfonyl | D,L-leucyl | L-prolyl | 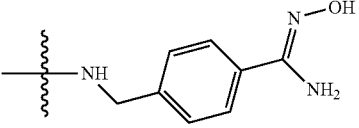 |
| benzoyl | D,L-leucyl | L-prolyl | 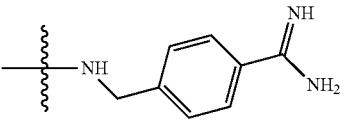 [SMILES: *NCc1ccc(C(=N)N)cc1] |
| benzoyl | D,L-leucyl | L-prolyl | 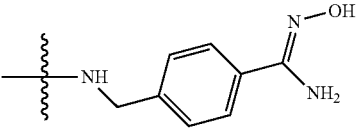 [SMILES: *NCc1ccc(/C(N)=N/O)cc1] |
| phenylacetyl | D,L-leucyl | L-prolyl | 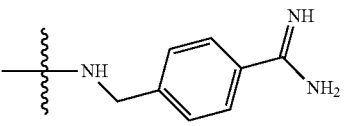 |
| phenylacetyl | D,L-leucyl | L-prolyl | 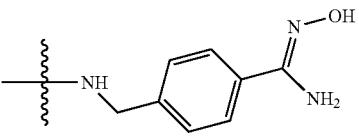 [SMILES: *NCc1ccc(/C(N)=N/O)cc1] |
| carboxylmethyl | D,L-leucyl | L-prolyl | 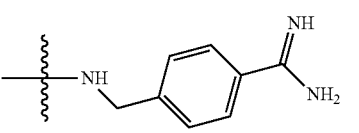 [SMILES: *NCc1ccc(C(=N)N)cc1] |
| carboxylmethyl | D,L-leucyl | L-prolyl | 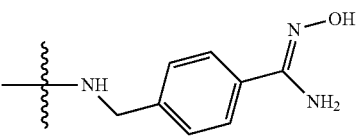 [SMILES: *NCc1ccc(/C(N)=N/O)cc1] |
| benzoyl | D,L-isoleucyl | L-prolyl | 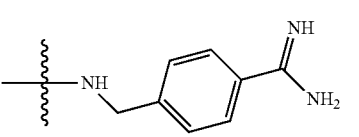 [SMILES: *NCc1ccc(C(=N)N)cc1] |
| benzoyl | D,L-isoleucyl | L-prolyl | 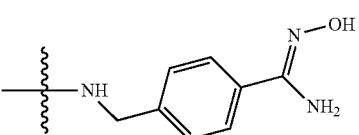 |
| phenylacetyl | D,L-isoleucyl | L-prolyl | 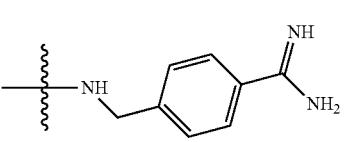 |
| phenylacetyl | D,L-isoleucyl | L-prolyl |  |

-continued

| A | D | E | F-G |
|---|---|---|-----|
| carboxylmethyl | D,L-isoleucyl | L-prolyl | -NH-CH2-C6H4-C(=NH)NH2 |
| carboxylmethyl | D,L-isoleucyl | L-prolyl | -NH-CH2-C6H4-C(=N-OH)NH2 |
| benzenesulfonyl | L-leucyl | L-prolyl | -NH-CH2-C6H4-C(=NH)NH2 |
| benzenesulfonyl | D-leucyl | L-prolyl | -NH-CH2-C6H4-C(=NH)NHCbz |
| benzenesulfonyl | D-leucyl | L-prolyl | -NH-CH2-C6H4-C(=NH)NH2 |
| benzylsulfonyl | D-leucyl | L-prolyl | -NH-CH2-C6H4-C(=NH)NHCbz |
| benzylsulfonyl | D-leucyl | L-prolyl | -NH-CH2-C6H4-C(=NH)NH2 |
| benzoyl | D-leucyl | L-prolyl | -NH-CH2-C6H4-C(=NH)NH2 |
| phenylacetyl | D-leucyl | L-prolyl | -NH-CH2-C6H4-C(=NH)NH2 |
| p-methoxyphenylacetyl | D-leucyl | L-prolyl | -NH-CH2-C6H4-C(=NH)NH2 |
| carboxylmethyl | D-leucyl | L-prolyl | -NH-CH2-C6H4-C(=NH)NH2 |

-continued

| A | D | E | F-G |
|---|---|---|---|
| benzenesulfonyl | D-leucyl | L-prolyl | 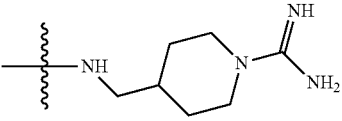 [SMILES: *NCC1CCN(C(=N)N)CC1] |
| benzenesulfonyl | D-leucyl | L-prolyl | 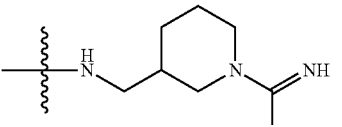 |
| benzenesulfonyl | D-leucyl | L-prolyl | 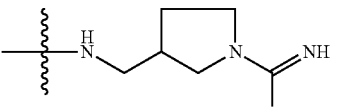 |
| benzoyl | D-isoleucyl | L-prolyl | 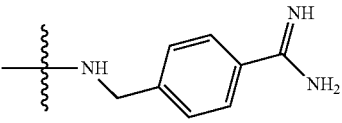 [SMILES: *NCc1ccc(C(=N)N)cc1] |
| benzylsulfonyl | D-leucyl | L-prolyl | 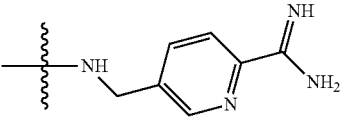 [SMILES: *NCc1ccc(C(=N)N)nc1] |
| benzenesulfonyl | D-leucyl | L-prolyl | 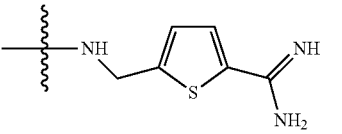 [SMILES: *NCc1ccc(C(=N)N)s1] |
| benzylsulfonyl | D-leucyl | L-prolyl | 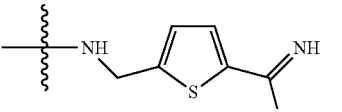 |
| carboxylmethyl | D-leucyl | L-prolyl | 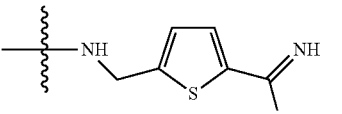 |
| benzenesulfonyl | D-leucyl | 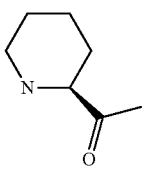 | 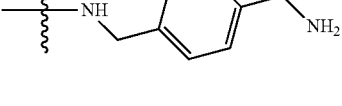 |
| benzenesulfonyl | D-leucyl | 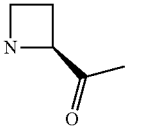 | 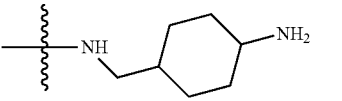 |
| benzenesulfonyl | D-leucyl | L-prolyl |  |

-continued

| A | D | E | F-G |
|---|---|---|---|
| benzenesulfonyl | D-leucyl | L-prolyl | 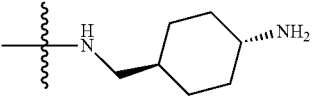 [SMILES: *NC[C@H]1CC[C@H](N)CC1] |
| benzylsulfonyl | D-leucyl | L-prolyl | 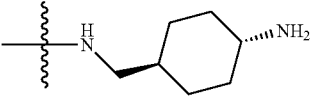 [SMILES: *NC[C@H]1CC[C@H](N)CC1] |
| benzenesulfonyl | D-leucyl | L-prolyl | 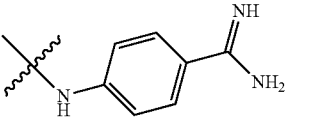 [SMILES: *Nc1ccc(C(=N)N)cc1] |
| benzenesulfonyl | D-leucyl | L-prolyl | 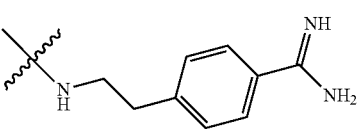 [SMILES: *NCCc1ccc(C(=N)N)cc1] |
| benzenesulfonyl | D-leucyl | L-prolyl | 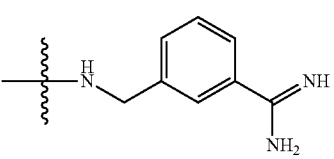 [SMILES: *NCc1cccc(C(=N)N)c1] |
| benzenesulfonyl | D-leucyl | L-prolyl | 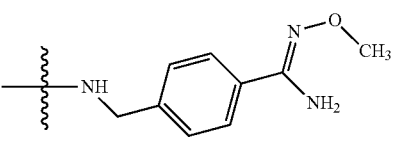 [SMILES: *NCc1ccc(/C(N)=N/OC)cc1] |
| benzenesulfonyl | D-leucyl | L-prolyl | 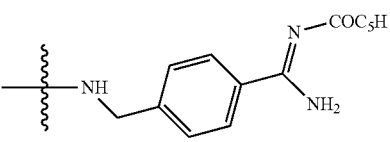 |
| benzenesulfonyl | D-leucyl | L-prolyl | 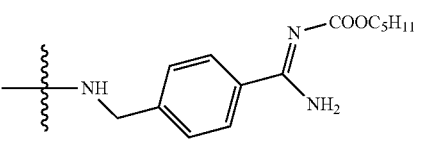 |
| benzenesulfonyl | D-leucyl | L-prolyl | 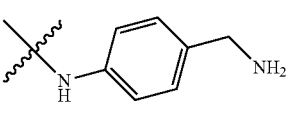 [SMILES: *Nc1ccc(CN)cc1] |
| benzenesulfonyl | D-leucyl | L-prolyl | 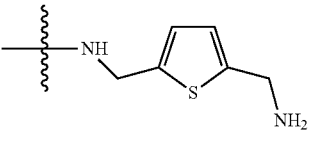 [SMILES: *NCc1ccc(CN)s1] |
| p-toluenesulfonyl | D-leucyl | L-prolyl | 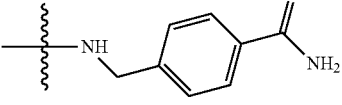 |

-continued

| A | D | E | F-G |
|---|---|---|---|
| p-tert-butylbenzenesulfonyl | D-leucyl | L-prolyl | 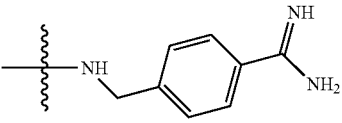 |
| p-fluorobenzenesulfonyl | D-leucyl | L-prolyl | 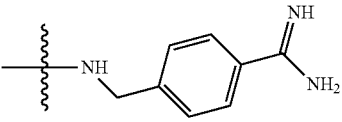 [SMILES: *NCc1ccc(C(=N)N)cc1] |
| p-bromobenzenesulfonyl | D-leucyl | L-prolyl | 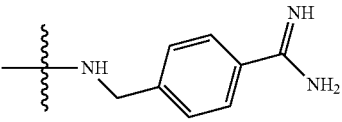 [SMILES: *NCc1ccc(C(=N)N)cc1] |
| p-acetylaminobenzenesulfonyl | D-leucyl | L-prolyl | 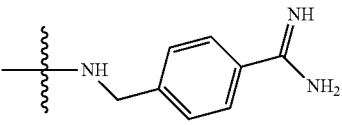 [SMILES: *NCc1ccc(C(=N)N)cc1] |
| N-1-naphthalenylsulfonyl | D-leucyl | L-prolyl | 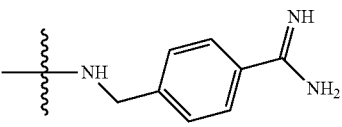 [SMILES: *NCc1ccc(C(=N)N)cc1] |
| N-2-naphthalenylsulfonyl | D-leucyl | L-prolyl | 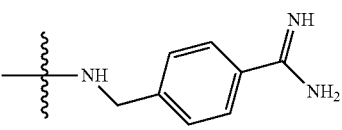 [SMILES: *NCc1ccc(C(=N)N)cc1] |
| dimethylaminosulfonyl | D-leucyl | L-prolyl | 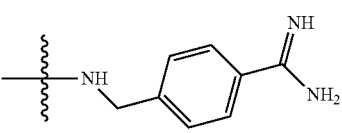 [SMILES: *NCc1ccc(C(=N)N)cc1] |
| methanesulfonyl | D-leucyl | L-prolyl | 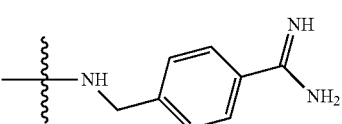 |
| ethanesulfonyl | D-leucyl | L-prolyl | 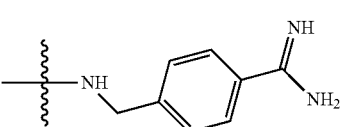 |
| cyclopropanesulfonyl chloride | D-leucyl | L-prolyl |  |
| t-butyloxycarbonyl | D-leucyl | L-prolyl |  |

-continued

| A | D | E | F-G |
|---|---|---|---|
| methoxycarbonyl | D-leucyl | L-prolyl | 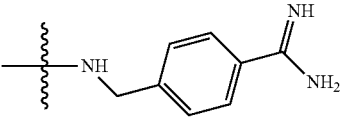 [SMILES: *NCc1ccc(C(=N)N)cc1] |
| carboxylethyl | D-leucyl | L-prolyl | 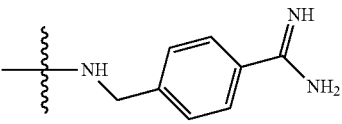 [SMILES: *NCc1ccc(C(=N)N)cc1] |

Among these compounds, the particularly preferable compounds are:

| A | D | E | F-G |
|---|---|---|---|
| benzenesulfonyl | D-leucyl | L-prolyl | 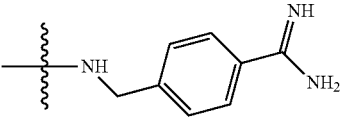 [SMILES: *NCc1ccc(C(=N)N)cc1] |
| benzylsulfonyl | D-leucyl | L-prolyl | 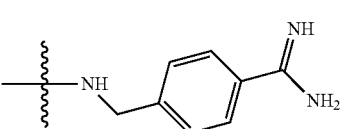 |
| benzoyl | D-leucyl | L-prolyl | 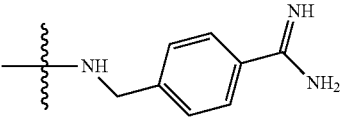 |
| phenylacetyl | D-leucyl | L-prolyl | 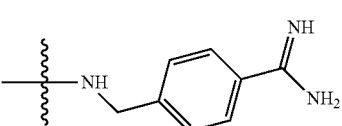 |
| p-methoxyphenylacetyl | D-leucyl | L-prolyl | 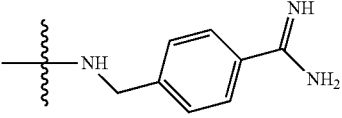 [SMILES: *NCc1ccc(C(=N)N)cc1] |
| carboxylmethyl | D-leucyl | L-prolyl |  |
| benzenesulfonyl | D-leucyl | L-prolyl | 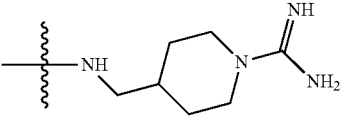 [SMILES: *NCC1CCN(C(=N)N)CC1] |
| benzenesulfonyl | D-leucyl | L-prolyl | 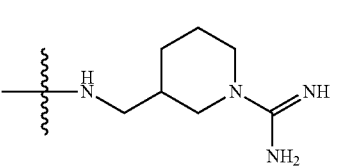 [SMILES: *NCC1CCCN(C(=N)N)C1] |

-continued

| A | D | E | F-G |
|---|---|---|---|
| benzenesulfonyl | D-leucyl | L-prolyl | pyrrolidinylmethyl-NH- with guanidine (C(=NH)NH₂) on ring N |
| benzoyl | D-isoleucyl | L-prolyl | -NH-CH₂-(4-benzamidine) |
| benzylsulfonyl | D-leucyl | L-prolyl | -NH-CH₂-(5-pyridine-2-carboxamidine) |
| benzenesulfonyl | D-leucyl | L-prolyl | -NH-CH₂-(5-thiophene-2-carboxamidine) |
| benzylsulfonyl | D-leucyl | L-prolyl | -NH-CH₂-(5-thiophene-2-carboxamidine) |
| carboxylmethyl | D-leucyl | L-prolyl | -NH-CH₂-(5-thiophene-2-carboxamidine) |
| benzenesulfonyl | D-leucyl | 2-acetyl-piperidinyl | -NH-CH₂-(4-benzamidine) |
| benzenesulfonyl | D-leucyl | 2-acetyl-azetidinyl | -NH-CH₂-(4-benzamidine) |
| benzenesulfonyl | D-leucyl | L-prolyl | -NH-CH₂-(4-aminocyclohexyl) |
| benzylsulfonyl | D-leucyl | L-prolyl | -NH-CH₂-(4-aminocyclohexyl) |
| benzenesulfonyl | D-leucyl | L-prolyl | -NH-(4-benzamidine) |

-continued

| A | D | E | F-G |
|---|---|---|---|
| benzenesulfonyl | D-leucyl | L-prolyl | ~~~NH-CH2CH2-C6H4-C(=NH)NH2 (para) |
| benzenesulfonyl | D-leucyl | L-prolyl | ~~~NH-CH2-C6H4-C(=NH)NH2 (meta) |
| benzenesulfonyl | D-leucyl | L-prolyl | ~~~NH-CH2-C6H4-C(=N-OCH3)NH2 (para) |
| benzenesulfonyl | D-leucyl | L-prolyl | ~~~NH-CH2-C6H4-C(=N-COC5H11)NH2 (para) |
| benzenesulfonyl | D-leucyl | L-prolyl | ~~~NH-CH2-C6H4-C(=N-COOC5H11)NH2 (para) |
| benzenesulfonyl | D-leucyl | L-prolyl | ~~~NH-C6H4-CH2-NH2 (para) |
| benzenesulfonyl | D-leucyl | L-prolyl | ~~~NH-CH2-(thiophene-2,5-diyl)-CH2-NH2 |
| p-toluenesulfonyl | D-leucyl | L-prolyl | ~~~NH-CH2-C6H4-C(=NH)NH2 (para) |
| p-tert-butylbenzenesulfonyl | D-leucyl | L-prolyl | ~~~NH-CH2-C6H4-C(=NH)NH2 (para) |
| p-fluorobenzenesulfonyl | D-leucyl | L-prolyl | ~~~NH-CH2-C6H4-C(=NH)NH2 (para) |
| p-bromobenzenesulfonyl | D-leucyl | L-prolyl | ~~~NH-CH2-C6H4-C(=NH)NH2 (para) |

| A | D | E | F-G |
|---|---|---|---|
| p-acetylaminobenzenesulfonyl | D-leucyl | L-prolyl | 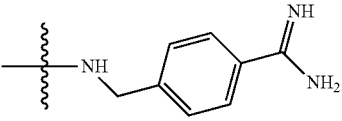 |
| N-1-naphthalenylsulfonyl | D-leucyl | L-prolyl | 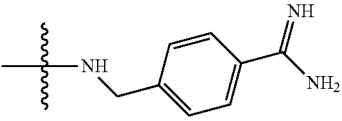 [SMILES: *NCc1ccc(C(=N)N)cc1] |
| N-2-naphthalenylsulfonyl | D-leucyl | L-prolyl | 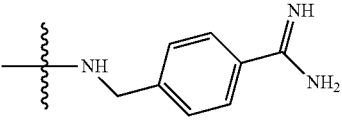 [SMILES: *NCc1ccc(C(=N)N)cc1] |
| dimethylaminosulfonyl | D-leucyl | L-prolyl | 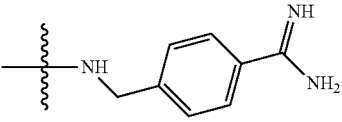 |
| methanesulfonyl | D-leucyl | L-prolyl | 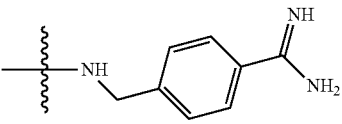 [SMILES: *NCc1ccc(C(=N)N)cc1] |
| ethanesulfonyl | D-leucyl | L-prolyl | 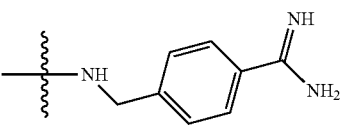 [SMILES: *NCc1ccc(C(=N)N)cc1] |
| cyclopropanesulfonyl chloride | D-leucyl | L-prolyl | 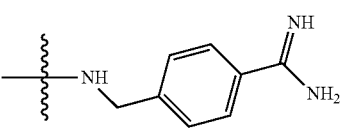 [SMILES: *NCc1ccc(C(=N)N)cc1] |
| t-butyloxycarbonyl | D-leucyl | L-prolyl | 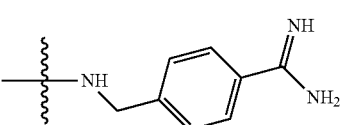 |
| methoxycarbonyl | D-leucyl | L-prolyl | 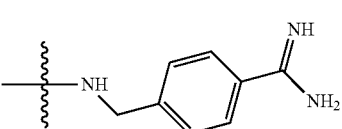 |
| carboxylethyl | D-leucyl | L-prolyl |  |

The present invention also includes pharmaceutically acceptable salt and pharmaceutically acceptable prodrug thereof.

The compound of formula (I) of the present invention can be used for mediating the activity of trypsin-like serine proteases. More specifically, the compound of the present invention can be used as an anticoagulant and a medicament for modulating or inhibiting the activity of trypsin-like serine proteases, thereby treating thrombosis and other cardiovascular diseases.

Unless otherwise stated, terms and abbreviations used in the present invention present the standard meaning thereof.

The pharmaceutically acceptable salts of the compound of formula (I) include the salts derived from the pharmaceutically acceptable inorganic acid and organic acid. The examples of suitable acid include sulfuric acid, sulfurous acid, hydrochloric acid, acetic acid, hydrobromic acid, nitric acid, phosphoric acid, metaphosphoric acid, pyrophosphoric acid, maleic acid, fumaric acid, succinic acid, citric acid, perchloric acid, p-toluenesulfonic acid, tartaric acid, formic acid, acetic acid, propanoic acid, heptylic acid, oxalic acid, benzoic acid, propandioic acid, succinic acid, succinic acid, cis-butenedioic acid, hydroxy-butanoic acid, citric acid, methanesulfonic acid, benzenesulfonic acid, lactic acid or mandelic acid.

Because the compound of formula (I) of the present invention has one or more chiral carbon atoms in its structure, it can also exist in the form of racemate, mixture of diastereomers and pure enantiomers, and all of these isomers are included in the scope of the present invention.

The present invention also relates to the pharmaceutically acceptable prodrug of the compound of the general formula, which can be metabolized into active compound after its administration. For example, suitable prodrugs are derivatives of the formula in which N-alkoxycarbonyl is protected or carboxylic acid is protected by ester.

The second objective of the present invention is to provide a method for the preparation of the compound of formula (I), including the step of making the final product from the raw material of amino acid protected by protective group at nitrogen position. The similarly standard chemical preparation reactions (the compound of the present invention can be prepared according to several general processes hereinafter) known in the art can be used in the method, and the starting materials, reagents, techniques and methods used in the schemes are well known and understandable to those of ordinary skill in the art.

The compound of the present invention can be prepared according to the following general process:

As exemplified in Example 2 (scheme 1), an amino acid is reacted with an acylation reagent and a base, the resulting acid is coupled with the benzyl ester of the amino acid, and then hydrogenated to remove the benzyl, the resulting acid is coupled to the desired amine such as p-aminomethyl cyanophenyl. The coupled product is converted into amidine by another two steps comprising the reaction with hydroxylamine hydrochloride and the hydrogenation reaction.

Scheme 1:

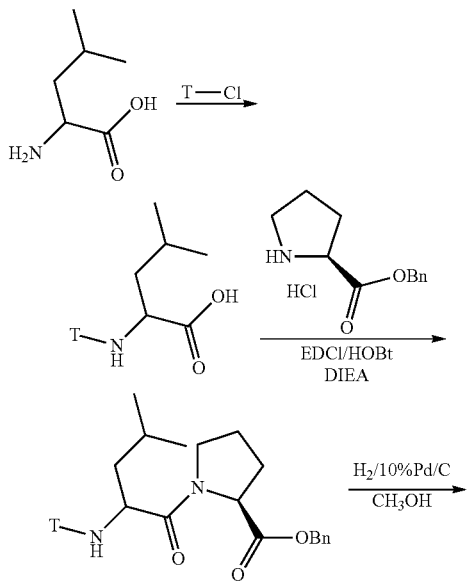

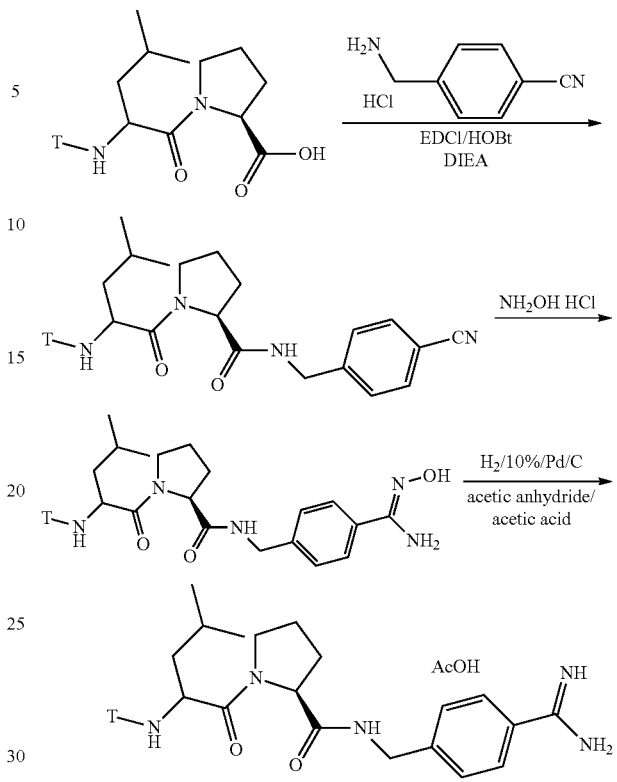

Another alternative synthetic route is shown in scheme 2: the protected amino acid such as N-t-butyloxycarbonyl-D-isoleucine is coupled to proline benzyl ester using condensation agents such as EDCI/HOBt. The resulting dipeptide is treated with strong acid such as hydrochloric acid and the like to remove the t-butyloxycarbonyl protective agent. The resulting amine is reacted with an acylation reagent and a base, and then hydrogenated to remove benzyl, the resulting acid is coupled to the desired amine such as p-aminomethyl cyanophenyl. The coupled product is converted into amidine by another two steps comprising the reaction with hydroxylamine hydrochloride and the hydrogenation reaction.

Scheme 2:

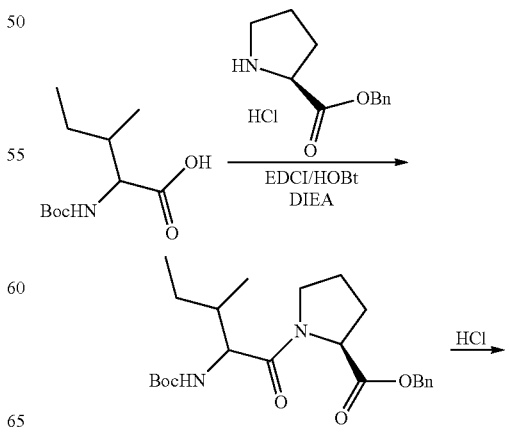

33
-continued

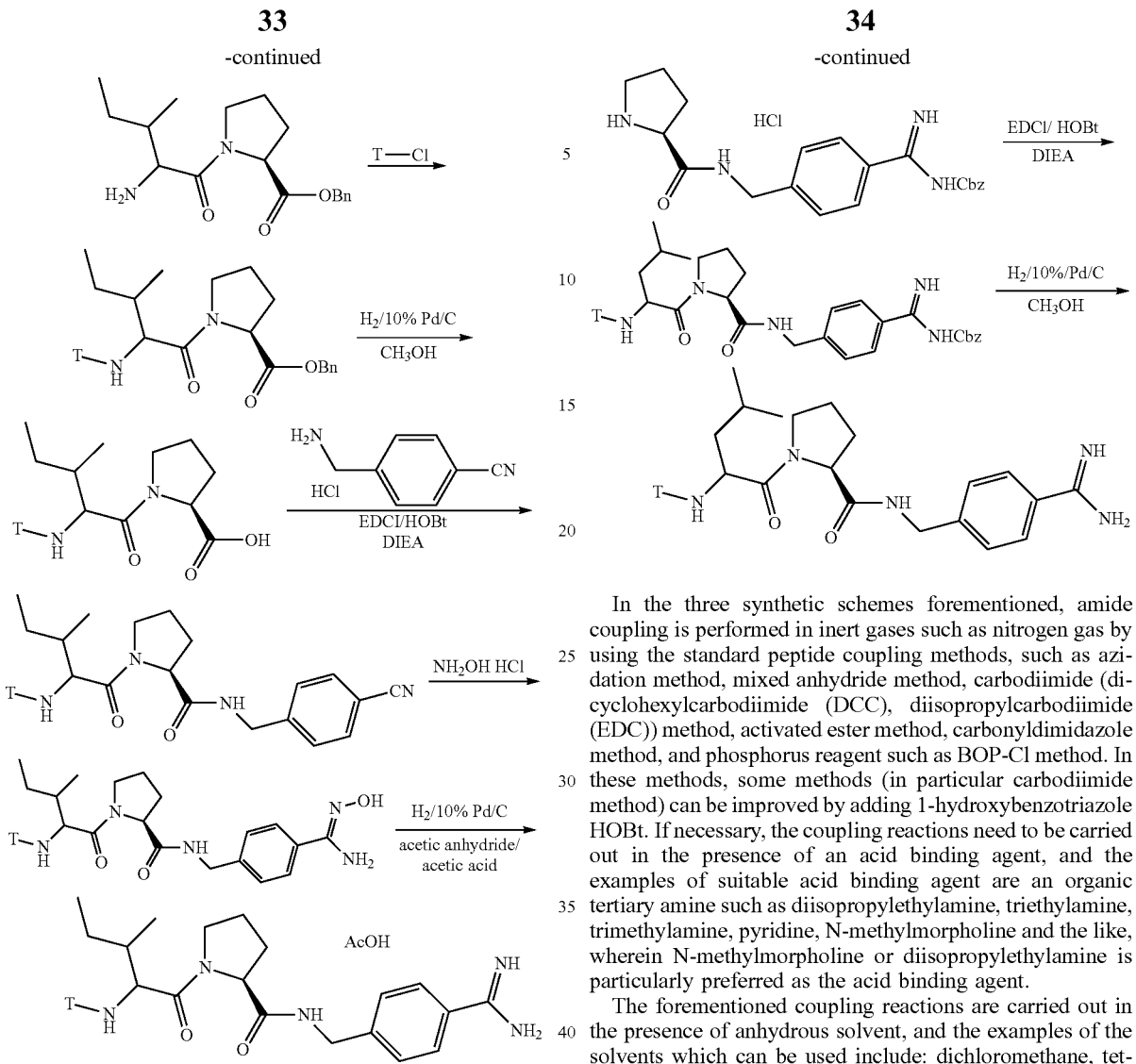

A further alternative synthetic route is shown in route 3: an amino acid substituted at nitrogen position is coupled to the desired amine using a condensation agent such as EDCI/HOBt. Then the coupled product is converted into amidine by hydrogenolysis reaction to remove the protective group.

Scheme 3:

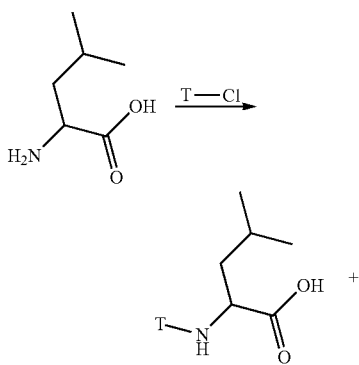

34
-continued

In the three synthetic schemes forementioned, amide coupling is performed in inert gases such as nitrogen gas by using the standard peptide coupling methods, such as azidation method, mixed anhydride method, carbodiimide (dicyclohexylcarbodiimide (DCC), diisopropylcarbodiimide (EDC)) method, activated ester method, carbonyldimidazole method, and phosphorus reagent such as BOP-Cl method. In these methods, some methods (in particular carbodiimide method) can be improved by adding 1-hydroxybenzotriazole HOBt. If necessary, the coupling reactions need to be carried out in the presence of an acid binding agent, and the examples of suitable acid binding agent are an organic tertiary amine such as diisopropylethylamine, triethylamine, trimethylamine, pyridine, N-methylmorpholine and the like, wherein N-methylmorpholine or diisopropylethylamine is particularly preferred as the acid binding agent.

The forementioned coupling reactions are carried out in the presence of anhydrous solvent, and the examples of the solvents which can be used include: dichloromethane, tetrahydrofuran, aether, acetonitrile, dichloroethane, ethyl acetate, N,N-dimethyl formamide, and dimethyl sulfoxide. The reaction temperature is usually unimportant, and it is preferable to react at 0-30° C. for 2-24 hours.

The methods to remove the amino-protective group are carried out through conventional methods, for example, hydrolysis in the presence of an acid (for example: organic acid such as trifluoroacetic acid, benzenesulfonic acid, formic acid and the like, or inorganic acid such as hydrochloric acid, sulfuric acid, hydrobromic acid and the like), or hydrolysis in the presence of a base (for example: hydroxide, hydride, carbonate or hydrocarbonate of alkali metal or alkaline earth metal, such as sodium hydroxide, potassium hydroxide, sodium hydride, potassium carbonate, sodium hydrogencarbonate and the like, or organic base such as diisopropylethylamine, triethylamine, piperidine and the like), or hydrogenolysis reduction performed by using hydrogen gas in the presence of a catalyst (metal catalyst such as palladium, platinum, nickel and the like). Suitable methods can be found in "Protective groups in organic synthesis", 3$^{rd}$ Edition, by T. W. Green and Peter G. M. Wuts (1999), published by John Wiley&Sons, Inc.

In general, the reaction can be carried out in the presence of solvents having no adverse effects on the reaction, and the examples of the solvents which can be used include: dichloromethane, alcohols such as methanol, ethanol and the like, tetrahydrofuran, dioxane, acetone, acetic acid, and ethyl acetate. The reaction temperature is usually unimportant, and 0-40° C. is preferable.

The methods to remove the protective group for carboxylic acid are generally carried out through conventional methods, for example, hydrolysis in the presence of a base (for example: hydroxide, hydride, carbonate or hydrocarbonate of alkali metal or alkaline earth metal, such as sodium hydroxide, potassium hydroxide, sodium hydride, potassium carbonate, sodium hydrogencarbonate and the like, or organic base such as diisopropylethylamine, triethylamine and the like), or reduction performed by using hydrogen gas in the presence of catalyst (metal catalysts such as palladium, platinum, nickel and the like). Suitable methods can be found in "Protective groups in organic synthesis", $3^{rd}$ Edition, by T. W. Green and Peter G. M. Wuts (1999), published by John Wiley&Sons, Inc.

In general, the reaction can be carried out in the presence of solvents having no adverse effects on the reaction, and the examples of the solvents which can be used include: water, alcohols such as methanol, ethanol and the like, tetrahydrofuran, dioxane, and acetone. The reaction temperature is usually unimportant, and 0-30° C. is preferable.

The reductive amination method and the nucleophilic substitution method can be used in the alkylation reaction on N. For example, the mucleophilic substitution method is used. Suitable nucleophilic reagents include, but not limited to: alkyl bromide, alkyl iodide, alkyl chloride, alkyl sulfonate, alkyl benzene sulfonate, alkyl p-toluenesulfonate, alkyl methanesulfonate or reagents containing acidic sulfate radical such as methyl sulfate radical. Alkyl iodide or alkyl p-toluenesulfonate is preferable. The nucleophilic substitution reaction needs to be carried out in the presence of an acid binding agent, and suitable acid binding agents can be an inorganic base (hydroxide, hydride, carbonate, hydrocarbonate, hydrophosphate of alkali metal or alkaline earth metal, such as sodium hydroxide, sodium hydride, potassium carbonate, dipotassium hydrogen phosphate and the like), or an organic base such as diisopropylethylamine, triethylamine, piperidine and the like. The examples are organic tertiary amine such as diisopropylethylamine, triethylamine, trimethylamine, trimethylamine, pyridine, N-methylmorpholine and the like, and dipotassium hydrogen phosphate or diisopropylethylamine is particularly preferred as the acid binding agent. The examples of the solvents which can be used include: tetrahydrofuran, dioxane, acetonitrile, acetone, N,N-dimethyl formamide and the like. The reaction temperature is preferably 30-80° C.

For example, the reductive amination method is used. The reactants and corresponding aldehyde can be treated with a reducing agent in a suitable solvent. Suitable reducing agents are well known in the art, which include but not limited to tri-t-butoxy lithium, potassium borohydride, sodium borohydride, sodium triacetoxyborohydride, Raney's nickel, lithium triethylborohydride, wherein potassium borohydride or sodium triacetoxyborohydride is preferable. Suitable solvents in which the reductive amination reaction is carried out are known in the art, such as methanol, ethanol, tetrahydrofuran, dichloroethane, acetonitrile and mixed solvent and the like. The reaction temperature is preferably 0-50° C.

The products in each step can be purified with the methods known in the art such as column chromatography and recrystallization.

The third objective of the present invention is to provide the use of the compound of formula (I) for inhibiting thrombin, as well as treating and preventing thrombin mediated and thrombin related diseases.

The compound of the present invention can be used for treating and preventing thrombin mediated and thrombin related diseases. The diseases include, but not limited to: venous thrombosis and pulmonary embolism, arterial thrombosis such as myocardial ischemia, myocardial infarction, unstable angina pectoris, apoplexy caused by thrombosis and peripheral artery thrombosis; atherosclerosis diseases such as coronary artery disease, cerebral arteries disease or peripheral arteriopathy.

The compound of the present invention can also serve as an anticoagulant in the blood channels in vitro.

In addition, such compounds are expected to be used together with thrombolytic agents for preventing and treating cardiac infarction. Furthermore, such compounds are expected to be used for preventing the reformation of thrombosis after a microsurgery. Such compounds have an expected efficacy on the anticoagulant therapy of haemodialysis and disseminated intravascular coagulation. Such compounds can also be used for in vitro storage of blood, blood plasma and other blood products.

The compound of the present invention is expected to be administered by orally or parenteral routes such as intravenous infusion, intramuscular injection, or hypodermic injection. The specific dose of the compound according to the administration of the present invention to obtain the effect of treatment and prevention depends on the particular situation of the case, including the form of administration, the speed of administration and the diseases to be treated. Typical daily doses of oral administration to obtain the effect are between about 0.01 mg/kg and about 1000 mg/kg; and typical daily doses of parenteral administration are between about 0.001 mg/kg and about 100 mg/kg. The method of administrating doses can vary, for example, which can be a single dose per day, or multiple doses such as 3-5 times per day may also be suitable. Obviously, it is possible to make necessary general adjustment for administration dose and administration route according to age and body weight of the subject as well as severity of the disease to be treated. Precise dose and route of administration should be determined by the physician.

The fourth objective of the present invention is to provide a pharmaceutical composition, which comprises the compound of formula (I) and a pharmaceutically acceptable carrier.

The compound of the present invention can be administered in the form of pharmaceutical compositions. For example, for oral administration, the compound is formulated into a form of a capsule or a tablet, which may contain the excipients such as lubricant, adhesive, disintegrating agent. For injection use, the compound is dissolved in pharmaceutically acceptable solvents such as sterile pyrogen-free water, and normal saline.

The dosage form can be solid, semisolid or liquid formulation formulated by known techniques. The content of the active ingredient in such compositions is 0.1%-99.9%, based on the weight of the formulation. Moreover, the carriers, diluents or excipients used in the composition are compatible with the active ingredient and harmless for the received subject.

The abbreviations that appear in the application are as follows:
Boc: t-butyloxycarbonyl
Cbz: benzyloxycarbonyl
DCHA: dicyclohexylamine
Leu: leucine Ile: isoleucine Pro: prolyl Hpro: homoprolyl DIEA: diisopropylethylamine EDCI: 1-ethyl-3-(3-dimethylaminopropyl) carbodiimide hydrochloride HOBt: 1-hydroxybenzotriazole TFA: trifluoroacetic acid AcOH: acetic acid DMF: N,N'-dimethyl formamide.

Determination of Activity

The in vitro inhibitory activity against thrombin of the compound of the present invention can be determined by chromogenic substrate method. In the test, the activity of inhibiting human alpha-thrombin is determined by using S2238 as the colour development substrate, and its $IC_{50}$ value is calculated.

EXAMPLES

The following examples are to describe in detail the specific synthetic method shown in the Schemes 1 and 2, wherein the preferable compounds of the present invention are synthesized. However, it is understood for the technician that the chemical reactions can be changed slightly to prepare a lot of other thrombin inhibitors of the present invention. For example, compounds not exemplified in the present invention can be successfully synthesized through the improvement obvious to those skilled in the art. These examples are only used for illustration, but not to limit the scope of the present invention in any way.

Detection Method:

Varian INOVA-400 nuclear magnetic resonance apparatus is used, wherein tetramethylsilane is the internal standard, and the unit of chemical shift (δ) is ppm. Thinlayer chromatography (TLC, using HSG-F254 high performance silica gel prefabricated panel for thin chromatography, made in Yantai Zhifu Huangwu silica gel development and pilot plant) and HPLC is used for detecting the reaction and the purity of the product. Iodine vapour or irradiation with 254A and 310A ultraviolet lamp or 1% ninhydrin solution in ethanol is used for colour development. Unless specially stated, all the reagents used are analytically pure, and anhydrous solvent and reagents are treated according to conventional methods. The melting point is determined by micrographic melting point apparatus, and the thermometer used is non-corrected.

HPLC: Waters 1525; detector: Waters 2487; chromatographic column: Phenomenex C18 (4.6×250 mm, 5 μm); detection wavelength: 220 nm and 254 nm; column temperature: 40° C.; flow rate: 1.0 ml/min;

Mobile Phase 1:

A: 0.1% trifluoroacetic acid aqueous solution, B: acetonitrile

Mobile Phase 2:

A: triethylamine phosphate buffer solution, pH 2.0, B: acetonitrile

Mobile Phase 3:

A: phosphate buffer, pH 8.0, B: acetonitrile

Method 1: mobile phase A from 75% to 25%, gradient elution for 10 minutes

Method 2: mobile phase A from 95% to 30%, gradient elution for 20 minutes

Example 1

Synthesis of N-benzenesulfonyl-D,L-leucyl-L-prolyl-{[4-(N'-hydroxyl) amidinophenyl]methyl}amide a) Preparation of N-benzenesulfonyl-D,L-leucine D,L-leucine (2 g) was dissolved in 1.5N sodium hydroxide solution (10 ml), dioxane (15 ml) was added, and cooled down to control the temperature between 0 and 5° C.; benzenesulfonyl chloride (3 g) and 1.5N sodium hydroxide solution were slowly added dropwisely to maintain the pH at 9-10; the resulting mixture was allowed to react at 0° C. for 2 h and warm up naturally to room temperature to react for 2 h. Upon cooled, dilute hydrochloric acid was added dropwisely to adjust pH to 3, the resulting mixture was concentrated under reduced pressure to remove dioxane, and a great quantity of solid precipitated out; filtered, the solid obtained was recrystallized with ethyl acetate/petroleum ether to give 3.7 g white solid. The content was 99% (HPLC, mobile phase 1, method 2).

Rf=0.8

Developer: n-butyl alcohol:water:acetic acid:ethyl acetate=1:1:1:1

Color development: ultraviolet, iodine and 1% ninhydrin solution

1H NMR (CDCl$_3$+D$_2$O) δ ppm: 0.845-0.861 (3H, d), 0.912-0.929 (3H, d), 1.514-1.562 (2H, m), 1.732-1.785 (1H, m), 3.942-4.003 (1H, m), 7.492-7.888 (5H, m)

b) Preparation of N-benzenesulfonyl-D,L-leucyl-L-proline benzyl ester

N-benzenesulfonyl-D,L-leucine (2.7 g) and L-proline benzyl ester (2.7 g) were dissolved in dichloromethane (50 ml), DIEA (3.1 g) was added dropwisely under the protection of nitrogen upon cooled. HOBt (1.4 g) and EDCI (2.6 g) were added after the completion of addition, and the resulting mixture was allowed to warm up naturally to room temperature to react for 4 h, and then concentrated under reduced pressure to remove the reaction liquid, and purified directly on a column to give 3.8 g white solid (82%), with the content being 98% (HPLC, mobile phase 1, method 1).

Rf=0.3

Developer: petroleum ether:ethyl acetate=2:1

Color development: ultraviolet, iodine and 1% ninhydrin solution

1H NMR (CDCl$_3$+D$_2$O) δ ppm: 0.921-0.950 (6H, m), 1.223-1.529 (3H, m), 1.719-2.078 (4H, m), 3.105-3.494 (2H, m), 3.816-3.963 (1H, m), 4.418-4.597 (1H, m), 5.122 (2H, s), 7.281-7.854 (10H, m)

c) Preparation of N-benzenesulfonyl-D,L-leucyl-L-proline

N-benzenesulfonyl-D,L-leucyl-L-proline benzyl ester (2 g) was dissolved in methanol (40 ml), and 10% palladium-carbon (200 mg) was added. The resulting mixture aerated with hydrogen was allowed to react at room temperature for 3 h, filtered and concentrated under reduced pressure to remove the solvent to give a white foam-like solid (1.6 g, 99%), which was directly used for the next reaction.

d) Preparation of N-benzenesulfonyl-D,L-leucyl-L-proline-[(4-cyanophenyl)methyl]amide N-benzenesulfonyl-D,L-leucyl-L-proline (921 mg), p-aminomethyl cyanophenyl hydrochloride (464 mg) and DIEA (742 mg) were dissolved in anhydrous dichloromethane (20 ml), and cooled down to 0° C. under the protection of nitrogen, and then HOBt (338 mg) and EDCI (575 mg) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 1.5 g crude product, which was purified with column chromatography to give a colourless oil (1.06 g, yield: 87%).

Rf=0.4
Developer: petroleum ether:ethyl acetate=1:1
Color development: ultraviolet and iodine
MS: 505 (M+Na$^+$)
1H NMR (CDCl$_3$+D$_2$O) δ ppm: 0.860-0.922 (6H, m), 1.603-1.673 (1H, m), 1.795-1.878 (1H, m), 2.047-2.408 (4H, m), 3.233-3.296 (1H, m), 3.373-3.418 (1H, m), 3.968-4.106 (1H, m), 4.123-4.160 (1H, m), 4.321-4.619 (3H, m), 7.284-7.862 (6H, m)

e) Preparation of N-benzenesulfonyl-D,L-leucyl-L-prolyl-{[4-(N'-hydroxyl) amidinophenyl]methyl}amide The product (1.01 g) obtained in the above step was dissolved in water/ethanol (20 ml/20 ml), hydroxylamine hydrochloride and sodium carbonate were added under the protection of nitrogen, and the resulting mixture was allowed to react under reflux for 2 hours, cooled down, concentrated under reduced pressure to remove the solvent, and purified on a column to give a white foam-like solid (978 mg, 90.7%).

Rf=0.1
Developer: petroleum ether:ethyl acetate=1:1
Color development: ultraviolet and 1% ninhydrin solution
MS: 516 (M+H)

Example 2

Preparation of N-benzenesulfonyl-D,L-leucyl-L-prolyl-[(4-amidinophenyl)methyl]amide acetate The compound obtained in the Example 1 was dissolved in acetic acid (7 ml), acetic anhydride (277 mg) and 10% palladium-carbon (150 mg) were added, and the resulting mixture aerated with hydrogen was allowed to react for 24 hours, filtered and concentrated under reduced pressure to remove the solvent, aether (20 ml) was added, and then the resulting mixture was placed in the refrigerator over night, and the solid precipitated out, which was filtered and dried (250 mg, 66%).

MS: 560 (M+H)

Example 3

N-Benzylsulfonyl-D,L-leucyl-L-prolyl-{[4-(N'-hydroxyl) amidinophenyl]methyl}amide a) Preparation of N-benzylsulfonyl-D,L-leucine

D,L-leucine (2 g) was dissolved in 1.5N sodium hydroxide solution (10 ml), dioxane (15 ml) was added, and cooled down to control the temperature between 0 and 5° C.; benzylsulfonyl chloride (3.2 g) and 1.5N sodium hydroxide solution were slowly added dropwisely to maintain the pH at 9-10; the resulting mixture was allowed to react at 0° C. for 2 h and warm up naturally to room temperature to react for 2 h. Upon cooled, dilute hydrochloric acid was added dropwisely to adjust pH to 3, and the resulting mixture was concentrated under reduced pressure to remove dioxane, and a great quantity of solid precipitated out; filtered, the solid obtained was recrystallized with ethyl acetate/petroleum ether to give 3.5 g white solid. The content was 99% (HPLC, mobile phase 1, method 2).

Rf=0.8
Developer: n-butyl alcohol:water:acetic acid:ethyl acetate=1:1:1:1
Color development: ultraviolet, iodine and 1% ninhydrin solution
MS: 308 (M+Na)

b) Preparation of N-benzylsulfonyl-D,L-leucyl-L-proline benzyl ester

N-benzylsulfonyl-D,L-leucine (4.3 g) and L-proline benzyl ester (4.1 g) were dissolved in dichloromethane (50 ml), DIEA (4.7 g) was added dropwisely under the protection of nitrogen upon cooled, HOBt (2 g) and EDCI (3.8 g) were added after the completion of addition, and the resulting mixture was allowed to warm up naturally to room temperature to react for 4 h, concentrated under reduced pressure to remove the reaction liquid, and purified directly on a column to give 5.3 g white foam-like solid (74.8%), with the content being 98% (HPLC, mobile phase 1, method 1).

Rf=0.5
Developer: petroleum ether:ethyl acetate=2:1
Color development: ultraviolet, iodine and 1% ninhydrin solution
MS: 473 (M+H)

c) Preparation of N-benzylsulfonyl-D,L-leucyl-L-proline

N-benzylsulfonyl-D,L-leucyl-L-proline benzyl ester (1.2 g) was dissolved in methanol (20 ml), and 10% palladium-carbon (120 mg) was added. The resulting mixture aerated with hydrogen was allowed to react at room temperature for 3 h, filtered and concentrated under reduced pressure to remove the solvent to give a white foam-like solid (1 g, 99%), which was directly used for the next reaction.

d) Preparation of N-benzylsulfonyl-D,L-leucyl-L-proline-[(4-cyanophenyl)methyl]amide N-benzylsulfonyl-D,L-leucyl-L-proline (1 g), p-aminomethyl cyanophenyl hydrochloride (464 mg) and DIEA (742 mg) were dissolved in anhydrous dichloromethane (20 ml), cooled down to 0° C. under the protection of nitrogen, and then HOBt (338 mg) and EDCI (575 mg) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 1.5 g crude product, which was purified with column chromatography to give a colourless oil (905 mg, yield: 80%).
Rf=0.4
Developer: petroleum ether:ethyl acetate=1:1
Color development: ultraviolet and iodine
MS: 519 (M+H)

e) Preparation of N-benzylsulfonyl-D,L-leucyl-L-prolyl-{[4-(N'-hydroxyl)amidinophenyl]methyl}amide The product (905 mg) obtained in the above step was dissolved in water/ethanol (20 ml/20 ml), hydroxylamine hydrochloride and sodium carbonate were added under the protection of nitrogen, the resulting mixture was allowed to react under reflux for 2 hours, and cooled down, concentrated under reduced pressure to remove the solvent, and purified with a column to give a white foam-like solid (871 mg, 87.7%).
Rf=0.1
Developer: petroleum ether:ethyl acetate=1:1
Color development: ultraviolet and 1% ninhydrin solution
MS: 530 (M+H)

Example 4

N-benzylsulfonyl-D,L-leucyl-L-prolyl-{[4-(N'-hydroxyl) amidinophenyl]methyl}amide acetate The compound obtained in the Example 3 was dissolved in acetic acid (7 ml), acetic anhydride (270 mg) and 10% palladium-carbon (140 mg) were added, and the resulting mixture aerated with hydrogen were allowed to react for 24 hours, filtered and concentrated under reduced pressure to remove the solvent, aether (20 ml) was added, and then the resulting mixture was placed in the refrigerator over night, and the solid precipitated out, which was filtered and dried (540 mg, 62.7%).
MS: 514 (M+1)

Example 5

N-benzoyl-D,L-leucyl-L-prolyl-{[4-(N'-hydroxyl) amidinophenyl]methyl}amide a) Preparation of N-benzoyl-D,L-leucine D,L-leucine (2 g) was dissolved in 1.5N sodium hydroxide solution (10 ml), dioxane (15 ml) was added, and cooled down to control the temperature between 0 and 5° C.; benzoyl chloride (2.3 g) and 1.5N sodium hydroxide solution were slowly added dropwisely to maintain the pH value at 9-10; the resulting mixture was allowed to react at 0° C. for 2 h and warm up naturally to room temperature to react for 2 h. Upon cooled, dilute hydrochloric acid was added dropwisely to adjust pH to 3, and the resulting mixture was concentrated under reduced pressure to remove dioxane. The water phase was extracted with ethyl acetate (20 ml×3), the organic phase obtained was washed with acid, base and water until to be neutral, dried over anhydrous sodium sulfate, and the filtrate was concentrated to give 2.6 g colourless oil. The content was 92% (HPLC, mobile phase 1, method 2).
Rf=0.9
Developer: n-butyl alcohol:water:acetic acid:ethyl acetate=1:1:1:1
Color development: ultraviolet, iodine and 1% ninhydrin solution
MS: 258 (M+Na)

b) Preparation of N-benzoyl-D,L-leucyl-L-proline benzyl ester

N-benzoyl-D,L-leucine (2.3 g) and L-proline benzyl ester (2.7 g) were dissolved in dichloromethane (50 ml), DIEA (3 g) was added dropwisely under the protection of nitrogen upon cooled, HOBt (1.5 g) and EDCI (2.5 g) were added after the completion of addition, and the resulting mixture was allowed to warm up naturally to room temperature to react for 4 h, and concentrated under reduced pressure to remove the reaction liquid, and purified directly on a column to give 3.3 g colourless oil (72%), with the content being 98% (HPLC, mobile phase 1, method 1).
Rf=0.4
Developer: petroleum ether:ethyl acetate=2:1
Color development: ultraviolet, iodine and 1% ninhydrin solution
MS: 423 (M+H)

c) Preparation of N-benzoyl-D,L-leucyl-L-proline

N-benzoyl-D,L-leucyl-L-proline benzyl ester (2 g) was dissolved in methanol (40 ml), and 10% palladium-carbon (200 mg) was added. The resulting mixture aerated with hydrogen was allowed to react at room temperature for 3 h, filtered and concentrated under reduced pressure to remove the solvent to give a white foam-like solid (1.5 g, 98%), which was directly used for the next reaction.

d) Preparation of N-benzoyl-D,L-leucyl-L-proline-[(4-cyanophenyl)methyl]amide

N-benzoyl-D,L-leucyl-L-proline (830 mg), p-aminomethyl cyanophenyl hydrochloride (464 mg) and DIEA (742 mg) were dissolved in anhydrous dichloromethane (20 ml), and cooled down to 0° C. under the protection of nitrogen, and then HOBt (338 mg) and EDCI (575 mg) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 1.4 g crude product, which was purified with column chromatography to give a colourless oil (861 mg, yield: 77%).
Rf=0.5
Developer: petroleum ether:ethyl acetate=1:1
Color development: ultraviolet and iodine
MS: 469 (M+Na)

e) Preparation of N-benzoyl-D,L-leucyl-L-prolyl-{[4-(N'-hydroxyl) amidinophenyl]methyl}amide The product (861 mg) obtained in the above step was dissolved in water/ethanol (20 ml/20 ml), hydroxylamine hydrochloride and sodium carbonate were added under the protection of nitrogen, and the resulting mixture was allowed to react under reflux for 2 hours, cooled down, concentrated under reduced pressure to remove the solvent, and purified on a column to give a white foam-like solid (863 mg, 94.7%).

Rf=0.1
Developer: petroleum ether:ethyl acetate=1:1
Color development: ultraviolet and 1% ninhydrin solution
MS: 480 (M+H)

Example 6

N-benzoyl-D,L-leucyl-L-prolyl-[(4-amidinophenyl) methyl]amide acetate

The compound (500 mg) obtained in the Example 5 was dissolved in acetic acid (7 ml), acetic anhydride (250 mg) and 10% palladium-carbon (120 mg) were added, and the resulting mixture aerated with hydrogen was allowed to react for 24 hours, filtered and concentrated under reduced pressure to remove the solvent, aether (20 ml) was added, and the resulting mixture was placed in the refrigerator over night, and the solid precipitated out, which was filtered and dried (424 mg, 81%).
MS: 464 (M+H)

Example 7

N-phenylacetyl-D,L-leucyl-L-prolyl-{[4-(N'-hydroxyl) amidinophenyl]methyl}amide a) Preparation of N-phenylacetyl-D,L-leucine D,L-leucine (2 g) was dissolved in 1.5N sodium hydroxide solution (10 ml), dioxane (15 ml) was added, and cooled down to control the temperature between 0 and 5° C.; phenylacetyl chloride (2.4 g) and 1.5N sodium hydroxide solution were slowly added dropwisely to maintain the pH value at 9-10; The resulting mixture was allowed to react at 0° C. for 2 h and warm up naturally to room temperature to react for 2 h. Upon cooled, dilute hydrochloric acid was added dropwisely to adjust pH to 3, and the resulting mixture was concentrated under reduced pressure to remove dioxane. The water phase was extracted with ethyl acetate (20 ml×3), the organic phase obtained was washed with acid, base and water until to be neutral, dried over anhydrous sodium sulfate, and the filtrate was concentrated to give 2.5 g colourless oil.
The content was 90% (HPLC, mobile phase 1, method 2).
Rf=0.9
Developer: n-butyl alcohol:water:acetic acid:ethyl acetate=1:1:1:1
Color development: ultraviolet, iodine and 1% ninhydrin solution
Ms: 272 (M+Na)

b) Preparation of N-phenylacetyl-D,L-leucyl-L-proline benzyl ester

N-phenylacetyl-D,L-leucine (2.5 g) and L-proline benzyl ester (2.4 g) were dissolved in dichloromethane (50 ml), DIEA (2.8 g) was added dropwisely under the protection of nitrogen upon cooled, HOBt (1.35 g) and EDCI (2.3 g) were added after the completion of addition, and the resulting mixture was allowed to warm up naturally to room temperature to react for 4 h, and concentrated under reduced pressure to remove the reaction liquid, and purified directly on a column to give 3.6 g light green oil (83%), with the content being 97% (HPLC, mobile phase 1, method 1).
Rf=0.4
Developer: petroleum ether:ethyl acetate=2:1

Color development: ultraviolet, iodine and 1% ninhydrin solution
MS: 437 (M+H)

c) Preparation of N-phenylacetyl-D,L-leucyl-L-proline

N-phenylacetyl-D,L-leucyl-L-proline benzyl ester (2 g) was dissolved in methanol (40 ml), and 10% palladium-carbon (200 mg) was added. The resulting mixture aerated with hydrogen was allowed to react at room temperature for 3 h, filtered and concentrated under reduced pressure to remove the solvent to give a colourless sticky matter (1.55 g, 98%), which was directly used for the next reaction.

d) Preparation of N-phenylacetyl-D,L-leucyl-L-proline-[(4-cyanophenyl)methyl]amide N-phenylacetyl-D,L-leucyl-L-proline (866 mg), p-aminomethyl cyanophenyl hydrochloride (464 mg) and DIEA (742 mg) were dissolved in anhydrous dichloromethane (20 ml), and cooled down to 0° C. under the protection of nitrogen, and then HOBt (338 mg) and EDCI (575 mg) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 1.2 g crude product, which was purified with column chromatography to give a colourless oil (802 mg, yield: 69.6%).
Rf=0.5
Developer: petroleum ether:ethyl acetate=1:1
Color development: ultraviolet and iodine
MS: 483 (M+Na)

e) Preparation of N-phenylacetyl-D,L-leucyl-L-prolyl-{[4-(N'-hydroxyl) amidinophenyl] methyl}amide The product (802 mg) obtained in the above step was dissolved in water/ethanol (20 ml/20 ml), hydroxylamine hydrochloride and sodium carbonate were added under the protection of nitrogen, and the resulting mixture was allowed to react under reflux for 2 hours, cooled down, concentrated under reduced pressure to remove the solvent, and purified on a column to give a white foam-like solid (760 mg, 88.5%).
Rf=0.1
Developer: petroleum ether:ethyl acetate=1:1
Color development: ultraviolet and 1% ninhydrin solution
MS: 494 (M+H)

Example 8

N-phenylacetyl-D,L-leucyl-L-prolyl-[(4-amidino phenyl)methyl]amide acetate

The compound (500 mg) obtained in the Example 9 was dissolved in acetic acid (7 ml), acetic anhydride (250 mg) and 10% palladium-carbon (120 mg) were added, and the resulting mixture aerated with hydrogen was allowed to react for 24 hours, filtered and concentrated under reduced pressure to remove the solvent, aether (20 ml) was added, and then the resulting mixture was placed in the refrigerator over night, and the solid precipitated out, which was filtered and dried (386 mg, 71.2%).

MS: 478 (M+H)

Example 9

N-carboxylmethyl-D,L-leucyl-L-prolyl-{[4-(N'-hydroxyl) amidinophenyl]methyl}amide hydrochloride a) Preparation of N-(t-butyloxycarbonyl)methyl-D,L-leucine benzyl ester

D,L-leucine benzyl ester hydrochloride (4.9 g) was dissolved in DMF (30 ml), DIEA (15 ml) was added, tert-butyl bromoacetate (3.7 g) was added dropwisely slowly, and the resulting mixture was allowed to react at 40° C. for 12 h, then concentrated under reduced pressure to remove a great quantity of solvent. Ethyl acetate (30 ml) was added, and the organic phase was washed with saturated sodium hydrogencarbonate solution (20 ml×3), 5% KHSO$_4$ solution (20 ml×3) and water until to be neutral, and washed with saturated saline solution (20 ml×1), dried over anhydrous sodium sulfate, and the filtrate was concentrated to give a yellow oil, which was purified on a column to give 3.6 g pale yellow oil. The content was 99% (HPLC, mobile phase 1, method 1).

Rf=0.5

Developer: petroleum ether:ethyl acetate=1:2

Color development: ultraviolet, iodine and 1% ninhydrin solution

1H NMR (CDCl$_3$+D$_2$O) δ ppm: 0.913-0.942 (6H, d), 1.474 (9H, s), 1.532-1.584 (2H, m), 1.744-1.761 (1H, m), 3.236-3.305 (2H, m), 3.372-3.408 (1H, m), 5.182 (2H, s), 7.282-7.385 (5H, m)

b) Preparation of N-(t-butyloxycarbonyl)methyl-N-t-butyloxycarbonyl-D,L-leucine benzyl ester N-(t-butyloxycarbonyl)methyl-D,L-leucine benzyl ester (3.4 g) was dissolved in dichloromethane (20 ml), DIEA (1.3 g) and di-tert-butyl dicarbonate (2.8 g) were added dropwisely. The resulting mixture was allowed to react at 40° C. for 36 h, concentrated under reduced pressure to remove the reaction liquid, and purified directly on a column to give 4.4 g colourless oil (98%), with the content being 98% (HPLC, mobile phase 1, method 1).

Rf=0.5

Developer: petroleum ether:ethyl acetate=20:3

Color development: ultraviolet, iodine and 30% ninhydrin solution

1H NMR (CDCl$_3$) δ ppm: 0.910-0.938 (6H, d), 1.480 (18H, s), 1.522-1.57 (2H, m), 1.751-1.764 (1H, m), 3.321-3.342 (2H, m), 3.381-3.410 (1H, m), 5.214 (2H, s), 7.277-7.384 (5H, m)

c) Preparation of N-(t-butyloxycarbonyl)methyl-N-t-butyloxycarbonyl-D,L-leucine N-(t-butyloxycarbonyl)methyl-N-t-butyloxycarbonyl-D,L-leucine benzyl ester (3.5 g) was dissolved in methanol (25 ml), and 10% palladium-carbon (200 mg) was added. The resulting mixture aerated with hydrogen was allowed to react at room temperature for 3 h, filtered and concentrated under reduced pressure to remove the solvent to give a white foam-like solid (2.8 g, 100%), which was directly used for the next reaction.

d) Preparation of N-(t-butyloxycarbonyl)methyl-N-t-butyloxycarbonyl-D,L-leucyl-L-proline benzyl ester The product (2.8 g) obtained in the above step, L-proline benzyl ester hydrochloride (2.1 g) and DIEA (2.4 g) were dissolved in anhydrous dichloromethane (50 ml), and cooled down to 0° C. under the protection of nitrogen, and then HOBt (1.1 g) and EDCI (2.1 g) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 4.6 g crude product, which was purified with column chromatography to give a colourless oil (3.3 g, yield: 77%).

Rf=0.7

Developer: petroleum ether:ethyl acetate=2:1

Color development: ultraviolet and iodine

MS: 555 (M+Na$^+$)

e) Preparation of N-(t-butyloxycarbonyl)methyl-N-t-butyloxycarbonyl-D,L-leucyl-L-proline N-(t-butyloxycarbonyl)methyl-N-t-butyloxycarbonyl-D,L-leucyl-L-proline benzyl ester (3.3 g) was dissolved in methanol (30 ml), and 10% palladium-carbon (330 mg) was added. The resulting mixture aerated with hydrogen was allowed to react at room temperature for 3 h, filtered and concentrated under reduced pressure to remove the solvent to give a colourless oil (2.7 g, 98%), which was directly used for the next reaction.

Rf=0.1

Developer: petroleum ether:ethyl acetate=1:1

Color development: ultraviolet and 1% ninhydrin solution f) Preparation of N-(t-butyloxycarbonyl)methyl-N-t-butyloxycarbonyl-D,L-leucyl-L-prolyl-[(4-cyanophenyl)methyl]amide The product (1.4 g) obtained in the above step, p-aminomethyl cyanophenyl hydrochloride (591 mg) and DIEA (974 mg) were dissolved in anhydrous dichloromethane (50 ml), and cooled down to 0° C. under the protection of nitrogen, and then HOBt (443 mg) and EDCI (754 mg) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 1.8 g crude product, which was purified with column chromatography to give a colourless oil (1.5 g, yield: 81.7%).

Rf=0.4

Developer: petroleum ether:ethyl acetate=1:1

Color development: ultraviolet and iodine

MS: 579 (M+Na$^+$)

g) Preparation of N-(t-butyloxycarbonyl)methyl-N-t-butyloxycarbonyl-D,L-leucyl-L-prolyl-{[4-(N'-hydroxyl) amidinophenyl]methyl}amide The product (757 mg) obtained in the above step was dissolved in water/ethanol (20 ml/20 ml), hydroxylamine hydrochloride and sodium carbonate were added under the protection of nitrogen, and the resulting mixture was allowed to react under reflux for 2 hours, cooled down, concentrated under reduced pressure to remove the solvent, and purified on a column to give a white foam-like solid (785 mg, 97.7%).
Rf=0.2
Developer: petroleum ether:ethyl acetate=1:1
Color development: ultraviolet and 1% ninhydrin solution
MS: 612 (M+Na)

h) Preparation of N-carboxylmethyl-D,L-leucyl-L-prolyl-{[4-(N'-hydroxyl)amidinophenyl]methyl}amide hydrochloride The product (200 mg) obtained in the above step was dissolved in ethyl acetate (2 ml), 15% hydrochloric acid/ethyl acetate solution (2 ml) was added, and the resulting mixture was allowed to react at room temperature for 2 hours, concentrated under reduced pressure to give a white foam-like solid (157 mg, 99%).
MS: 492 (M+Na)

Example 10

N-carboxylmethyl-D,L-leucyl-L-prolyl-[(4-amidinophenyl)methyl]amide hydrochloride N-(t-butyloxycarbonyl)methyl-N-t-butyloxycarbonyl-D,L-leucyl-L-prolyl-{[4-(N'-hydroxyl)amidinophenyl]methyl}amide (500 mg) was dissolved in acetic acid (7 ml), acetic anhydride (250 mg) and 10% palladium-carbon (120 mg) were added. The resulting mixture aerated with hydrogen was allowed to react for 24 hours, filtered and concentrated under reduced pressure to remove the solvent, aether (20 ml) was added, and then the resulting mixture was placed in the refrigerator over night, and the solid precipitated out, which was filtered and dried (409 mg, 76%).
The product (409 mg) obtained in the above step was dissolved in ethyl acetate (4 ml), 15% hydrochloric acid/ethyl acetate solution (4 ml) was added, and the resulting mixture was allowed to react at room temperature for 2 hours, concentrated under reduced pressure to give a white foam-like solid (264 mg, 90%).
MS: 440 (M+Na)

Example 11

N-benzoyl-D,L-isoleucyl-L-prolyl-{[4-(N'-hydroxyl)amidinophenyl]methyl}amide a) Preparation of N-t-butyloxycarbonyl-D,L-isoleucyl-L-proline benzyl ester N-t-butyloxycarbonyl-D,L-isoleucine (8 g) and L-proline benzyl ester (9.17 g) was dissolved in dichloromethane (100 ml), DIEA (10.3 g) was added dropwisely under the protection of nitrogen upon cooled, HOBt (4.7 g) and EDCI (6.6 g) were added after the completion of addition, and the resulting mixture was allowed to warm up naturally to room temperature to react for 8 h, and concentrated under reduced pressure to remove the reaction liquid, and purified directly on a column to give 13.2 g light green oil (91.42%), with the content being 97% (HPLC, mobile phase 1, method 1).
Rf=0.5
Developer: petroleum ether:ethyl acetate=10:3
Color development: ultraviolet, iodine and 1% ninhydrin solution
MS: 441 (M+Na)
1H NMR (CDCl$_3$) δ ppm: 0.869-0.919 (3H, m), 0.943-0.961 (3H, m), 1.085-1.215 (1H, m), 1.424 (9H, s), 1.485-1.599 (1H, m), 1.659-1.758 (1H, m), 1.906-2.123 (3H, m), 2.145-2.238 (1H, m), 3.514-3.574 (0.5; H, m), 3.620-3.680 (0.5; H, m), 3.809-3.849 (1H, m), 4.265-4.306 (0.5; H, m), 4.471-4.483 (4H, dd), 4.567-4.601 (0.5; H, m), 5.103-5.280 (3H, m), 7.259-7.362 (5H, m)

b) Preparation of D,L-isoleucyl-L-proline benzyl ester hydrochloride

N-t-butyloxycarbonyl-D,L-isoleucyl-L-proline benzyl ester (13 g) was dissolved in ethyl acetate (34 ml), and 15% HCl/ethyl acetate solution (25 ml) was added dropwisely upon cooled. After the completion of addition, the resulting mixture was allowed to warm up naturally to room temperature to react for 4 h, and then concentrated under reduced pressure to remove the reaction liquid, and the oil was recrystallized with isopropanol/n-hexane to give 4.5 g white solid (90%), with the content being 94% (HPLC, mobile phase 1, method 2).
MS: 319 (M+H)

c) Preparation of N-benzoyl-D,L-isoleucyl-L-proline benzyl ester

D,L-isoleucyl-L-proline benzyl ester hydrochloride (1.2 g) was dissolved in dichloromethane (10 ml), cooled down to 0° C., and DIEA (860 mg) and benzoyl chloride (477 mg) were added dropwisely. The resulting mixture was allowed to warm up naturally to room temperature to react for 2 h, concentrated under reduced pressure to remove the solvent, and purified on a column to give a pale yellow oil (1.1 g, 79%).
MS: 423 (M+H)

d) Preparation of N-benzoyl-D,L-isoleucyl-L-proline

N-benzoyl-D,L-isoleucyl-L-proline benzyl ester (1.1 g) was dissolved in methanol (15 ml), and 10% palladium-carbon (120 mg) was added. The resulting mixture aerated with hydrogen was allowed to react at room temperature for 3 h, filtered and concentrated under reduced pressure to remove the solvent to give a colourless sticky matter (1.04 g, 99%), which was directly used for the next reaction.

e) Preparation of N-benzoyl-D,L-isoleucyl-L-proline-[(4-cyanophenyl)methyl]amide N-benzoyl-D,L-isoleucyl-L-proline (1.04 g), p-aminomethyl cyanophenyl hydrochloride (580 mg) and DIEA (929 mg) were dissolved in anhydrous dichloromethane (20 ml), cooled down to 0° C. under the protection of nitrogen, and then HOBt (423 mg) and EDCI (720 mg) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 1.3 g crude product, which was purified with column chromatography to give a colourless oil (1.15 g, yield: 82.3%).
Rf=0.1
Developer: petroleum ether:ethyl acetate=2:1
Color development: ultraviolet and iodine
MS: 447 (M+H)

f) Preparation of N-benzoyl-D,L-isoleucyl-L-prolyl-{[4-(N'-hydroxyl)amidinophenyl]methyl}amide The product (824 mg) obtained in the above step was dissolved in water/ethanol (20 ml/20 ml), hydroxylamine hydrochloride and sodium carbonate were added under the protection of nitrogen. The resulting mixture was allowed to react under reflux for 2 hours, cooled down, concentrated under reduced pressure to remove the solvent, and purified on a column to give a white foam-like solid (861 mg, 97%).
Rf=0.2
Developer: petroleum ether:ethyl acetate=1:1
Color development: ultraviolet and 1% ninhydrin solution
MS: 480 (M+H)

Example 12

N-benzoyl-D,L-isoleucyl-L-prolyl-[(4-amidino phenyl)methyl]amide acetate

The compound (667 mg) obtained in the Example 11 was dissolved in acetic acid (7 ml), acetic anhydride (216 mg) and 10% palladium-carbon (111 mg) were added. The resulting mixture aerated with hydrogen was allowed to react for 24 hours, filtered and concentrated under reduced pressure to remove the solvent, aether (20 ml) was added, and then the resulting mixture was placed in the refrigerator over night, and the solid precipitated out, which was filtered and dried (454 mg, 62%).
MS: 464 (M+H)

Example 13

N-phenylacetyl-D,L-isoleucyl-L-prolyl-{[4-(N'-hydroxyl) amidinophenyl]methyl}amide a) Preparation of N-phenylacetyl-D,L-isoleucyl-L-proline benzyl ester D,L-isoleucyl-L-proline benzyl ester hydrochloride (1.1 g) was dissolved in dichloromethane (10 ml), cooled down to 0° C., and DIEA (776 mg) and phenylacetyl chloride (473 mg) were added dropwisely. The resulting mixture was allowed to warm up naturally to room temperature to react for 2 h, concentrated under reduced pressure to remove the solvent, and purified on a column to give a pale yellow oil (1.2 g, 93%).
Rf=0.3
Developer: petroleum ether:ethyl acetate=2:1
Color development: ultraviolet and iodine
MS: 437 (M+H)

b) Preparation of N-phenylacetyl-D,L-isoleucyl-L-proline

N-phenylacetyl-D,L-isoleucyl-L-proline benzyl ester (1.2 g) was dissolved in methanol (15 ml), and 10% palladium-carbon (120 mg) was added. The resulting mixture aerated with hydrogen was allowed to react at room temperature for 3 h, filtered and concentrated under reduced pressure to remove the solvent to give a colourless sticky matter (939 mg, 97%), which was directly used for the next reaction.

c) Preparation of N-phenylacetyl-D,L-isoleucyl-L-proline-[(4-cyanophenyl)methyl]amide N-phenylacetyl-D,L-isoleucyl-L-proline (693 mg), p-aminomethyl cyanophenyl hydrochloride (337 mg) and DIEA (581 mg) were dissolved in anhydrous dichloromethane (20 ml), cooled down to 0° C. under the protection of nitrogen, and then HOBt (270 mg) and EDCI (460 mg) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 1.3 g crude product, which was purified with column chromatography to give a colourless oil (782 mg, yield: 85%).
Rf=0.1
Developer: petroleum ether:ethyl acetate=1:1
Color development: ultraviolet and iodine
MS: 461 (M+H)

d) Preparation of N-phenylacetyl-D,L-isoleucyl-L-prolyl-{[4-(N'-hydroxyl)amidinophenyl]methyl}amide The product (782 mg) obtained in the above step was dissolved in water/ethanol (20 ml/20 ml), hydroxylamine hydrochloride and sodium carbonate were added under the protection of nitrogen. The resulting mixture was allowed to react under reflux for 2 hours, cooled down, concentrated under reduced pressure to remove the solvent, and purified on a column to give a white foam-like solid (704 mg, 84%).
Rf=0.2
Developer: petroleum ether:ethyl acetate=1:1
Color development: ultraviolet and 1% ninhydrin solution
MS: 494 (M+H)

Example 14

N-phenylacetyl-D,L-isoleucyl-L-prolyl-[(4-amidino-phenyl)methyl]amide acetate

The compound (500 mg) obtained in the Example 13 was dissolved in acetic acid (7 ml), acetic anhydride (200 mg) and 10% palladium-carbon (110 mg) were added. The resulting mixture aerated with hydrogen was allowed to react for 24 hours, filtered and concentrated under reduced pressure to remove the solvent, aether (20 ml) was added, and then the resulting mixture was placed in the refrigerator over night, the solid precipitated out, which was filtered and dried (321 mg, 59%).
MS: 478 (M+H)

Example 15

N-carboxylmethyl-D,L-isoleucyl-L-prolyl-{[4-(N'-hydroxyl)amidinophenyl]methyl}amide hydrochloride a) Preparation of N-(t-butyloxycarbonyl)methyl-D,L-isoleucyl-L-proline benzyl ester D,L-isoleucyl-L-proline benzyl ester hydrochloride (1.8 g) was dissolved in acetonitrile (30 ml), DIEA (1.3 g) was added, t-butyl bromoacetate (1.1 g) was added slowly dropwisely. The resulting mixture was allowed to react at 40° C. for 24 h, and concentrated under reduced pressure to remove a great quantity of solvent. Ethyl acetate (30 ml) was added, and the organic phase was washed with saturated sodium hydrogencarbonate solution (20 ml×3), 5% $KHSO_4$ solution (20 ml×3) and water until to be neutral and washed with saturated saline solution (20 ml×1), dried over anhydrous sodium sulfate, and the filtrate was concentrated to give a yellow oil, which was purified on a column to give 1.7 g pale yellow oil. The content was 99% (HPLC, mobile phase 1, method 1).

Rf=0.5
Developer: petroleum ether:ethyl acetate=2:1
Color development: ultraviolet, iodine and 1% ninhydrin solution
MS: 455 (M+Na)

b) Preparation of N-(t-butyloxycarbonyl)methyl-N-t-butyloxycarbonyl-D,L-isoleucyl-L-proline benzyl ester N-(t-butyloxycarbonyl)methyl-D,L-isoleucine-L-proline benzyl ester (1.7 g) was dissolved in dichloromethane (20 ml), DIEA (542 mg) and di-tert-butyl dicarbonate (1 g) were added dropwisely. The resulting mixture was allowed to react at 40° C. for 48 h, and concentrated under reduced pressure to remove the reaction liquid, and purified directly on a column to give 1.7 g light yellow-green oil (81.2%), with the content being 96% (HPLC, mobile phase 1, method 1).

Rf=0.6
Developer: petroleum ether:ethyl acetate=20:4
Color development: ultraviolet, iodine and 1% ninhydrin solution
MS: 555 (M+Na)

c) Preparation of N-(t-butyloxycarbonyl)methyl-N-t-butyloxycarbonyl-D,L-leucine

N-(t-butyloxycarbonyl)methyl-N-t-butyloxycarbonyl-D,L-leucine benzyl ester (1.7 g) was dissolved in methanol (25 ml), and 10% palladium-carbon (200 mg) was added. The resulting mixture aerated with hydrogen was allowed to react at room temperature for 3 h, filtered and concentrated under reduced pressure to remove the solvent to give a white foam-like solid (1.38 g, 100%), which was directly used for the next reaction.

d) Preparation of N-(t-butyloxycarbonyl)methyl-N-t-butyloxycarbonyl-D,L-isoleucyl-L-prolyl-[(4-cyanophenyl)methyl]amide The product (930 mg) obtained in the above step, p-aminomethyl cyanophenyl hydrochloride (390 mg) and DIEA (630 mg) were dissolved in anhydrous dichloromethane (50 ml), cooled down to 0° C. under the protection of nitrogen, and then HOBt (284 mg) and EDCI (483 mg) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give the crude product, which was purified with column chromatography to give a colourless oil (708 mg, yield: 60.6%).

Rf=0.4
Developer: petroleum ether:ethyl acetate=1:1
Color development: ultraviolet and iodine
Ms: 579 (M+Na$^+$)

e) Preparation of N-(t-butyloxycarbonyl)methyl-N-t-butyloxycarbonyl-D,L-isoleucyl-L-prolyl-{[4-(N'-hydroxyl) amidinophenyl]methyl}amide The product (680 mg) obtained in the above step was dissolved in water/ethanol (20 ml/20 ml), hydroxylamine hydrochloride and sodium carbonate were added under the protection of nitrogen, and the resulting mixture was allowed to react under reflux for 2 hours, cooled down, concentrated under reduced pressure to remove the solvent, and purified on a column to a give white foam-like solid (780 mg, 97.8%).

Rf=0.2
Developer: petroleum ether:ethyl acetate=1:1
Color development: ultraviolet and 1% ninhydrin solution
MS: 612 (M+Na)

h) Preparation of N-carboxylmethyl-D,L-isoleucyl-L-prolyl-{[4-(N'-hydroxy)amidinophenyl]methyl}amide hydrochloride The product (200 mg) obtained in the above step was dissolved in ethyl acetate (2 ml), 15% hydrochloric acid/ethyl acetate solution (2 ml) was added, and the resulting mixture was allowed to react at room temperature for 2 hours and concentrated under reduced pressure to give a white foam-like solid (145 mg, 91%).
MS: 456 (M+Na)

Example 16

N-carboxylmethyl-D,L-isoleucyl-L-prolyl-[(4-amidinophenyl)methyl]amide hydrochloride N-(t-butyloxycarbonyl)methyl-N-t-butyloxycarbonyl-D,L-isoleucyl-L-prolyl-{[4-(N'-hydroxyl)amidinophenyl]methyl}amide (580 mg) was dissolved in acetic acid (7 ml), acetic anhydride (155 mg) and 10% palladium-carbon (100 mg) were added. The resulting mixture aerated with hydrogen was allowed to react for 24 hours, filtered and concentrated under reduced pressure to remove the solvent, aether (20 ml) was added, and then the resulting mixture was placed in the refrigerator over night, and the solid precipitated out, which was filtered and dried (610 mg, 87.5%).

The product (500 mg) obtained in the above step was dissolved in ethyl acetate (4 ml), 15% hydrochloric acid/ethyl acetate solution (4 ml) was added, the resulting mixture was allowed to react at room temperature for 2 hours, and concentrated under reduced pressure to give a white foam-like solid (294 mg, 75%).
MS: 440 (M+Na)

Example 17

N-benzenesulfonyl-L-leucyl-L-prolyl-[(4-amidinophenyl)methyl]amide hydrochloride a) Preparation of N-benzenesulfonyl-L-leucine L-leucine (6.5 g) was dissolved in 1.5N sodium hydroxide solution (40 ml), dioxane (40 ml) was added, and cooled down to control the temperature between 0 and 5° C.;

benzenesulfonyl chloride (10 g) and 1.5N sodium hydroxide solution were slowly added dropwise to maintain the pH at 9-10; the resulting mixture was allowed to react at 0° C. for 2 h and warm up naturally to room temperature to react for 2 h. Upon cooled, dilute hydrochloric acid was added dropwisely to adjust pH to 3, and the resulting mixture was concentrated under reduced pressure to remove dioxane, and a great quantity of solid precipitated out; filtered, the solid obtained was recrystallized with ethyl acetate/petroleum ether to give 9.4 g white solid. The content was 99% (HPLC, mobile phase 1, method 2).

Rf=0.8

Developer: n-butyl alcohol:water:acetic acid:ethyl acetate=1:1:1:1

Color development: ultraviolet, iodine and 1% ninhydrin solution b) Preparation of N-t-butyloxycarbonyl-L-prolyl{[(4-(N-benzyloxycarbonyl) amidinophenyl]methyl}amide N-t-butyloxycarbonyl-L-proline (2.2 g) and 4-aminomethyl-N'-benzyloxycarbonyl benzamidine hydrochloride (3.7 g) were dissolved in DMF (50 ml), DIEA (4.3 g) was added dropwisely under the protection of nitrogen upon cooled, and after the completion of addition, HOBt (1.35 g) and EDCI (2.3 g) were added, and the resulting mixture was allowed to warm up naturally to room temperature to react for 4 h, concentrated under reduced pressure to remove the reaction liquid, and purified directly on a column to give 4.6 g of white foam-like solid (95.7%), with the content being 98% (HPLC, mobile phase 1, method 1).

Rf=0.6

Developer: petroleum ether:ethyl acetate=1:2

Color development: ultraviolet, iodine and 1% ninhydrin solution

MS: 503 (M+Na)

c) Preparation of L-prolyl{[(4-(N-benzyloxycarbonyl) amidinophenyl]methyl}amide hydrochloride N-t-butyloxycarbonyl-L-prolyl-{[(4-(N-benzyloxycarbonyl) amidinophenyl]methyl}amide (4.6 g) was dissolved in isopropanol (30 ml), 15% HCl/ethyl acetate solution (30 mg) was added upon cooled, and the resulting mixture was concentrated under reduced pressure to remove the solvent, and the oil was recrystallized with isopropanol/aether to give a white solid (3.6 g, 91%).

MS: 381 (M+H)

d) Preparation of N-benzenesulfonyl-L-leucyl-L-prolyl-{[(4-(N-benzyloxycarbonyl)amidinophenyl]methyl}amide N-benzenesulfonyl-L-leucine (406 mg), L-prolyl-{[(4-benzyloxycarbonyl) amidinophenyl]methyl}amide hydrochloride (625 mg) and DIEA (426 mg) were dissolved in anhydrous dichloromethane (20 ml), cooled down to 0° C. under the protection of nitrogen, and then HOBt (203 mg) and EDCI (345 mg) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 905 mg crude product, which was purified with column chromatography to give a white foam-like solid (680 mg, yield: 71%).

Rf=0.4

Developer: petroleum ether:ethyl acetate=1:4

Color development: ultraviolet and iodine

MS: 634 (M+H)

e) Preparation of N-benzenesulfonyl-L-leucyl-L-prolyl-[(4-amidinophenyl)methyl]amide hydrochloride The product (450 mg) obtained in the above step was dissolved in methanol (20 ml), and 10% palladium-carbon (90 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to give a white foam-like solid (328 mg, 87%).

MS: 500 (M+H)

Example 18

N-benzenesulfonyl-D-leucyl-L-prolyl-{[(4-(N-benzyloxycarbonyl)amidinophenyl]methyl}amide a) Preparation of N-benzenesulfonyl-D-leucine

D-leucine (13.11 g) was dissolved in 1.5N sodium hydroxide solution (80 ml), dioxane (80 ml) was added, and cooled down to control the temperature between 0 and 5° C.; benzenesulfonyl chloride (19.8 g) and 1.5N sodium hydroxide solution were slowly added dropwisely to maintain the pH at 9-10; the resulting mixture was allowed to react at 0° C. for 2 h and warm up naturally to room temperature to react for 2 h. Upon cooled, dilute hydrochloric acid was added dropwisely to adjust pH to 3, the resulting mixture was concentrated under reduced pressure to remove dioxane, and a great quantity of solid precipitated out; filtered, and the solid obtained was recrystallized with ethyl acetate/petroleum ether to give 22.2 g white solid. The content was 99% (HPLC, mobile phase 1, method 2).

Rf=0.8

Developer: n-butyl alcohol:water:acetic acid:ethyl acetate=1:1:1:1

Color development: ultraviolet, iodine and 1% ninhydrin solution b) Preparation of N-benzenesulfonyl-D-leucyl-L-prolyl-{[(4-(N-benzyloxycarbonyl)amidinophenyl]methyl}amide N-benzenesulfonyl-D-leucine (406 mg), L-prolyl-{[(4-(N-benzyloxycarbonyl)amidinophenyl]methyl}amide hydrochloride (625 mg) and DIEA (426 mg) were dissolved in anhydrous dichloromethane (20 ml), cooled down to 0° C. under the protection of nitrogen, and then HOBt (203 mg) and EDCI (345 mg) were added. The resulting mixture was stirred at 0° C. for 20 min, and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 922 mg crude product, which was purified with column chromatography to give a white foam-like solid (707 mg, yield: 74%).

Rf=0.4

Developer: petroleum ether:ethyl acetate=1:4

Color development: ultraviolet and iodine

MS: 634 (M+H)

Example 19

N-benzenesulfony-D-leucyl-L-prolyl-[(4-amidinophenyl)methyl]amide hydrochloride c) Preparation of N-benzenesulfonyl-D-leucyl-L-prolyl-[(4-amidinophenyl)methyl]amide hydrochloride The product (467 mg) obtained in the above step was dissolved in methanol (20 ml), and 10% palladium-carbon (90 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to give a white foam-like solid (321 mg, 85%).

MS: 500 (M+H)

Example 20

N-benzylsulfonyl-D-leucyl-L-prolyl-{[(4-(N-benzyloxycarbonyl)amidinophenyl]methyl}amide a) Preparation of N-benzylsulfonyl-D-leucine D-leucine (2 g) was dissolved in 1.5N sodium hydroxide solution (10 ml), dioxane (15 ml) was added, and cooled down to control the temperature between 0 and 5° C.; benzylsulfonyl chloride (3.2 g) and 1.5N sodium hydroxide solution were slowly added dropwisely to maintain the pH at 9-10; the resulting mixture was allowed to react at 0° C. for 2 h and warm up naturally to room temperature to react for 2 h. Upon cooled, dilute hydrochloric acid was added dropwisely to adjust pH to 3, the resulting mixture was concentrated under reduced pressure to remove dioxane, and a great quantity of solid precipitated out; filtered, and the solid obtained was recrystallized with ethyl acetate/petroleum ether to give 3.2 g white solid. The content was 99% (HPLC, mobile phase 1, method 2).

Rf=0.8

Developer: n-butyl alcohol:water:acetic acid:ethyl acetate=1:1:1:1

Color development: ultraviolet, iodine and 1% ninhydrin solution

MS: 308 (M+Na)

b) Preparation of N-benzylsulfonyl-D-leucyl-L-prolyl-{[(4-(N-benzyloxycarbonyl)amidinophenyl]methyl}amide N-benzylsulfonyl-D-leucine (426 mg), L-prolyl-{[(4-(N-benzyloxycarbonyl) amidinophenyl]methyl}amide hydrochloride (625 mg) and DIEA (426 mg) were dissolved in anhydrous dichloromethane (20 ml), cooled down to 0° C. under the protection of nitrogen, and then HOBt (203 mg) and EDCI (345 mg) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 814 mg crude product, which was purified with column chromatography to give a white foam-like solid (650 mg, yield: 67%).

Rf=0.2

Developer: petroleum ether:ethyl acetate=1:4

Color development: ultraviolet and iodine

MS: 648 (M+H)

Example 21

N-benzylsulfony-D-leucyl-L-prolyl-[(4-amidinophenyl)methyl]amide hydrochloride c) Preparation of N-benzylsulfonyl-D-leucyl-L-prolyl-[(4-amidinophenyl)methyl]amide hydrochloride The product (450 mg) obtained in the above step was dissolved in methanol (20 ml), and 10% palladium-carbon (90 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to give a white foam-like solid (306 mg, 80%).

MS: 514 (M+H)

Example 22

N-benzoyl-D-leucyl-L-prolyl-[(4-amidinophenyl)methyl]amide hydrochloride a) Preparation of N-benzoyl-D-leucine D-leucine (2 g) was dissolved in 1.5N sodium hydroxide solution (10 ml), dioxane (15 ml) was added, and cooled down to control the temperature between 0 and 5° C.; benzoyl chloride (2.3 g) and 1.5N sodium hydroxide solution were slowly added dropwisely to maintain the pH at 9-10; the resulting mixture was allowed to react at 0° C. for 2 h and warm up naturally to room temperature to react for 2 h. Upon cooled, dilute hydrochloric acid was added dropwisely to adjust pH to 3, and the resulting mixture was concentrated under reduced pressure to remove dioxane, and the water phase was extracted with ethyl acetate (20 ml×3), the organic phase obtained was washed with acid, base and water until to be neutral, dried over anhydrous sodium sulfate, and the filtrate was concentrated to give 2.5 g colourless oil. The content was 92% (HPLC, mobile phase 1, method 2).

Rf=0.9

Developer: n-butyl alcohol:water:acetic acid:ethyl acetate=1:1:1:1

Color development: ultraviolet, iodine and 1% ninhydrin solution

MS: 258 (M+Na)

b) the preparation of N-benzoyl-D-leucyl-L-prolyl-{[(4-(N-benzyloxycarbonyl)amidinophenyl]methyl}amide N-benzoyl-D-leucine (366 mg), L-prolyl-{[(4-(N-benzyloxycarbonyl) amidinophenyl]methyl}amide hydrochloride (626 mg) and DIEA (426 mg) were dissolved in anhydrous dichloromethane (20 ml), cooled down to 0° C. under the protection of nitrogen, and then HOBt (203 mg) and EDCI (345 mg) were added, the resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 778 mg crude product, which was purified with column chromatography to give a white foam-like solid (600 mg, yield: 67%).

Rf=0.3

Developer: petroleum ether:ethyl acetate=1:2

Color development: ultraviolet and iodine

MS: 598 (M+H)

c) Preparation of N-benzoyl-D-leucyl-L-prolyl-[(4-amidino phenyl)methyl]amide hydrochloride The product (500 mg) obtained in the above step was dissolved in methanol (20 ml), and 10% palladium-carbon (100 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to give a white foam-like solid (315 mg, 78.7%).

MS: 464 (M+H)

Example 23

N-phenylacetyl-D-leucyl-L-prolyl-[(4-amidino phenyl)methyl]amide hydrochloride a) Preparation of N-phenylacetyl-D-leucine

D-leucine (2 g) was dissolved in 1.5N sodium hydroxide solution (10 ml), dioxane (15 ml) was added, and cooled down to control the temperature between 0 and 5° C.; phenylacetyl chloride (2.4 g) and 1.5N sodium hydroxide solution were slowly added dropwisely to maintain the pH at 9-10; the resulting mixture was allowed to react at 0° C. for 2 h and warm up naturally to room temperature to react for 2 h. Upon cooled, dilute hydrochloric acid was added dropwisely to adjust pH to 3, and the resulting mixture was concentrated under reduced pressure to remove dioxane, and the water phase was extracted with ethyl acetate (20 ml×3), the organic phase obtained was washed with acid, base and water until to be neutral, dried over anhydrous sodium sulfate, and the filtrate was concentrated to give 2.7 g colourless oil. The content was 93% (HPLC, mobile phase 1, method 2).

Rf=0.9

Developer: n-butyl alcohol:water:acetic acid:ethyl acetate=1:1:1:1

Color development: ultraviolet, iodine and 1% ninhydrin solution

MS: 272 (M+Na)

b) Preparation of N-phenylacetyl-D-leucyl-L-prolyl-{[(4-(N-benzyloxycarbonyl)amidinophenyl]methyl}amide N-phenylacetyl-D-leucine (379 mg), L-prolyl-{[(4-(N-benzyloxycarbonyl) amidinophenyl]methyl}amide hydrochloride (626 mg) and DIEA (426 mg) were dissolved in anhydrous dichloromethane (20 ml), cooled down to 0° C. under the protection of nitrogen, and then HOBt (203 mg) and EDCI (345 mg) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 850 mg crude product, which was purified with column chromatography to give a white foam-like solid (514 mg, yield: 56%).

Rf=0.3

Developer: petroleum ether:ethyl acetate=1:4

Color development: ultraviolet and iodine

MS: 612 (M+H)

c) Preparation of N-phenylacetyl-D-leucyl-L-prolyl-[(4-amidinophenyl)methyl]amide hydrochloride The product (500 mg) obtained in the above step was dissolved in methanol (20 ml), and 10% palladium-carbon (100 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to a give white foam-like solid (180 mg, 44%).

MS: 478 (M+H)

Example 24

N-carboxylmethyl-D-leucyl-L-prolyl-[(4-amidino phenyl)methyl]amide hydrochloride a) Preparation of N-(t-butyloxycarbonyl)methyl-D-leucine benzyl ester

D-leucine benzyl ester hydrochloride (3.9 g) was dissolved in DMF (30 ml), DIEA (3.9 g) was added, tert-butyl bromoacetate (3.2 g) was added dropwisely slowly, and the resulting mixture was allowed to react at 40° C. for 36 h, and concentrated under reduced pressure to remove a great quantity of solvent, ethyl acetate (50 ml) was added, and the organic phase was washed with saturated sodium hydrogencarbonate solution (50 ml×3), 5% KHSO$_4$ solution (50 ml×3) and water until to be neutral, and washed with saturated saline solution (50 ml×1), dried over anhydrous sodium sulfate, and the filtrate was concentrated to give 5.2 g yellow oil, which was purified on a column to give 4.14 g light yellow-green oil. The content was 96% (HPLC, mobile phase 1, method 1).

Rf=0.5

Developer: petroleum ether:ethyl acetate=2:1

Color development: ultraviolet, iodine and 1% ninhydrin solution

MS: 358 (M+Na)

b) Preparation of N-(t-butyloxycarbonyl)methyl-N-t-butyloxycarbonyl-D-leucine benzyl ester N-(t-butyloxycarbonyl)methyl-D-leucine benzyl ester (3.74 g) was dissolved in dichloromethane (40 ml), DIEA (1.4 g) and di-tert-butyl dicarbonate (3.2 g) were added dropwisely, and the resulting mixture was allowed to react at 40° C. for 36 h, concentrated under reduced pressure to remove the reaction liquid, and purified directly on a column to give 3.5 g colourless oil (81.2%), with the content being 96% (HPLC, mobile phase 1, method 1).
Rf=0.6
Developer: petroleum ether:ethyl acetate=10:1
Color development: ultraviolet, iodine and 1% ninhydrin solution
MS: 458 (M+Na)

c) Preparation of N-(t-butyloxycarbonyl)methyl-N-t-butyloxycarbonyl-D-leucine N-(t-butyloxycarbonyl)methyl-N-t-butyloxycarbonyl-D-leucine benzyl ester (2.1 g) was dissolved in methanol (25 ml), and 10% palladium-carbon (210 mg) was added. The resulting mixture aerated with hydrogen was allowed to react at room temperature for 3 h, filtered and concentrated under reduced pressure to remove the solvent to give a colourless oil (1.66 g, 96%), which was directly used for the next reaction.

d) Preparation of N-(t-butyloxycarbonyl)methyl-N-t-butyloxycarbonyl-D-leucyl-L-prolyl-{[4-(N-benzyloxycarbonyl) amidinophenyl]methyl}amide hydrochloride N-(t-butyloxycarbonyl)methyl-N-t-butyloxycarbonyl-D-leucine (528 mg), L-prolyl-{[(4-(N-benzyloxycarbonyl)amidinophenyl]methyl}amide hydrochloride (626 mg) and DIEA (426 mg) were dissolved in anhydrous dichloromethane (20 ml), cooled down to 0° C. under the protection of nitrogen, and then HOBt (203 mg) and EDCI (345 mg) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 883 mg crude product, which was purified with column chromatography to give a white foam-like solid (752 mg, yield: 71%).
Rf=0.4
Developer: petroleum ether:ethyl acetate=10:15
Color development: ultraviolet and iodine
MS: 730 (M+Na)

e) Preparation of N-carboxylmethyl-D-leucyl-L-prolyl-[(4-amidinophenyl)methyl]amide hydrochloride The product (500 mg) obtained in the above step was dissolved in methanol (20 ml), and 10% palladium-carbon (100 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was allowed to react for 2 h and evaporated to dryness to give a white foam-like solid (246 mg, 71.4%).
Ms: 440 (M+Na)

Example 25

N-benzenesulfonyl-D-leucyl-L-prolyl-[1-(aminoiminomethyl)-piperid-4-yl]methyl amide hydrochloride a) Preparation of N-benzenesulfonyl-D-leucyl-L-prolyl-{1-[(N,N'-dibenzyloxycarbonyl)aminoiminomethyl]-piperid-4-yl}methyl amide N-benzenesulfonyl-D-leucine (325 mg), L-prolyl-{1-[(N,N'-dibenzyloxycarbonyl)aminoiminomethyl]-piperid-4-yl}methyl amide hydrochloride (670 mg) and DIEA (341 mg) were dissolved in anhydrous dichloromethane (20 ml), cooled down to 0° C. under the protection of nitrogen, and then HOBt (162 mg) and EDCI (276 mg) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 622 mg crude product, which was purified with column chromatography to give a white foam-like solid (528 mg, yield: 56.8%).
Rf=0.4
Developer: petroleum ether:ethyl acetate=1:1
Color development: ultraviolet and iodine
MS: 776 (M+H)

b) Preparation of N-benzenesulfonyl-D-leucyl-L-prolyl-[1-(aminoiminomethyl)-piperid-4-yl]methyl amide hydrochloride The product (450 mg) obtained in the above step was dissolved in methanol (20 ml), and 10% palladium-carbon (90 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to give white foam-like solid (210 mg, 66.7%).
MS: 507 (M+H)

Example 26

N-benzenesulfonyl-D-leucyl-L-prolyl-[1-(aminoiminomethyl)-piperid-3-yl]methyl amide hydrochloride a) Preparation of N-benzenesulfonyl-D-leucyl-L-prolyl-{1-[(N,N'-dibenzyloxycarbonyl)aminoiminomethyl]-piperid-3-yl}methyl amide N-benzenesulfonyl-D-leucine (325 mg), L-prolyl-{1-[(N,N'-dibenzyloxycarbonyl)aminoiminomethyl]-piperid-3-yl}methyl amide hydrochloride (670 mg) and DIEA (341 mg) were dissolved in anhydrous dichloromethane (20 ml), cooled down to 0° C. under the protection of nitrogen, and then HOBt (162 mg) and EDCI (276 mg) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 597 mg crude product, which was purified with column chromatography to give a white foam-like solid (495 mg, yield: 51%).
Rf=0.3
Developer: petroleum ether:ethyl acetate=1:1
Color development: ultraviolet and iodine
MS: 776 (M+H)

b) Preparation of N-benzenesulfonyl-D-leucyl-L-prolyl-[1-(aminoiminomethyl)-piperid-3-yl]methyl amide hydrochloride The product (450 mg) obtained in the above step was dissolved in methanol (20 ml), and 10% palladium-carbon (90 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to give a white foam-like solid (200 mg, 64%).

MS: 507 (M+H)

Example 27

N-benzenesulfonyl-D-leucyl-L-prolyl-[1-(aminoiminomethyl)-pyrrol-3-yl]methyl amide hydrochloride a) Preparation of N-benzenesulfonyl-D-leucyl-L-prolyl-{1-[(N,N'-dibenzyloxycarbonyl)aminoiminomethyl]-pyrrol-3-yl}methyl amide N-benzenesulfonyl-D-leucine (325 mg), L-prolyl-{-1-[(N,N'-dibenzyloxycarbonyl)aminoiminomethyl]-piperid-3-yl}methyl amide hydrochloride (816 mg) and DIEA (341 mg) were dissolved in anhydrous dichloromethane (20 ml), cooled down to 0° C. under the protection of nitrogen, and then HOBt (162 mg) and EDCI (276 mg) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 681 mg crude product, which was purified with column chromatography to give a white foam-like solid (554 mg, yield: 48%).

Rf=0.3
Developer: petroleum ether:ethyl acetate=1:1
Color development: ultraviolet and iodine
MS: 761 (M+H)

b) Preparation of N-benzenesulfonyl-D-leucyl-L-prolyl-[1-(aminoiminomethyl)-pyrrol-3-yl]methyl amide hydrochloride The product (450 mg) obtained in the above step was dissolved in methanol (20 ml), and 10% palladium-carbon (90 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to give a white foam-like solid (257 mg, 64%).

MS: 507 (M+H)

Example 28

N-benzenesulfonyl-D-isoleucyl-L-prolyl-[(4-amidinophenyl)methyl]amide hydrochloride a) Preparation of N-benzenesulfonyl-D-isoleucine

D-isoleucine (262 mg) was dissolved in 1.5N sodium hydroxide solution (4 ml), dioxane (4 ml) was added, and cooled down to control the temperature between 0 and 5° C.; benzenesulfonyl chloride (389 mg) and 1.5N sodium hydroxide solution were slowly added dropwisely to maintain the pH at 9-10; the resulting mixture was allowed to react at 0° C. for 2 h and warm up naturally to room temperature to react for 2 h. Dilute hydrochloric acid was added dropwisely upon cooled to adjust pH to 3, the resulting mixture was concentrated under reduced pressure to remove methanol, and the water phase was extracted with ethyl acetate (5 ml×3); the organic phases were combined, dried over anhydrous sodium sulfate, filtered and concentrated under reduced pressure to give crude product, which was purified on a column to give 434 mg colourless oil that was allowed to stand to solidify. The content was 99% (HPLC, mobile phase 1, method 2).

Rf=0.8
Developer: n-butyl alcohol:water:acetic acid:ethyl acetate=1:1:1:1
Color development: ultraviolet, iodine and 1% ninhydrin solution b) Preparation of N-benzenesulfonyl-D-isoleucyl-L-prolyl-{[(4-(N-benzyloxycarbonyl)amidinophenyl]methyl}amide N-benzenesulfonyl-D-leucyl-L-proline (406 mg), L-prolyl-{[(4-(N-benzyloxycarbonyl)amidinophenyl]methyl}amide hydrochloride (625 mg) and DIEA (426 mg) were dissolved in anhydrous dichloromethane (20 ml), cooled down to 0° C. under the protection of nitrogen, and then HOBt (203 mg) and EDCI (345 mg) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 894 mg crude product, which was purified with column chromatography to give a white foam-like solid (627 mg, yield: 66%).

Rf=0.4
Developer: petroleum ether:ethyl acetate=1:4
Color development: ultraviolet and iodine
MS: 634 (M+H)

e) Preparation of N-benzenesulfonyl-D-isoleucyl-L-prolyl-[(4-amidinophenyl)methyl]amide hydrochloride The product (450 mg) obtained in the above step was dissolved in methanol (20 ml), 10% palladium-carbon (90 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to give a white foam-like solid (304 mg, 81%).

MS: 500 (M+H)

Example 29

N-benzylsulfonyl-D-leucyl-L-prolyl-[(5-amidino-2-thienyl)methyl]amide hydrochloride a) Preparation of N-benzylsulfonyl-D-leucyl-L-proline benzyl ester

N-benzylsulfonyl-D-leucine (4.3 g) and L-proline benzyl ester (4.1 g) were dissolved in dichloromethane (50 ml), DIEA (4.7 g) was added dropwisely under the protection of nitrogen upon cooled, and after the completion of addition, HOBt (2 g) and EDCI (3.8 g) were added, the resulting mixture was allowed to warm up naturally to room temperature to react for 4 h, concentrated under reduced pressure to remove the reaction liquid, and purified directly on a column to give 5 g colourless oil that was allowed to stand to solidify (72%), with the content being 98% (HPLC, mobile phase 1, method 1).

Rf=0.5
Developer: petroleum ether:ethyl acetate=2:1
Color development: ultraviolet, iodine and 1% ninhydrin solution
MS: 473 (M+H)

b) Preparation of N-benzylsulfonyl-D-leucyl-L-proline

N-benzylsulfonyl-D-leucyl-L-proline benzyl ester (1.2 g) was dissolved in methanol (20 ml), and 10% palladium-carbon (120 mg) was added. The resulting mixture aerated with hydrogen was allowed to react at room temperature for 3 h, filtered and concentrated under reduced pressure to remove the solvent to give a white foam-like solid (981 mg, 97%), which was directly used for the next reaction.

c) Preparation of N-benzylsulfonyl-D-leucyl-L-proline-[(5-cyano-2-thienyl)methyl]amide N-benzylsulfonyl-D-leucyl-L-proline (1 g), 5-aminomethyl thiophen-2-carbonitrile hydrochloride (463 mg) and DIEA (773 mg) were dissolved in anhydrous dichloromethane (20 ml), cooled down to 0° C. under the protection of nitrogen, and HOBt (351 mg) and EDCI (600 mg) were added. The resulting mixture was stirred at 0° C. for 20 min and allowed to warm up naturally to room temperature and react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 1.4 g crude product, which was purified with column chromatography to give a colourless oil (900 mg, yield: 69%).

Rf=0.3
Developer: petroleum ether:ethyl acetate=1:1
Color development: ultraviolet and iodine
MS: 503 (M+H)

d) Preparation of N-benzylsulfonyl-D-leucyl-L-prolyl-{[5-(N'-hydroxyl)amidino 2-thienyl]methyl}amide The product (900 mg) obtained in the above step was dissolved in water/ethanol (20 ml/20 ml), hydroxylamine hydrochloride and sodium carbonate were added under the protection of nitrogen. The resulting mixture was allowed to react under reflux for 2 hours, cooled down, concentrated under reduced pressure to remove the solvent, and purified on a column to give a white foam-like solid (857 mg, 88.9%).

Rf=0.1
Developer: petroleum ether:ethyl acetate=1:1
Color development: ultraviolet and 1% ninhydrin solution
MS: 536 (M+H)

e) N-benzylsulfonyl-D-leucyl-L-prolyl-[(5-amidino-2-thienyl)methyl]amide hydrochloride The compound obtained in the above step was dissolved in acetic acid (7 ml), acetic anhydride (260 mg) and 10% palladium-carbon (130 mg) were added. The resulting mixture aerated with hydrogen was allowed to react for 24 hours, filtered and concentrated under reduced pressure to remove the solvent, aether (20 ml) was added, and then the resulting mixture was placed in the refrigerator over night, and the solid precipitated out, which was filtered and dried (467 mg, 50.3%).

MS: 520 (M+1)

Example 30

N-benzenesulfonyl-D-leucyl-L-homoprolyl-[(4-amidinophenyl)methyl]amide hydrochloride a) Preparation of N-benzenesulfonyl-D-leucyl-L-homoproline benzyl ester N-benzenesulfonyl-D-leucine (1.4 g) and L-homoproline benzyl ester (1.3 g) were dissolved in dichloromethane (30 ml), DIEA (1.5 g) was added dropwisely under the protection of nitrogen upon cooled, and after the completion of addition, HOBt (675 mg) and EDCI (230 mg) were added. The resulting mixture was allowed to warm up naturally to room temperature to react for 4 h, concentrated under reduced pressure to remove the reaction liquid, and purified directly on a column to give 1.7 g white foam-like solid (74.2%), with the content being 98% (HPLC, mobile phase 1, method 1).

Rf=0.3
Developer: petroleum ether:ethyl acetate=2:1
Color development: ultraviolet, iodine and 1% ninhydrin solution
MS: 473 (M+H)

b) Preparation of N-benzenesulfonyl-D-leucyl-L-homoproline

N-benzenesulfonyl-D-leucyl-L-homoproline benzyl ester (1 g) was dissolved in methanol (10 ml), and 10% palladium-carbon (100 mg) was added. The resulting mixture aerated with hydrogen was allowed to react at room temperature for 3 h, filtered and concentrated under reduced pressure to remove the solvent to give a white foam-like solid (764 mg, 99%), which was directly used for the next reaction.

c) Preparation of N-benzenesulfonyl-D-leucyl-L-homoprolyl-{[(4-(N-benzyloxycarbonyl)amidinophenyl]methyl}amide N-benzenesulfonyl-D-leucyl-L-homoproline (573 mg) and 4-aminomethyl-N'-benzyloxycarbonyl benzamidine hydrochloride (540 mg) were dissolved in DMF (10 ml), DIEA (446 mg) was added dropwisely under the protection of nitrogen upon cooled, HOBt (203 mg) and EDCI (345 mg) were added after the completion of addition. The resulting mixture was allowed to warm up naturally to room temperature to react for 4 h, concentrated under reduced pressure to remove the reaction liquid, and purified directly on a column to give 559 mg white foam-like solid (57.6%), with the content being 98% (HPLC, mobile phase 1, method 1).

Rf=0.5
Developer: petroleum ether:ethyl acetate=1:2
Color development: ultraviolet, iodine and 1% ninhydrin solution
MS: 648 (M+H)

d) Preparation of N-benzenesulfonyl-D-leucyl-L-homoprolyl-[(4-amidinophenyl)methyl]amide hydrochloride The product (500 mg) obtained in the above step was dissolved in methanol (20 ml), and 10% palladium-carbon (90 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to give a white foam-like solid (318 mg, 75%).
MS: 514 (M+H)

Example 31

N-benzenesulfonyl-D-leucyl-(S)-azetidine-2-[(4-amidinophenyl)methyl]amide hydrochloride a) Preparation of N-benzenesulfonyl-L-leucyl-(S)-azetidine-2-carboxylic acid benzyl ester N-benzenesulfonyl-D-leucine (1.4 g) and (S)-azetidine-2-carboxylic acid benzyl ester (1 g) were dissolved in dichloromethane (30 ml), DIEA (1.5 g) was added dropwisely under the protection of nitrogen upon cooled, and after the completion of addition, HOBt (675 mg) and EDCI (230 mg) were added. The resulting mixture was allowed to warm up naturally to room temperature to react for 4 h, concentrated under reduced pressure to remove the reaction liquid, and purified directly on a column to give 1.5 g white solid (69%), with the content being 98% (HPLC, mobile phase 1, method 1).
Rf=0.2
Developer: petroleum ether:ethyl acetate=2:1
Color development: ultraviolet, iodine and 1% ninhydrin solution
MS: 445 (M+H)

b) Preparation of N-benzenesulfonyl-D-leucyl-(S)-azetidine-2-carboxylic acid

N-benzenesulfonyl-D-leucyl-(S)-azetidine-2-carboxylic acid benzyl ester (667 mg) was dissolved in methanol (10 ml), and 10% palladium-carbon (80 mg) was added. The resulting mixture aerated with hydrogen was allowed to react at room temperature for 3 h, filtered and concentrated under reduced pressure to remove the solvent to give a white foam-like solid (520 mg, 99%), which was directly used for the next reaction.

c) Preparation of N-benzenesulfonyl-D-leucyl-(S)-azetidine-2-{[(4-(N-benzyloxycarbonyl)amidinophenyl]methyl}amide N-benzenesulfonyl-D-leucyl-(S)-azetidine-2-carboxylic acid (520 mg) and 4-aminomethyl-N'-benzyloxycarbonyl benzamidine hydrochloride (540 mg) were dissolved in DMF (10 ml), DIEA (446 mg) was added dropwisely under the protection of nitrogen upon cooled, HOBt (203 mg) and EDCI (345 mg) were added after the completion of addition. The resulting mixture was allowed to warm up naturally to room temperature to react for 4 h, concentrated under reduced pressure to remove the reaction liquid, and purified directly on a column to give 566 mg white foam-like solid (61%), with the content being 98.5% (HPLC, mobile phase 1, method 1).
Rf=0.4
Developer: petroleum ether:ethyl acetate=1:2
Color development: ultraviolet, iodine and 1% ninhydrin solution
MS: 620 (M+H)

d) Preparation of N-benzenesulfonyl-D-leucyl-(S)-azetidine-2-[(4-amidinophenyl)methyl]amide hydrochloride The product (500 mg) obtained in the above step was dissolved in methanol (20 ml), and 10% palladium-carbon (90 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to give a white foam-like solid (328 mg, 78%).
MS: 486 (M+H)

Example 32

N-benzenesulfonyl-D-leucyl-L-prolyl-[1-(amino)-cyclohex-4-yl]methyl amide hydrochloride a) Preparation of N-benzenesulfonyl-D-leucyl-L-prolyl-{1-[(N-benzyloxycarbonyl)amino]-cyclohex-4-yl}methyl amide N-benzenesulfonyl-D-leucine-L-proline (553 mg) and 4-aminomethyl-N-benzyloxycarbonyl cyclohexylamine hydrochloride (450 mg) were dissolved in DMF (10 ml), DIEA (446 mg) was added dropwisely under the protection of nitrogen upon cooled, HOBt (203 mg) and EDCI (345 mg) were added after the completion of addition. The resulting mixture was allowed to warm up naturally to room temperature to react for 4 h, concentrated under reduced pressure to remove the reaction liquid, and purified directly on a column to give 542 mg white foam-like solid (59%), with the content being 98.5% (HPLC, mobile phase 1, method 1).
Rf=0.6
Developer: petroleum ether:ethyl acetate=1:2
Color development: ultraviolet, iodine and 1% ninhydrin solution
MS: 613 (M+H)

b) Preparation of N-benzenesulfonyl-D-leucyl-L-prolyl-[1-(amino)-cyclohex-4-yl]methyl amide hydrochloride The product (400 mg) obtained in the above step was dissolved in methanol (20 ml), and 10% palladium-carbon (90 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to give a white foam-like solid (273 mg, 81%).
MS: 516 (M+H)

Example 33

N-benzenesulfonyl-D-leucyl-L-prolyl-(4-amidino phenyl) amide hydrochloride a) Preparation of N-benzenesulfonyl-D-leucyl-L-prolyl-[(4-(N-benzyloxycarbonyl)amidinophenyl] amide N-benzenesulfonyl-D-leucine-L-proline (553 mg) and 4-amino-N-benzyloxycarbonyl benzamidine hydrochloride (460 mg) were dissolved in DMF (10 ml), DIEA (446 mg) was added dropwisely under the protection of nitrogen upon cooled, HOBt (203 mg) and EDCI (345 mg) were added after the completion of addition. The resulting mixture was allowed to warm up naturally to room temperature to react for 4 h, concentrated under reduced pressure to remove the reaction liquid, and purified directly on a column to give 315 mg white foam-like solid (34%), with the content being 98.5% (HPLC, mobile phase 1, method 1).

Rf=0.4
Developer: petroleum ether:ethyl acetate=1:2
Color development: ultraviolet, iodine and 1% ninhydrin solution
MS: 620 (M+H)

b) Preparation of N-benzenesulfonyl-D-leucyl-L-prolyl-(4-amidinophenyl) amide hydrochloride The product (300 mg) obtained in the above step was dissolved in methanol (15 ml), and 10% palladium-carbon (50 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to give a white foam-like solid (201 mg, 80%).
MS: 486 (M+H)

Example 34

N-benzenesulfonyl-D-leucyl-L-prolyl-[(4-amidino phenyl)ethyl]amide hydrochloride a) Preparation of N-benzenesulfonyl-D-leucyl-L-prolyl-{[(4-(N-benzyloxycarbonyl)amidinophenyl] ethyl}amide N-benzenesulfonyl-D-leucine-L-proline (553 mg) and 4-aminoethyl-N-benzyloxycarbonyl benzamidine hydrochloride (501 mg) were dissolved in DMF (10 ml), DIEA (446 mg) was added dropwisely under the protection of nitrogen upon cooled, HOBt (203 mg) and EDCI (345 mg) were added after the completion of addition. The resulting mixture was allowed to warm up naturally to room temperature to react for 4 h, concentrated under reduced pressure to remove the reaction liquid, and purified directly on a column to give 704 mg white foam-like solid (72.5%), with the content being 98.5% (HPLC, mobile phase 1, method 1).

Rf=0.45
Developer: petroleum ether:ethyl acetate=1:2
Color development: ultraviolet, iodine and 1% ninhydrin solution
MS: 648 (M+H)

b) Preparation of N-benzenesulfonyl-D-leucyl-L-prolyl-[(4-amidinophenyl)ethyl]amide hydrochloride The product (500 mg) obtained in the above step was dissolved in methanol (15 ml), and 10% palladium-carbon (50 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to give a white foam-like solid (361 mg, 85%).
MS: 514 (M+H)

Example 35

N-benzenesulfonyl-D-leucyl-L-prolyl-[(3-amidino phenyl)methyl]amide hydrochloride a) Preparation of N-benzenesulfonyl-D-leucyl-L-prolyl-{[(3-(N-benzyloxycarbonyl)amidinophenyl] methyl}amide N-benzenesulfonyl-D-leucine-L-proline (553 mg) and 3-aminomethyl-N-benzyloxycarbonyl benzamidine hydrochloride (450 mg) were dissolved in DMF (10 ml), DIEA (446 mg) was added dropwisely under the protection of nitrogen upon cooled, HOBt (203 mg) and EDCI (345 mg) were added after the completion of addition. The resulting mixture was allowed to warm up naturally to room temperature to react for 4 h, concentrated under reduced pressure to remove the reaction liquid, and purified directly on a column to give 681 mg white foam-like solid (71.8%), with the content being 98.5% (HPLC, mobile phase 1, method 1).

Rf=0.4
Developer: petroleum ether:ethyl acetate=1:2
Color development: ultraviolet, iodine and 1% ninhydrin solution
MS: 634 (M+H)

b) Preparation of N-benzenesulfonyl-D-leucyl-L-prolyl-[(3-amidinophenyl)methyl]amide hydrochloride The product (500 mg) obtained in the above step was dissolved in methanol (15 ml), and 10% palladium-carbon (50 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to give a white foam-like solid (364 mg, 86%).
MS: 500 (M+H)

Example 36

N-benzenesulfonyl-D-leucyl-L-prolyl-{[4-(N'-methoxyl) amidinophenyl]methyl}amide hydrochloride N-benzenesulfonyl-D-leucine-L-proline (553 mg) and 4-aminomethyl-(N'-methoxyl)benzamidine hydrochloride (323 mg) were dissolved in DMF (10 ml), DIEA (446 mg) was added dropwisely under the protection of nitrogen upon cooled, HOBt (203 mg) and EDCI (345 mg) were added after the completion of addition. The resulting mixture was allowed to warm up naturally to room temperature to react for 4 h, concentrated under reduced pressure to remove the reaction liquid, and purified directly on a column to give 420 mg white foam-like solid (52.9%), with the content being 98.5% (HPLC, mobile phase 1, method 1).

Rf=0.2
Developer: petroleum ether:ethyl acetate=1:2
Color development: ultraviolet, iodine and 1% ninhydrin solution
MS: 530 (M+H)

Example 37

N-benzenesulfonyl-D-leucyl-L-prolyl-[(4-aminomethyl phenyl)methyl]amide hydrochloride a) Preparation of N-benzenesulfonyl-D-leucyl-L-proline-[(4-cyanophenyl)methyl]amide N-benzenesulfonyl-D-leucyl-L-proline (737 mg), p-aminomethyl cyanophenyl hydrochloride (337 mg) and DIEA (569 mg) were dissolved in DMF (20 ml), cooled down to 0° C. under the protection of nitrogen, HOBt (270 mg) and EDCI (460 mg) were added. The resulting mixture was stirred at 0° C. for 20 min and allowed to warm up naturally to room temperature and react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 1.1 g crude product, which was purified with column chromatography to give a colourless oil (650 mg, yield: 67.3%).

Rf=0.65
Developer: petroleum ether:ethyl acetate=1:1
Color development: ultraviolet and iodine
MS: 505 (M+Na$^+$)

b) Preparation of N-benzenesulfonyl-D-leucyl-L-prolyl-[(4-aminomethylphenyl)methyl]amide hydrochloride The product (500 mg) obtained in the above step was dissolved in methanol (15 ml), and 10% palladium-carbon (50 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to give a white foam-like solid (455 mg, 84%).

MS: 487 (M+H)

Example 38

N-benzenesulfonyl-D-leucyl-L-prolyl-[(5-aminomethyl-2-thienyl)methyl]amide hydrochloride The N-benzenesulfonyl-D-leucyl-L-prolyl-[(5-cyano-2-thienyl)methyl]amide (500 mg) was dissolved in methanol (15 ml), and 10% palladium-carbon (50 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to give a white foam-like solid (383 mg, 71%).

MS: 493 (M+H)

Example 39

N-dimethylaminosulfonyl-D-leucyl-L-prolyl-[(4-amidinophenyl)methyl]amide hydrochloride a) Preparation of N-dimethylaminosulfonyl-D-leucine D-leucine (1.3 g) was dissolved in 1.5N sodium hydroxide solution (10 ml), dioxane (30 ml) was added, and cooled down to control the temperature between 0 and 5° C.; dimethylaminosulfonyl chloride (1.4 g) and 1.5N sodium hydroxide solution were slowly added dropwisely to maintain the pH at 9-10; the resulting mixture was allowed to react at 0° C. for 2 h and warm up naturally to room temperature to react for 2 h. Upon cooled, dilute hydrochloric acid was added dropwisely to adjust pH to 3. The resulting mixture was concentrated under reduced pressure to remove dioxane, and the water phase was extracted with ethyl acetate (20 ml×3), the organic phase obtained was washed with acid, base and water until to be neutral, dried over anhydrous sodium sulfate, the filtrate was concentrated, and purified on a column to give 1.33 g colourless oil. The content was 97% (HPLC, mobile phase 1, method 2).

Rf=0.8
Developer: n-butyl alcohol:water:acetic acid:ethyl acetate=1:1:1:1
Color development: iodine and 1% ninhydrin solution b) Preparation of N-dimethylaminosulfonyl-D-leucyl-L-prolyl-{[(4-(N-benzyloxycarbonyl)amidinophenyl]methyl}amide N-dimethylaminosulfonyl-D-leucine (357 mg), L-prolyl-{[(4-(N-benzyloxycarbonyl)amidinophenyl]methyl}amide hydrochloride (625 mg) and DIEA (426 mg) were dissolved in anhydrous dichloromethane (20 ml), cooled down to 0° C. under the protection of nitrogen, and then HOBt (203 mg) and EDCI (345 mg) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give mg crude product, which was purified with column chromatography to give a white foam-like solid (316 mg, yield: 35%).

Rf=0.2
Developer: petroleum ether:ethyl acetate=1:4
Color development: ultraviolet and iodine
MS: 601 (M+H)

c) Preparation of N-dimethylaminosulfonyl-D-leucyl-L-prolyl-[(4-amidinophenyl)methyl]amide hydrochloride The product (300 mg) obtained in the above step was dissolved in methanol (20 ml), and 10% palladium-carbon (40 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to give a white foam-like solid (154 mg, 62%).

MS: 467 (M+H)

Example 40

N-methanesulfonyl-D-leucyl-L-prolyl-[(4-amidino phenyl)methyl]amide hydrochloride a) Preparation of N-methanesulfonyl-D-leucine

D-leucine (1.3 g) was dissolved in 1.5N sodium hydroxide solution (10 ml), dioxane (30 ml) was added, and cooled down to control the temperature between 0 and 5° C.; methane sulfonyl chloride (1.1 g) and 1.5N sodium hydroxide solution were slowly added dropwise to maintain the pH at 9-10; the resulting mixture was allowed to react at 0° C. for 2 h and warm up naturally to room temperature to react for 2 h. Upon cooled, dilute hydrochloric acid was added dropwise to adjust pH to 3. The resulting mixture was concentrated under reduced pressure to remove dioxane, and the water phase was extracted with ethyl acetate (20 ml×3), the organic phase obtained was washed with acid, base and water until to be neutral, dried over anhydrous sodium sulfate, the filtrate was concentrated, and purified on a column to give 1.05 g colourless oil. The content was 97% (HPLC, mobile phase 1, method 2).

Rf=0.5

Developer: n-butyl alcohol:water:acetic acid:ethyl acetate=1:1:1:1

Color development: iodine and 1% ninhydrin solution b) Preparation of N-methanesulfonyl-D-leucyl-L-prolyl-{[(4-(N-benzyloxycarbonyl)amidinophenyl]methyl}amide N-methanesulfonyl-D-leucine (315 mg), L-prolyl-{[(4-(N-benzyloxycarbonyl)amidinophenyl]methyl}amide hydrochloride (625 mg) and DIEA (426 mg) were dissolved in anhydrous dichloromethane (20 ml), cooled down to 0° C. under the protection of nitrogen, and then HOBt (203 mg) and EDCI (345 mg) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give mg crude product, which was purified with column chromatography to give a white foam-like solid (300 mg, yield: 47%).

Rf=0.3

Developer: petroleum ether:ethyl acetate=1:3

Color development: ultraviolet and iodine

MS: 572 (M+H)

c) Preparation of N-methanesulfonyl-D-leucyl-L-prolyl-[(4-amidinophenyl)methyl]amide hydrochloride The product (300 mg) obtained in the above step was dissolved in methanol (20 ml), and 10% palladium-carbon (50 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to give a white foam-like solid (127 mg, 51%).

MS: 438 (M+H)

Example 41

N-ethanesulfonyl-D-leucyl-L-prolyl-[(4-amidino phenyl)methyl]amide hydrochloride a) Preparation of N-ethanesulfonyl-D-leucine

D-leucine (1.4 g) was dissolved in 1.5N sodium hydroxide solution (10 ml), dioxane (10 ml) was added, and cooled down to control the temperature between 0 and 5° C.; ethane sulfonyl chloride (1.3 g) and 1.5N sodium hydroxide solution were slowly added dropwise to maintain the pH at 9-10; the resulting mixture was allowed to react at 0° C. for 2 h and warm up naturally to room temperature to react for 2 h. Upon cooled, dilute hydrochloric acid was added dropwise to adjust pH to 3, and the resulting mixture was concentrated under reduced pressure to remove dioxane, and the water phase was extracted with ethyl acetate (20 ml×3), the organic phase obtained was washed with acid, base and water until to be neutral, dried over anhydrous sodium sulfate, the filtrate was concentrated, and purified on a column to give 1.17 g colourless oil. The content was 98% (HPLC, mobile phase 1, method 2).

Rf=0.7

Developer: n-butyl alcohol:water:acetic acid:ethyl acetate=1:1:1:1

Color development: iodine and 1% ninhydrin solution b) Preparation of N-ethanesulfonyl-D-leucyl-L-prolyl-{[(4-(N-benzyloxycarbonyl)amidinophenyl]methyl}amide N-ethanesulfonyl-D-leucine (336 mg), L-prolyl-{[(4-(N-benzyloxycarbonyl)amidinophenyl]methyl}amide hydrochloride (625 mg) and DIEA (426 mg) were dissolved in anhydrous dichloromethane (20 ml), cooled down to 0° C. under the protection of nitrogen, and then HOBt (203 mg) and EDCI (345 mg) were added, the resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give mg crude product, which was purified with column chromatography to give a white foam-like solid (473 mg, yield: 54%).

Rf=0.3 developer: petroleum ether:ethyl acetate=1:2 color development: ultraviolet and iodine

MS: 586 (M+H)

c) Preparation of N-ethanesulfonyl-D-leucyl-L-prolyl-[(4-amidinophenyl)methyl]amide hydrochloride The product (320 mg) obtained in the above step was dissolved in methanol (20 ml), and 10% palladium-carbon (50 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to give a white foam-like solid (179 mg, 67%).

MS: 452 (M+H)

Example 42

N-cyclopropanesulfonyl-D-leucyl-L-prolyl-[(4-amidinophenyl)methyl]amide hydrochloride a) Preparation of N-cyclopropanesulfonyl-D-leucine D-leucine (1.3 g) was dissolved in 1.5N sodium hydroxide solution (10 ml), dioxane (10 ml) was added, and cooled down to control the temperature between 0 and 5° C.; cyclopropane sulfonyl chloride (1.4 g) and 1.5N sodium hydroxide solution were slowly added dropwisely to maintain the pH at 9-10; the resulting mixture was allowed to react at 0° C. for 2 h and warm up naturally to room temperature to react for 2 h. Upon cooled, dilute hydrochloric acid was added dropwisely to adjust pH to 3, and the resulting mixture was concentrated under reduced pressure to remove dioxane, and the water phase was extracted with ethyl acetate (20 ml×3), the organic phase obtained was washed with acid, base and water until to be neutral, dried over anhydrous sodium sulfate, the filtrate was concentrated, and purified on a column to give 658 mg colourless oil. The content was 98% (HPLC, mobile phase 1, method 2).

Rf=0.7

Developer: n-butyl alcohol:water:acetic acid:ethyl acetate=1:1:1:1

Color development: iodine and 1% ninhydrin solution b) Preparation of N-cyclopropanesulfonyl-D-leucyl-L-prolyl-{[(4-(N-benzyloxycarbonyl)amidinophenyl]methyl}amide N-cyclopropanesulfonyl-D-leucine (355 mg), L-prolyl-{[(4-(N-benzyloxycarbonyl)amidinophenyl]methyl}amide hydrochloride (625 mg) and DIEA (426 mg) were dissolved in anhydrous dichloromethane (20 ml), cooled down to 0° C. under the protection of nitrogen, and then HOBt (203 mg) and EDCI (345 mg) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give mg crude product, which was purified with column chromatography to give a white foam-like solid (340 mg, yield: 38%).

Rf=0.2

Developer: petroleum ether:ethyl acetate=1:2

Color development: ultraviolet and iodine

MS: 598 (M+H)

c) Preparation of N-cyclopropanesulfonyl-D-leucyl-L-prolyl-[(4-amidinophenyl)methyl]amide hydrochloride The product (300 mg) obtained in the above step was dissolved in methanol (20 ml), and 10% palladium-carbon (40 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to give a white foam-like solid (110 mg, 44%).

MS: 464 (M+H)

Example 43

N-t-butyloxycarbonyl-D-leucyl-L-prolyl-[(4-amidinophenyl)methyl]amide hydrochloride a) Preparation of N-t-butyloxycarbonyl-D-leucine D-leucine (1.3 g) was dissolved in 1.5N sodium hydroxide solution (10 ml), dioxane (10 ml) was added; di-tert-butyl dicarbonate (2.6 g) was added slowly dropwisely, and allowed to react at room temperature for 8 h. Upon cooled, dilute hydrochloric acid was added dropwisely to adjust pH to 3, and the resulting mixture was concentrated under reduced pressure to remove dioxane, and the water phase was extracted with ethyl acetate (20 ml×3), the organic phase obtained was washed with acid, base and water until to be neutral, dried over anhydrous sodium sulfate, the filtrate was concentrated, and purified on a column to give 1.64 g colourless oil, which was allowed to stand to solidify. The content was 98%

(HPLC, mobile phase 1, method 2).

Rf=0.8

Developer: n-butyl alcohol:water:acetic acid:ethyl acetate=1:1:1:1

Color development: iodine and 1% ninhydrin solution b) Preparation of N-t-butyloxycarbonyl-D-leucyl-L-prolyl-{[(4-(N-benzyloxycarbonyl)amidinophenyl]methyl}amide N-t-butyloxycarbonyl-D-leucine (349 mg), L-prolyl-{[(4-(N-benzyloxycarbonyl)amidinophenyl]methyl}amide hydrochloride (625 mg) and DIEA (426 mg) were dissolved in anhydrous dichloromethane (20 ml), cooled down to 0° C. under the protection of nitrogen, and then HOBt (203 mg) and EDCI (345 mg) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give mg crude product, which was purified with column chromatography to give a white foam-like solid (614 mg, yield: 69%).

Rf=0.5

Developer: petroleum ether:ethyl acetate=1:2

Color development: ultraviolet and iodine

MS: 616 (M+Na)

c) Preparation of N-t-butyloxycarbonyl-D-leucyl-L-prolyl-[(4-amidinophenyl)methyl]amide hydrochloride The product (500 mg) obtained in the above step was dissolved in methano 1 (20 ml), and 10% palladium-carbon (80 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to give a white foam-like solid (302 mg, 73%).

MS: 482 (M+Na)

Example 44

N-methoxycarbonyl-D-leucyl-L-prolyl-[(4-amidinophenyl)methyl]amide hydrochloride a) Preparation of N-methoxycarbonyl-D-leucine

D-leucine (1.5 g) was dissolved in 1.5N sodium hydroxide solution (10 ml), dioxane (10 ml) was added, and cooled down to control the temperature between 0 and 5° C.; methyl chloroformate (1 g) and 1.5N sodium hydroxide solution were slowly added dropwisely to maintain the pH at 9-10; the resulting mixture was allowed to react at 0° C. for 2 h and warm up naturally to room temperature to react for 2 h. Upon cooled, dilute hydrochloric acid was added dropwisely to adjust pH to 3, and the resulting mixture was concentrated under reduced pressure to remove dioxane, and the water phase was extracted with ethyl acetate (20 ml×3), the organic phase obtained was washed with acid, base and water until to be neutral, dried over anhydrous sodium sulfate, the filtrate was concentrated, and purified on a column to give 1.35 g colourless oil. The content was 98% (HPLC, mobile phase 1, method 2).

Rf=0.7

Developer: n-butyl alcohol:water:acetic acid:ethyl acetate=1:1:1:1

Color development: iodine and 1% ninhydrin solution b) Preparation of N-methoxycarbonyl-D-leucyl-L-prolyl-{[(4-(N-benzyloxycarbonyl)amidinophenyl]methyl}amide N-methoxycarbonyl-D-leucine (288 mg), L-prolyl-{[(4-(N-benzyloxycarbonyl)amidinophenyl]methyl}amide hydrochloride (625 mg) and DIEA (426 mg) were dissolved in anhydrous dichloromethane (20 ml), cooled down to 0° C. under the protection of nitrogen, and then HOBt (203 mg) and EDCI (345 mg) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give mg crude product, which was purified with column chromatography to give a white foam-like solid (438 mg, yield: 53%).

Rf=0.4

Developer: petroleum ether:ethyl acetate=1:2

Color development: ultraviolet and iodine

Ms: 574 (M+Na)

c) Preparation of N-methoxycarbonyl-D-leucyl-L-prolyl-[(4-amidinophenyl)methyl]amide hydrochloride The product (300 mg) obtained in the above step was dissolved in methanol (20 ml), and 10% palladium-carbon (90 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to give a white foam-like solid (143 mg, 58%).

MS: 418 (M+H)

Example 45

N-carboxylethyl-D-leucyl-L-prolyl-[(4-amidinophenyl)methyl]amide hydrochloride a) Preparation of N-[2-(ethoxycarbonyl)ethyl]-D-leucine benzyl ester

D-leucine benzyl ester hydrochloride (5 g) was dissolved in DMF (30 ml), DIEA (2.6 g) was added, ethyl 3-bromopropionate (4.1 g) was added dropwisely slowly, and the resulting mixture was allowed to react at 60° C. for 36 h, and concentrated under reduced pressure to remove a great quantity of solvent. Ethyl acetate (20 ml) was added, and the organic phase was washed with saturated sodium hydrogencarbonate solution (50 ml×3), 5% $KHSO_4$ solution (50 ml×3) and water until to be neutral and washed with saturated saline solution (50 ml×1), dried over anhydrous sodium sulfate, and the filtrate was concentrated to give 1.57 g yellow oil, which was purified on a column to give 2.1 g light yellow-green oil. The content was 96% (HPLC, mobile phase 1, method 1).

Rf=0.5

Developer: petroleum ether:ethyl acetate=2:1

Color development: ultraviolet, iodine and 1% ninhydrin solution

MS: 344 (M+Na)

b) Preparation of N-[2-(ethoxycarbonyl)ethyl]-N-t-butyloxycarbonyl-D-leucine benzyl ester N-[2-(ethoxycarbonyl)ethyl-D-leucine benzyl ester (2.1 g) was dissolved in dichloromethane (20 ml), DIEA (1.1 g) and di-tert-butyl dicarbonate (1.8 g) were added dropwisely, and the resulting mixture was allowed to react at 40° C. for 36 h, concentrated under reduced pressure to remove the reaction liquid, and purified directly on a column to give 837 mg colourless oil (30.4%), with the content being 96% (HPLC, mobile phase 1, method 1).

Rf=0.5

Developer: petroleum ether:ethyl acetate=10:1

Color development: ultraviolet, iodine and 1% ninhydrin solution

Ms: 444 (M+Na)

c) Preparation of N-[2-(ethoxycarbonyl)ethyl]-N-t-butyloxycarbonyl-D-leucine N-[2-(ethoxycarbonyl)ethyl]-N-t-butyloxycarbonyl-D-leucine benzyl ester (837 mg) was dissolved in methanol (25 ml), and 10% palladium-carbon (90 mg) was added. The resulting mixture aerated with hydrogen was allowed to react at room temperature for 3 h, filtered and concentrated under reduced pressure to remove the solvent to give a colourless oil (612 mg, 93%), which was directly used for the next reaction.

d) Preparation of N-[2-(ethoxycarbonyl)ethyl]-N-t-butyloxycarbonyl-D-leucyl-L-prolyl-{[(4-(N-benzyloxycarbonyl) amidinophenyl]methyl}amide hydrochloride N-[2-(ethoxycarbonyl)ethyl]-N-t-butyloxycarbonyl-D-leucine (499 mg), L-prolyl-{[(4-(N-benzyloxycarbonyl)amidinophenyl]methyl}amide hydrochloride (626 mg) and DIEA (426 mg) were dissolved in anhydrous dichloromethane (20 ml), cooled down to 0° C. under the protection of nitrogen, and then HOBt (203 mg) and EDCI (345 mg) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 1.06 g crude product, which was purified with column chromatography to give a white foam-like solid (591 mg, yield: 57%).

Rf=0.4
Developer: petroleum ether:ethyl acetate=10:15
Color development: ultraviolet and iodine
MS: 716 (M+Na)

e) Preparation of N-carboxylethyl-D-leucyl-L-prolyl-[(4-amidinophenyl)methyl]amide hydrochloride The product (500 mg) obtained in the above step was dissolved in methanol (20 ml), and 10% palladium-carbon (100 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was allowed to react for 1 h, and the solvent was evaporated, and then dissolved with methanol (5 ml), 0.5N LiOH aqueous solution was added, and the resulting mixture was allowed to react for 2 h, and the reaction mixture was adjusted to pH 4 with dilute hydrochloric acid, and purified with TLC to give a white foam-like solid (83 mg, 24.7%).

MS: 490 (M+Na)

Example 46

N-p-methoxylphenylacetyl-D-leucyl-L-prolyl-[(4-amidinophenyl)methyl]amide hydrochloride a) Preparation of N-(p-methoxylphenylacetyl)-D-leucine benzyl ester P-methoxyl phenylacetic acid (1.29 g), D-leucine benzyl ester hydrochloride (2 g) and DIEA (2.2 g) were dissolved in anhydrous dichloromethane (60 ml), cooled down to 0° C. under the protection of nitrogen, and then HOBt (1.1 g) and EDCI (1.8 g) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 4.1 g crude product, which was purified with column chromatography to give a colourless oil (3.06 g, yield: 100%). The content was 99% (HPLC, mobile phase 1, method 1).

Rf=0.2
Developer: petroleum ether:ethyl acetate=4:1
Color development: ultraviolet, iodine and 1% ninhydrin solution
MS: 370 (M+H)

b) Preparation of N-p-methoxylphenylacetyl-D-leucine

N-p-methoxylphenylacetyl-D-leucine benzyl ester (3 g) was dissolved in methanol (40 ml), and 10% palladium-carbon (330 mg) was added. The resulting mixture aerated with hydrogen was allowed to react at room temperature for 3 h, filtered and concentrated under reduced pressure to remove the solvent to give a white foam (1.9 g, 91%), which was directly used for the next reaction.

Rf=0.7
Developer: n-butyl alcohol:water:acetic acid:ethyl acetate=1:1:1:1
Color development: iodine and 1% ninhydrin solution c) Preparation of N-p-methoxylphenylacetyl-D-leucyl-L-prolyl-[(4-cyanophenyl)methyl]amide hydrochloride N-p-methoxylphenylacetyl-D-leucine (1.9 g), L-prolyl-[(4-cyanophenyl)methyl]amide hydrochloride (2.13 g) and DIEA (2.27 g) were dissolved in anhydrous dichloromethane (20 ml), cooled down to 0° C. under the protection of nitrogen, and then HOBt (1.08 g) and EDCI (1.84 g) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 4.5 g crude product, which was purified with column chromatography to give a white foam-like solid (3.15 g, yield: 80%).

Rf=0.3
Developer: petroleum ether:ethyl acetate=1:2
Color development: ultraviolet and iodine
MS: 491 (M+H)

d) N-p-methoxylphenylacetyl-D-leucyl-L-prolyl-[(4-amidino phenyl)methyl]amide hydrochloride N-p-methoxylphenylacetyl-D-leucyl-L-prolyl-{[4-(N'-hydroxyl) amidinophenyl]methyl}amide (1.65 g) was dissolved in methanol (15 ml), then acetic anhydride (482 mg) and 10% palladium-carbon (250 mg) were added. The resulting mixture aerated with hydrogen was allowed to react for 24 hours, filtered and concentrated under reduced pressure to remove the solvent.

The product obtained in the above step was dissolved in ethyl acetate (4 ml), 15% hydrochloric acid/ethyl acetate solution (4 ml) was added, the resulting mixture was allowed to react at room temperature for 2 hours, concentrated under reduced pressure to remove the solvent, aether (20 ml) was added, and the resulting mixture was placed in the refrigerator over night and the solid precipitated out, which was filtered and dried (529 mg, 59%).

Rf=0.4
Developer: ethyl acetate
Color development: ultraviolet
MS: 545 (M+H)

Example 47

N-benzenesulfonyl-D-leucyl-L-prolyl-[(5-amidino-2-thienyl)methyl]amide hydrochloride a) Preparation of N-benzenesulfonyl-D-leucyl-L-prolyl-[(5-cyano-2-thienyl)methyl]amide N-benzenesulfonyl-D-leucine (542 mg), L-prolyl-[(5-cyano-2-thienyl)methyl]amide hydrochloride (500 mg) and DIEA (540 mg) were dissolved in anhydrous dichloromethane (20 ml), cooled down to 0° C. under the protection of nitrogen, and then HOBt (257 mg) and EDCI (437 mg) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 1.1 g crude product, which was purified with column chromatography to give a colourless oil (598 mg, yield: 66%).

Rf=0.1
Developer: petroleum ether:ethyl acetate=1:1
Color development: ultraviolet and iodine
MS: 489 (M+H)

b) Preparation of N-benzenesulfonyl-D-leucyl-L-prolyl-{[5-(N'-hydroxyl)amidinothienyl]2-yl}methyl amide The product (488 mg) obtained in the above step was dissolved in water/ethanol (20 ml/5 ml), hydroxylamine hydrochloride and sodium carbonate were added under the protection of nitrogen, and the resulting mixture was allowed to react under reflux for 2 hours, cooled down, concentrated under reduced pressure to remove the solvent, and purified on a column to give a white foam-like solid (529 mg, 100%).

Rf=0.2
Developer: ethyl acetate
Color development: ultraviolet and 1% ninhydrin solution
MS: 544 (M+Na)

c) N-benzenesulfonyl-D-leucyl-L-prolyl-[(5-amidino-2-thienyl)methyl]amide hydrochloride The compound obtained in the above step was dissolved in methanol (10 ml), then acetic anhydride (145 mg) and 10% palladium-carbon (130 mg) were added. The resulting mixture aerated with hydrogen were allowed to react for 24 hours, filtered and concentrated under reduced pressure to remove the solvent, hydrochloric acid/ethyl acetate solution (2 ml) was added, aether was added, and placed in the refrigerator over night and the solid precipitated out, which was filtered and dried (355 mg, 72.8%).

MS: 506 (M+H)

Example 48

N-carboxylmethyl-D-leucyl-L-prolyl-[(5-amidino-2-thienyl)methyl]amide hydrochloride a) Preparation of N-(t-butyloxycarbonyl)methyl-N-t-butyloxycarbonyl-D-leucyl-L-prolyl-[(5-cyanothienyl)methyl)-2-yl]methyl amide N-(t-butyloxycarbonyl)methyl-N-t-butyloxycarbonyl-D-leucine (690 mg), L-prolyl-[(5-cyano-2-thienyl)methyl] amide hydrochloride (543 mg) and DIEA (569 mg) were dissolved in anhydrous dichloromethane (20 ml), cooled down to 0° C. under the protection of nitrogen, and then HOBt (270 mg) and EDCI (460 mg) were added, the resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 1.6 g crude product, which was purified with column chromatography to give a colourless oil (1 g, yield: 92%).

Rf=0.2
Developer: petroleum ether:ethyl acetate=2:1
Color development: ultraviolet and iodine
MS: 585 (M+Na)

b) Preparation of N-(t-butyloxycarbonyl)methyl-N-t-butyloxycarbonyl-D-leucyl-L-prolyl-{[(5-(N'-hydroxyl) amidino thienyl]-2-yl}methyl amide The product (887 mg) obtained in the above step was dissolved in water/ethanol (20 ml/5 ml), hydroxylamine hydrochloride and sodium carbonate were added under the protection of nitrogen. The resulting mixture was allowed to react under reflux for 2 hours, cooled down, concentrated under reduced pressure to remove the solvent, and purified on a column to give a white foam-like solid (904 mg, 95%).

Rf=0.4
Developer: ethyl acetate
Color development: ultraviolet and 1% ninhydrin solution
MS: 618 (M+Na)

c) N-carboxylmethyl-D-leucyl-L-prolyl-[(5-amidino-2-thienyl)methyl]amide hydrochloride N-(t-butyloxycarbonyl)methyl-N-t-butyloxycarbonyl-D-leucyl-L-prolyl-{[5-(N'-hydroxyl)amidinothienyl]-2-yl}methyl amide (800 mg) was dissolved in methanol (10 ml), then acetic anhydride (206 mg) and 10% palladium-carbon (133 mg) were added. The resulting mixture aerated with hydrogen was allowed to react for 24 hours, filtered and concentrated under reduced pressure to remove the solvent, aether (20 ml) was added, and the resulting mixture was placed in the refrigerator over night and the solid precipitated out, which was filtered and dried.

The product obtained in the above step was dissolved in ethyl acetate (4 ml), 15% hydrochloric acid/ethyl acetate solution (4 ml) was added, the resulting mixture was allowed to react at room temperature for 2 hours, and concentrated under reduced pressure to give a white foam-like solid (254 mg, 41.2%).

MS: 446 (M+Na)

Example 49

N-benzenesulfonyl-D-leucyl-L-prolyl-[-(trans)-1-(amino)-cyclohex-4-yl]methyl amide hydrochloride a) Preparation of N-benzenesulfonyl-D-leucyl-L-prolyl-{-(trans)-1-[(N-benzyloxycarbonyl)amino]-cyclohex-4-yl}methyl amide N-benzenesulfonyl-D-leucine (1.03 g) and L-prolyl-{-(trans)-1-[(N-benzyloxycarbonyl)amino]-cyclohex-4-yl}methyl amide hydrochloride (1.5 g) were dissolved in dichloromethane (20 ml), DIEA (1 g) was added dropwisely under the protection of nitrogen upon cooled, and after the completion of addition, HOBt (512 mg) and EDCI (872 mg) were added, the resulting mixture was allowed to warm up naturally to room temperature to react for 4 h, concentrated under reduced pressure to remove the reaction liquid, and purified directly on a column to give 908 mg white solid (39%), with the content being 98.4% (HPLC, mobile phase 1, method 1).

Rf=0.25
Developer: petroleum ether:ethyl acetate=1:2
Color development: ultraviolet, iodine and 1% ninhydrin solution
MS: 613 (M+H)

b) Preparation of N-benzenesulfonyl-D-leucyl-L-prolyl-[-(trans)-1-(amino)-cyclohex-4-yl]methyl amide hydrochloride The product (900 mg) obtained in the above step was dissolved in methanol (20 ml), and 10% palladium-carbon (90 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to give a white foam-like solid (580 mg, 75%).
MS: 479 (M+H)

Example 50

N-benzylsulfonyl-D-leucyl-L-prolyl-[-(trans)-1-(amino)-cyclohex-4-yl]methyl amide hydrochloride a) Preparation of N-benzylsulfonyl-D-leucyl-L-prolyl-{-(trans)-1-[(N-benzyloxycarbonyl)amino]-cyclohex-4-yl}methyl amide N-benzylsulfonyl-D-leucine (856 mg) and L-prolyl-{-(trans)-1-[(N-benzyloxycarbonyl)amino]-cyclohex-4-yl}methyl amide hydrochloride (1.2 g) were dissolved in dichloromethane (20 ml), DIEA (667 mg) was added dropwisely under the protection of nitrogen upon cooled, and after the completion of addition, HOBt (405 mg) and EDCI (690 mg) were added, the resulting mixture was allowed to warm up naturally to room temperature to react for 4 h, concentrated under reduced pressure to remove the reaction liquid, and purified directly on a column to give 845 mg white solid (45%), with the content being 97.4% (HPLC, mobile phase 1, method 1).
Rf=0.35
Developer: petroleum ether:ethyl acetate=1:2
Color development: ultraviolet, iodine and 1% ninhydrin solution
MS: 628 (M+H)

b) Preparation of N-benzylsulfonyl-D-leucyl-L-prolyl-[-(trans)-1-(amino)-cyclohex-4-yl]methyl amide hydrochloride The product (800 mg) obtained in the above step was dissolved in methanol (20 ml), and 10% palladium-carbon (80 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to give a white foam-like solid (350 mg, 47.2%).
MS: 493 (M+H)

Example 51

N-benzenesulfonyl-D-leucyl-L-prolyl-{[(4-(N'-n-caproyl) amidinophenyl]methyl}amide N-benzenesulfonyl-D-leucyl-L-prolyl-[(4-amidinophenyl)methyl]amide hydrochloride (536 mg) was dissolved in tetrahydrofuran (20 ml), DIEA (258 mg) was added dropwisely upon cooled, and after the completion of addition, DMF (2 ml) was added, and caproyl chloride (135 mg) was added slowly dropwisely, the resulting mixture was allowed to warm up to room temperature to react for 8 h, concentrated under reduced pressure to remove the reaction liquid, and purified directly on a column to give 300 mg a white sticky solid (50%).
Rf=0.5
Developer: petroleum ether:ethyl acetate=1:3
Color development: ultraviolet, iodine and 1% ninhydrin solution
MS: 598 (M+H)

Example 52

N-benzenesulfonyl-D-leucyl-L-prolyl-{[(4-(N'-n-amyloxycarbonyl)amidinophenyl]methyl}amide N-benzenesulfonyl-D-leucyl-L-prolyl-[(4-amidinophenyl)methyl]amide hydrochloride (536 mg) was dissolved in tetrahydrofuran (20 ml), DIEA (258 mg) was added dropwisely upon cooled, and after the completion of addition, DMF (2 ml) was added, and n-amyloxycarbonyl chloride (150 mg) was added slowly dropwisely, the resulting mixture was allowed to warm up to room temperature to react for 8 h, concentrated under reduced pressure to remove the reaction liquid, and purified directly on a column to give 460 mg white solid (75%).
Rf=0.6
Developer: petroleum ether:ethyl acetate=1:3
Color development: ultraviolet, iodine and 1% ninhydrin solution
MS: 614 (M+H)

Example 53

N-p-methylbenzenesulfonyl-D-leucyl-L-prolyl-[(4-amidinophenyl)methyl]amide hydrochloride a) Preparation of N-p-methylbenzenesulfonyl-D-leucine D-leucine (1.4 g) was dissolved in 1.5N sodium hydroxide solution (10 ml), dioxane (10 ml) was added, and cooled down to control the temperature between 0 and 5° C.; p-methyl benzenesulfonyl chloride (1.9 g) and 1.5N sodium hydroxide solution were added slowly dropwisely to maintain the pH at 9-10; the resulting mixture was allowed to react at 0° C. for 2 h and warm up naturally to room temperature to react for 2 h. Upon cooled, dilute hydrochloric acid was added dropwisely to adjust pH to 3, and the resulting mixture was concentrated under reduced pressure to remove dioxane, and the water phase was extracted with ethyl acetate (20 ml×3), the resulting organic phase was washed with acid, base and water until to be neutral, dried over anhydrous sodium sulfate, and the filtrate was concentrated and purified on a column to give 2.5 g white solid.
Rf=0.7
Developer: n-butyl alcohol:water:acetic acid:ethyl acetate=1:1:1:1
Color development: iodine and 1% ninhydrin solution b) Preparation of N-p-methylbenzenesulfonyl-D-leucyl-L-prolyl-{[(4-(N-benzyloxycarbonyl)amidinophenyl]methyl}amide N-p-methyl-benzenesulfonyl-D-leucine (676 mg), L-prolyl-{[(4-(N-benzyloxycarbonyl)amidinophenyl]

methyl}amide hydrochloride (1 g) and DIEA (830 mg) were dissolved in anhydrous dichloromethane (40 ml), cooled down to 0° C. under the protection of nitrogen, and then HOBt (321 mg) and EDCI (547 mg) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 2.3 g crude product, which was purified with column chromatography to give a white foam-like solid (1.15 g, yield: 74.9%).

Rf=0.3
Developer: petroleum ether:ethyl acetate=1:2
Color development: ultraviolet and iodine
MS: 648 (M+H)

c) Preparation of N-p-methyl-benzenesulfonyl-D-leucyl-L-prolyl-[(4-amidinophenyl)methyl]amide hydrochloride The product (1 g) obtained in the above step was dissolved in methanol (20 ml), and 10% palladium-carbon (100 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to give a white solid (630, 76.3%).

MS: 514 (M+H)

Example 54

N-p-t-butyl-benzenesulfonyl-D-leucyl-L-prolyl-[(4-amidinophenyl)methyl]amide hydrochloride a) Preparation of N-p-t-butyl-benzenesulfonyl-D-leucine D-leucine (1.4 g) was dissolved in 1.5N sodium hydroxide solution (10 ml), dioxane (10 ml) was added, and cooled down to control the temperature between 0 and 5° C.; p-t-butyl benzenesulfonyl chloride (2.3 g) and 1.5N sodium hydroxide solution were added slowly dropwisely to maintain the pH at 9-10; the resulting mixture was allowed to react at 0° C. for 2 h and warm up naturally to room temperature to react for 2 h. Upon cooled, dilute hydrochloric acid was added dropwisely to adjust pH to 3, and the resulting mixture was concentrated under reduced pressure to remove dioxane, and the water phase was extracted with ethyl acetate (20 ml×3), the resulting organic phase was washed with acid, base and water until to be neutral, dried over anhydrous sodium sulfate, and the filtrate was concentrated and purified on a column to give a white solid (3 g, 83.2%).

Rf=0.8
Developer: n-butyl alcohol:water:acetic acid:ethyl acetate=1:1:1:1
Color development: iodine and 1% ninhydrin solution b) Preparation of N-p-t-butyl-benzenesulfonyl-D-leucyl-L-prolyl-{[(4-(N-benzyloxycarbonyl)amidinophenyl]methyl}amide N-p-t-butyl-benzenesulfonyl-D-leucine (1.8 g), L-prolyl-{[(4-(N-benzyloxycarbonyl)amidinophenyl]methyl}amide hydrochloride (2.5 g) and DIEA (1.92 g) were dissolved in anhydrous dichloromethane (40 ml), cooled down to 0° C. under the protection of nitrogen, and then HOBt (743 mg) and EDCI (1.26 g) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 2.7 g crude product, which was purified with column chromatography to give a white foam-like solid (2.7 g, yield: 71.2%).

Rf=0.3
Developer: petroleum ether:ethyl acetate=1:2
Color development: ultraviolet and iodine
MS: 691 (M+H)

c) Preparation of N-p-t-butyl-benzenesulfonyl-D-leucyl-L-prolyl-[(4-amidinophenyl)methyl]amide hydrochloride The product (800 mg) obtained in the above step was dissolved in methanol (20 ml), and 10% palladium-carbon (80 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to give a white solid (474 mg, 73%).

MS: 556 (M+H)

Example 55

N-p-fluoro-benzenesulfonyl-D-leucyl-L-prolyl-[(4-amidinophenyl)methyl]amide hydrochloride a) Preparation of N-p-fluoro-benzenesulfonyl-D-leucine D-leucine (1.4 g) was dissolved in 1.5N sodium hydroxide solution (10 ml), dioxane (10 ml) was added, and cooled down to control the temperature between 0 and 5° C.; p-fluoro-benzenesulfonyl chloride (1.95 g) and 1.5N sodium hydroxide solution were added slowly dropwisely to maintain the pH at 9-10; the resulting mixture was allowed to react at 0° C. for 2 h and warm up naturally to room temperature to react for 2 h. Upon cooled, dilute hydrochloric acid was added dropwisely to adjust pH to 3, and the resulting mixture was concentrated under reduced pressure to remove dioxane, and the water phase was extracted with ethyl acetate (20 ml×3), the resulting organic phase was washed with acid, base and water until to be neutral, dried over anhydrous sodium sulfate, and the filtrate was concentrated and purified on a column to give a pale yellow oil (2.7 g, 94%).

Rf=0.6
Developer: n-butyl alcohol:water:acetic acid:ethyl acetate=1:1:1:1
Color development: iodine and 1% ninhydrin solution b) Preparation of N-p-fluoro-benzenesulfonyl-D-leucyl-L-prolyl-{[(4-(N-benzyloxycarbonyl)amidinophenyl]methyl}amide N-p-fluoro-benzenesulfonyl-D-leucine (2.2 g), L-prolyl-{[(4-(N-benzyloxycarbonyl)amidinophenyl]methyl}amide hydrochloride (3.6 g) and DIEA (2.9 g) were dissolved in anhydrous dichloromethane (40 ml), cooled down to 0° C. under the protection of nitrogen, and then HOBt (1 g) and EDCI (1.73 g) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 3.4 g crude product, which was purified with column chromatography to give a white foam-like solid (3.4 g, yield: 69.5%).

Rf=0.2
Developer: petroleum ether:ethyl acetate=1:2
Color development: ultraviolet and iodine
MS: 652 (M+H)

c) Preparation of N-p-fluoro-benzenesulfonyl-D-leucyl-L-prolyl-[(4-amidinophenyl)methyl]amide hydrochloride The product (2.8 g) obtained in the above step was dissolved in methanol (20 ml), and 10% palladium-carbon (280 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to give a white solid (1.53 g, 64.4%).

MS: 518 (M+H)

Example 56

N-p-bromo-benzenesulfonyl-D-leucyl-L-prolyl-[(4-amidinophenyl)methyl]amide hydrochloride a) Preparation of N-p-bromo-benzenesulfonyl-D-leucine D-leucine (1.4 g) was dissolved in 1.5N sodium hydroxide solution (10 ml), dioxane (10 ml) was added, and cooled down to control the temperature between 0 and 5° C.; p-bromobenzenesulfonyl chloride (2.5 g) and 1.5N sodium hydroxide solution were added slowly dropwisely to maintain the pH at 9-10; the resulting mixture was allowed to react at 0° C. for 2 h and warm up naturally to room temperature to react for 2 h. Upon cooled, dilute hydrochloric acid was added dropwisely to adjust pH to 3, and the resulting mixture was concentrated under reduced pressure to remove dioxane, and the water phase was extracted with ethyl acetate (20 ml×3), the resulting organic phase was washed with acid, base and water until to be neutral, dried over anhydrous sodium sulfate, and the filtrate was concentrated and purified on a column to give a white solid (2 g, 96.4%).

Rf=0.5
Developer: n-butyl alcohol:water:acetic acid:ethyl acetate=1:1:1:1
Color development: iodine and 1% ninhydrin solution b) Preparation of N-p-bromo-benzenesulfonyl-D-leucyl-L-prolyl-{[(4-(N-benzyloxycarbonyl)amidinophenyl]methyl}amide N-p-bromo-benzenesulfonyl-D-leucine (3.3 g), L-prolyl-{[(4-(N-benzyloxycarbonyl)amidinophenyl]methyl}amide hydrochloride (4.3 g) and DIEA (3.1 g) were dissolved in anhydrous dichloromethane (40 ml), cooled down to 0° C. under the protection of nitrogen, and then HOBt (1.3 g) and EDCI (2.2 g) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 5 g crude product, which was purified with column chromatography to give a white foam-like solid (4 g, yield: 59.8%).

Rf=0.2
Developer: petroleum ether:ethyl acetate=1:2
Color development: ultraviolet and iodine
MS: 713 (M+H)

c) Preparation of N-p-bromo-benzenesulfonyl-D-leucyl-L-prolyl-[(4-amidinophenyl)methyl]amide hydrochloride The product (2.8 g) obtained in the above step was dissolved in methanol (20 ml), and 10% palladium-carbon (280 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to give a white solid (1.65 g, 67.3%).

MS: 579 (M+H)

Example 57

N-p-acetamido-benzenesulfonyl-D-leucyl-L-prolyl-[(4-amidinophenyl)methyl]amide hydrochloride a) Preparation of N-p-acetamido-benzenesulfonyl-D-leucine D-leucine (1.4 g) was dissolved in 1.5N sodium hydroxide solution (10 ml), dioxane (10 ml) was added, and cooled down to control the temperature between 0 and 5° C.; p-acetamido-benzenesulfonyl chloride (2.33 g) and 1.5N sodium hydroxide solution were added slowly dropwisely to maintain the pH at 9-10; the resulting mixture was allowed to react at 0° C. for 2 h and warm up naturally to room temperature to react for 2 h. Upon cooled, dilute hydrochloric acid was added dropwisely to adjust pH to 3, and the resulting mixture was concentrated under reduced pressure to remove dioxane, and the water phase was extracted with ethyl acetate (20 ml×3), the resulting organic phase was washed with acid, base and water until to be neutral, dried over anhydrous sodium sulfate, and the filtrate was concentrated and purified with a column to give a white solid (3 g, 83%).

Rf=0.4
Developer: n-butyl alcohol:water:acetic acid:ethyl acetate=1:1:1:1
Color development: iodine and 1% ninhydrin solution b) Preparation of N-p-acetamido-benzenesulfonyl-D-leucyl-L-prolyl-{[(4-(N-benzyloxycarbonyl)amidinophenyl]methyl}amide N-p-acetamido-benzenesulfonyl-D-leucine (1.64 g), L-prolyl-{[(4-(N-benzyloxycarbonyl)amidinophenyl]methyl}amide hydrochloride (2.26 g) and DIEA (1.74 g) were dissolved in anhydrous dichloromethane (40 ml), cooled down to 0° C. under the protection of nitrogen, and then HOBt (675 mg) and EDCI (1.15 g) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 3 g crude product, which was purified with column chromatography to give a white foam-like solid (2.64 g, yield: 76.4%).
Rf=0.5
Developer: ethyl acetate
Color development: ultraviolet and iodine
MS: 692 (M+H)

c) Preparation of N-p-acetamido-benzenesulfonyl-D-leucyl-L-prolyl-[(4-amidinophenyl)methyl]amide hydrochloride The product (2 g) obtained in the above step was dissolved in methanol (20 ml), and 10% palladium-carbon (200 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to give a white solid (1.2 g, 68.4%).
MS: 557 (M+H)

Example 58

N-1-naphthalenesulfonyl-D-leucyl-L-prolyl-[(4-amidinophenyl)methyl]amide hydrochloride a) Preparation of N-1-naphthalenesulfonyl-D-leucine D-leucine (1.4 g) was dissolved in 1.5N sodium hydroxide solution (10 ml), dioxane (10 ml) was added, and cooled down to control the temperature between 0 and 5° C.; p-1-naphthalenesulfonyl chloride (2.27 g) and 1.5N sodium hydroxide solution were added slowly dropwisely to maintain the pH at 9-10; the resulting mixture was allowed to react at 0° C. for 2 h and warm up naturally to room temperature to react for 2 h. Upon cooled, dilute hydrochloric acid was added dropwisely to adjust pH to 3, and the resulting mixture was concentrated under reduced pressure to remove dioxane, and the water phase was extracted with ethyl acetate (20 ml×3), the resulting organic phase was washed with acid, base and water until to be neutral, dried over anhydrous sodium sulfate, and the filtrate was concentrated and purified with a column to give a white solid (3.46 g, 98%).
Rf=0.7
Developer: n-butyl alcohol:water:acetic acid:ethyl acetate=1:1:1:1
Color development: iodine and 1% ninhydrin solution b) Preparation of N-1-naphthalenesulfonyl-D-leucyl-L-prolyl-{[(4-(N-benzyloxycarbonyl)amidinophenyl]methyl}amide N-1-naphthalenesulfonyl-D-leucine (1.6 g), L-prolyl-{[(4-(N-benzyloxycarbonyl)amidinophenyl]methyl}amide hydrochloride (2.26 g) and DIEA (1.47 g) were dissolved in anhydrous dichloromethane (40 ml), cooled down to 0° C.

under the protection of nitrogen, and then HOBt (700 mg) and EDCI (1.19 g) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 4 g crude product, which was purified with column chromatography to give a white foam-like solid (2.5 g, yield: 74%).
Rf=0.5
Developer: petroleum ether:ethyl acetate=1:2
Color development: ultraviolet and iodine
MS: 685 (M+H)

c) Preparation of N-1-naphthalenesulfonyl-D-leucyl-L-prolyl-[(4-amidinophenyl)methyl]amide hydrochloride The product (2 g) obtained in the above step was dissolved in methanol (20 ml), and 10% palladium-carbon (200 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to give a white solid (967 mg, 55%).
MS: 550 (M+H)

Example 59

N-2-naphthalenesulfonyl-D-leucyl-L-prolyl-[(4-amidinophenyl)methyl]amide hydrochloride a) Preparation of N-2-naphthalenesulfonyl-D-leucine D-leucine (1.4 g) was dissolved in 1.5N sodium hydroxide solution (10 ml), dioxane (10 ml) was added, and cooled down to control the temperature between 0 and 5° C.; p-2-naphthalenesulfonyl chloride (2.27 g) and 1.5N sodium hydroxide solution were added slowly dropwisely to maintain the pH at 9-10; the resulting mixture was allowed to react at 0° C. for 2 h and warm up naturally to room temperature to react for 2 h. Upon cooled, dilute hydrochloric acid was added dropwisely to adjust pH to 3, and the resulting mixture was concentrated under reduced pressure to remove dioxane, and the water phase was extracted with ethyl acetate (20 ml×3), the resulting organic phase was washed with acid, base and water until to be neutral, dried over anhydrous sodium sulfate, and the filtrate was concentrated and purified with a column to give a white solid (3 g, 85%).
Rf=0.7
Developer: n-butyl alcohol:water:acetic acid:ethyl acetate=1:1:1:1
Color development: iodine and 1% ninhydrin solution b) Preparation of N-2-naphthalenesulfonyl-D-leucyl-L-prolyl-{[(4-(N-benzyloxycarbonyl)amidinophenyl]methyl}amide N-2-naphthalenesulfonyl-D-leucine (1.6 g), L-prolyl-{[(4-(N-benzyloxycarbonyl)amidinophenyl]methyl}amide hydrochloride (2.26 g) and DIEA (1.47 g) were dissolved in anhydrous dichloromethane (40 ml), cooled down to 0° C. under the protection of nitrogen, and then HOBt (700 mg)

and EDCI (1.19 g) were added. The resulting mixture was stirred at 0° C. for 20 min and allowed to warm up naturally to room temperature to react for 5 hours. The organic layer was washed in turn with 5% potassium hydrosulphate solution, saturated sodium hydrogencarbonate solution and saturated saline solution, dried over anhydrous sodium sulfate, filtered and concentrated under reduced pressure to give 3.8 g crude product, which was purified with column chromatography to give a white solid (2.2 g, yield: 64%).

Rf=0.5
Developer: petroleum ether:ethyl acetate=1:2
Color development: ultraviolet and iodine
MS: 685 (M+H)

c) Preparation of N-2-naphthalenesulfonyl-D-leucyl-L-prolyl-[(4-amidinophenyl)methyl]amide hydrochloride The product (2 g) obtained in the above step was dissolved in methanol (20 ml), and 10% palladium-carbon (200 mg) was added. The resulting mixture aerated with hydrogen was allowed to react at 40° C. for 8 h, filtered and concentrated under reduced pressure to remove the solvent, dissolved with methanol (5 ml), and 15% HCl/ethyl acetate solution was added, the resulting mixture was evaporated to dryness to give a white solid (1.25 g, 71%).

MS: 550 (M+H)

Example 60

Test for Antithrombin Activity

In the test, the sample to be tested was added in the enzyme reaction system containing 0.15 U/ml lyophilized bovine thrombin standard substance purified from bovine blood to perform incubation for 15 minutes, and then specific substrate S2238 (0.075 μM) was added, and the change in absorbance value at 405 nM during 4 minutes was dynamically detected at room temperature by a UV-detector.

The inhibition ratio (% inhibition) against enzyme activity of the sample was calculated according to equation 1.

$$\% \text{ Inhibition} = [1 - \Delta As/\Delta Ac] \times 100\% \quad \text{Equation 1}$$

Wherein ΔAs represents the rate of change in inhibited absorbance value, and ΔAc represents the rate of change in uninhibited absorbance values. $IC_{50}$ value (the drug concentration when the enzyme activity is inhibited by 50%) was obtained by the nonlinear fitting calculation for the log value X of inhibition ratio (% inhibition) against concentration of sample according to equation 2.

$$\% \text{ Inhibition} = \frac{100}{1 + 10^{(LogIC50-X) \cdot h}} \quad \text{Equation 2}$$

Wherein h represents Hill coefficient. The $IC_{50}$ values (nM) of some compounds of the present invention are listed in the following table.

| compound | $IC_{50}$ |
|---|---|
| Example 2 | 115 |
| Example 4 | 47 |
| Example 6 | 154 |
| Example 12 | 561 |
| Example 18 | 30 |

-continued

| compound | $IC_{50}$ |
|---|---|
| Example 19 | 12 |
| Example 20 | 246 |
| Example 21 | 170 |
| Example 22 | 55 |
| Example 23 | 472 |
| Example 24 | 561 |
| Example 27 | 8 |
| melagatran | 69 |

The following formulation examples are only to illustrate, but not be intended to limit the scope of the present invention in any way. The active ingredient means the compound of general formula (I) or pharmaceutical acceptable salt or solvate thereof.

Example 61

Preparation of an Injection

Composition:

| | % W/V |
|---|---|
| active ingredient | 1 |
| normal saline | 100 |

Suitable dilute acid or base or buffer salt can be added to adjust pH to the most stable state, and antioxidants or metal chelating agents may also be included. The solution was filled into an aseptic ampule under aseptic conditions after filter sterilization.

Example 62

Preparation of a Tablet

Composition:

| | mg/tablet |
|---|---|
| active ingredient | 60 |
| microcrystalline cellulose | 35 |
| sodium carboxymethyl starch | 4.5 |
| cornstarch | 45 |
| magnesium stearate | 0.5 |
| talc powder | 1 |

The active ingredient was mixed sufficiently with excipients, sieved and tableted on a tabletting machine.

Example 63

Preparation of a Hard Capsule

Composition:

| | % W/W |
|---|---|
| active ingredient | 55 |
| dried starch | 43 |
| magnesium stearate | 2 |

The active ingredient was sieved and mixed with excipients with suitable equipments, and the mixture was filled into a hard gelatin capsule.

Example 64

Preparation of a Suspension

Composition

|  | mg/5 ml |
| --- | --- |
| active ingredient | 50 |
| sodium carboxymethyl cellulose | 75 |
| syrup | 1.2 ml |
| pigment | 0.05 ml |
| benzoic acid | 0.05 mg |
| purified water added to the total amount | 5 ml |

The active ingredient was sieved and mixed with sodium carboxymethyl cellulose and syrup to form a homogeneous cream, and pigment and benzoic acid were diluted with a part of purified water, added into the cream under stirring, and then adequate water was added to provide the desired volume.

Although the present invention has been described by the specific examples, it still should be understood that it can be further improved. This application should include any variation, use, or the applications which follow general rules of the present invention, and should include the applications which depart from the disclosure but belong to the known applications or conventional applications in the art, which are also suitable for the essential features aforesaid, furthermore included in the scope of the claims appended.

The invention claimed is:

1. A compound of formula (I), a pharmaceutically acceptable salt thereof, or a pharmaceutically acceptable prodrug thereof:

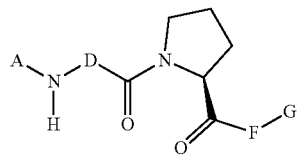

(I)

wherein:
A represents —$SO_2R^1$, —$COR^1$, —$R^2COR^1$, or —$R^2CO_2R^1$;

wherein:
$R^1$ represents cycloalkyl, aryl, —$R^3$-cycloalkyl, —$R^3$-aryl, or —$NR^4R^5$;
wherein cycloalkyl and aryl are substituted with 1 or 2 substituents selected from the group consisting of hydroxyl, carboxyl, halogen, $C_{1-4}$ alkyl, $C_{1-4}$ alkoxy, acyl, sulfonyl, sulfhydryl, alkylthio, cycloalkyl, heterocycloalkyl, amino, alkylamino, dialkylamino, cyano, ester group, trifluoromethyl, and $CONH_2$;
$R^2$ and $R^3$ represent unsubstituted $C_{1-6}$ alkyl;
$R^4$ and $R^5$ represent independently H or unsubstituted $C_{1-6}$ alkyl;
D represents

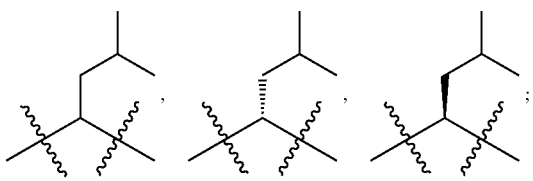

F represents —NH—$(CH_2)_m$—$R^6$;
wherein:
m represents 1;
$R^6$ represents unsubstituted

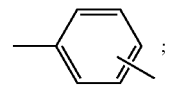

G represents

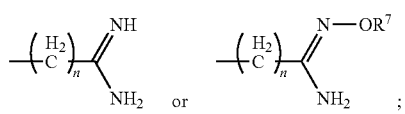

wherein:
n represents 0; and
$R^7$ represents H.

2. The compound of formula (I), a pharmaceutically acceptable salt thereof, or a pharmaceutically acceptable prodrug thereof according to claim 1, characterized in that the compound is:
N,N-dimethylaminosulfonyl-D-leucyl-L-prolyl-[(4-amidinophenyl)methyl]amide hydrochloride.

* * * * *

UNITED STATES PATENT AND TRADEMARK OFFICE
CERTIFICATE OF CORRECTION

PATENT NO.       : 9,434,760 B2                              Page 1 of 1
APPLICATION NO.  : 13/884196
DATED            : September 6, 2016
INVENTOR(S)      : Min Li et al.

It is certified that error appears in the above-identified patent and that said Letters Patent is hereby corrected as shown below:

Assignee(s) should read:

MIN LI, RINGOES, NJ
SHANGHAI INSTITUTE OF PHARMACEUTICAL INDUSTRY, SHANGHAI (CN)

Signed and Sealed this
Eleventh Day of July, 2017

Joseph Matal
*Performing the Functions and Duties of the*
*Under Secretary of Commerce for Intellectual Property and*
*Director of the United States Patent and Trademark Office*